US009580481B2

(12) United States Patent
Middelberg et al.

(10) Patent No.: US 9,580,481 B2
(45) Date of Patent: Feb. 28, 2017

(54) IMMUNOGENIC COMPOSITIONS AND METHODS THEREFOR

(75) Inventors: Anton Peter Jacob Middelberg, Brookfield (AU); Linda Hwee-Lin Lua, South Brisbane (AU)

(73) Assignee: University of Queensland, Queensland (AU)

( * ) Notice: Subject to any disclaimer, the term of this patent is extended or adjusted under 35 U.S.C. 154(b) by 0 days.

(21) Appl. No.: 14/237,698

(22) PCT Filed: Aug. 13, 2012

(86) PCT No.: PCT/AU2012/000952

§ 371 (c)(1), (2), (4) Date: May 1, 2014

(87) PCT Pub. No.: WO2013/020183

PCT Pub. Date: Feb. 14, 2013

(65) Prior Publication Data

US 2014/0302076 A1 Oct. 9, 2014

(30) Foreign Application Priority Data

Aug. 11, 2011 (AU) ................................ 2011903217

(51) Int. Cl.

| | |
|---|---|
| ***C07K 14/315*** | (2006.01) |
| ***A61K 39/09*** | (2006.01) |
| ***A61K 39/145*** | (2006.01) |
| ***A61K 39/155*** | (2006.01) |
| ***A61K 39/21*** | (2006.01) |
| ***C12N 15/62*** | (2006.01) |
| ***A61K 9/107*** | (2006.01) |
| ***A61K 9/51*** | (2006.01) |
| ***A61K 39/12*** | (2006.01) |
| ***C07K 14/005*** | (2006.01) |
| *A61K 39/00* | (2006.01) |

(52) U.S. Cl.

CPC .......... *C07K 14/315* (2013.01); *A61K 9/1075* (2013.01); *A61K 9/5184* (2013.01); *A61K 39/09* (2013.01); *A61K 39/092* (2013.01); *A61K 39/12* (2013.01); *A61K 39/145* (2013.01); *A61K 39/155* (2013.01); *A61K 39/21* (2013.01); *C07K 14/005* (2013.01); *C12N 15/62* (2013.01); *A61K 2039/523* (2013.01); *A61K 2039/5256* (2013.01); *A61K 2039/5258* (2013.01); *A61K 2039/55505* (2013.01); *A61K 2039/55555* (2013.01); *A61K 2039/55566* (2013.01); *C12N 2710/22022* (2013.01); *C12N 2710/22043* (2013.01); *C12N 2760/16134* (2013.01); *C12N 2760/18234* (2013.01)

(58) Field of Classification Search

None

See application file for complete search history.

(56) References Cited

U.S. PATENT DOCUMENTS

| | | | | |
|---|---|---|---|---|
| 2009/0215146 | A1 | 8/2009 | Reichel et al. | |
| 2010/0028375 | A1* | 2/2010 | Lua et al. | .................. 424/186.1 |

FOREIGN PATENT DOCUMENTS

| | | | |
|---|---|---|---|
| DE | 10 2004 036913 | A1 | 9/2006 |
| EP | 2 172 488 | A1 | 4/2010 |
| WO | WO 2006/008013 | A1 | 1/2006 |

OTHER PUBLICATIONS

Siray et al. An immunodominant, cross-reactive B-cell epitope region is located at the C-terminal part of the hamster polyomavirus major capsid protein VP1. Viral Immunol. 2000;13(4):533-45.*

Gillock et al. Truncation of the nuclear localization signal of polyomavirus VP1 results in a loss of DNA packaging when expressed in the baculovirus system. Virus Research 58 (1998) 149-160.*

ISIS Report Dec. 9, 2012, http://www.i-sis.org.uk/DNA_contamination_of_HPV_vaccines.php.*

Gedvilaite et al. Size and position of truncations in the carboxy-terminal region of major capsid protein VP1 of hamster polyomavirus expressed in yeast determine its assembly capacity. Arch Virol. Sep. 2006;151(9):1811-25. Epub Mar. 30, 2006.*

Chuan et al. Virus assembly occurs following a pH or Ca2+-triggered switch in the thermodynamic attraction between structural protein capsomeres. J. R. Soc. Interface (2010) 7, 409-421.*

Waheed et al. Transplastomic expression of a modified human papillomavirus L1 protein leading to the assembly of capsomeres in tobacco: a step towards cost-effective second-generation vaccines. Transgenic Res (2011) 20:271-282. Published online: Jun. 19, 2010.*

Middelberg, A., et al., "A microbial platform for rapid and low-cost virus-like particle and capsomere vaccines," *Vaccine*, 2011, vol. 29(41), pp. 7154-7162.

Chen, H., et al., "Study of infectious virus production_from HPV18/16 capsid chimeras," *Virology*, 2010, pp. 289-299, vol. 405.

Inoue, T., et al., "Engineering of SV40-based nano-capsules for delivery of heterologous proteins as fusions with the minor capsid proteins VP2/3," *Journal of Biotechnology*, 2008, pp. 181-192, vol. 134.

Tegerstedt, K., et al., "Murine Polyomavirus Virus-like Particles (VLPs) as Vectors for Gene and Immune Therapy and Vaccines against Viral Infections and Cancer," *Anticancer Research*, 2005, pp. 2601-2608, vol. 25.

* cited by examiner

*Primary Examiner* — Nick Zou

(74) *Attorney, Agent, or Firm* — Alston & Bird LLP

(57) ABSTRACT

The present invention provides compositions relating to viral capsomeres which comprise foreign immunogenic sequences for use in pharmaceutical compositions and methods of producing such compositions, and related isolated or purified protein and nucleic acid molecules, vectors, host cells, compositions, and methods of use to augment an immune response, immunize an animal and prophylactically or therapeutically treat a disease, disorder or condition. The viral capsomere may be derived from a polyomavirus and comprise an immunogen of interest at the N-terminus and further at the C-terminus and/or at one or more exposed loops of the capsomere.

28 Claims, 27 Drawing Sheets

```
VP1 wildtype     1 MAPKRKSGVSKCETKCTKACPRPAPVPKLLIKGGMEVLDLVTGPDSVTEIEAFLNPRMGQ  60
VP1 S1           1 MAPKRKSGVSKCETKCTKACPRPAPVPKLLIKGGMEVLDLVTGPDSVTEIEAFLNPRMGQ  60
VP1 S1S4         1 MAPKRKSGVSKCETKCTKACPRPAPVPKLLIKGGMEVLDLVTGPDSVTEIEAFLNPRMGQ  60
VP1 dNdC S1S4    1 ----------------------------LLIKGGMEVLDLVTGPDSVTEIEAFLNPRMGQ  32
VP1 dNdC 0000    1 ---------------------------HVLIKGGMEVLDLVTGPDSVTEIEAFLNPRMGQ  33
                                               .********************************

VP1 wildtype    61 PPTPESLTEGGQYYGWSRGINLATSD-TEDSPGNNTLPTWSMAKLQLPMLNEDLTCDTLQ 119
VP1 S1          61 PPTPESLTEGGQYYGWSRGINLATSAGTEDSPGNNTLPTWSMAKLQLPMLNEDLTCDTLQ 120
VP1 S1S4        61 PPTPESLTEGGQYYGWSRGINLATSAGTEDSPGNNTLPTWSMAKLQLPMLNEDLTCDTLQ 120
VP1 dNdC S1S4   33 PPTPESLTEGGQYYGWSRGINLATSAGTEDSPGNNTLPTWSMAKLQLPMLNEDLTCDTLQ  92
VP1 dNdC 0000   34 PPTPESLTEGGQYYGWSRGINLATSAGTEDSPGNNTLPTWSMAKLQLPMLNEDLTCDTLQ  93
                   *************************  **********************************

VP1 wildtype   120 MWEAVSVKTEVVGSGSLLDVHGFNKPTDTVNTKGISTPVEGSQYHVFAVGGEPLDLQGLV 179
VP1 S1         121 MWEAVSVKTEVVGSGSLLDVHGFNKPTDTVNTKGISTPVEGSQYHVFAVGGEPLDLQGLV 180
VP1 S1S4       121 MWEAVSVKTEVVGSGSLLDVHGFNKPTDTVNTKGISTPVEGSQYHVFAVGGEPLDLQGLV 180
VP1 dNdC S1S4   93 MWEAVSVKTEVVGSGSLLDVHGFNKPTDTVNTKGISTPVEGSQYHVFAVGGEPLDLQGLV 152
VP1 dNdC 0000   94 MWEAVSVKTEVVGSGSLLDVHGFNKPTDTVNTKGISTPVEGSQYHVFAVGGEPLDLQGLV 153
                   ************************************************************

VP1 wildtype   180 TDARTKYKEEGVVTIKTITKKDMVNKDQVLNPISKAKLDKDGMYPVEIWHPDPAKNENTR 239
VP1 S1         181 TDARTKYKEEGVVTIKTITKKDMVNKDQVLNPISKAKLDKDGMYPVEIWHPDPAKNENTR 240
VP1 S1S4       181 TDARTKYKEEGVVTIKTITKKDMVNKDQVLNPISKAKLDKDGMYPVEIWHPDPAKNENTR 240
VP1 dNdC S1S4  153 TDARTKYKEEGVVTIKTITKKDMVNKDQVLNPISKAKLDKDGMYPVEIWHPDPAKNENTR 212
VP1 dNdC 0000  154 TDARTKYKEEGVVTIKTITKKDMVNKDQVLNPISKAKLDKDGMYPVEIWHPDPAKNENTR 213
                   ************************************************************

VP1 wildtype   240 YFGNYTGGTTTPPVLQFTNTLTTVLLDENGVGPLCKGEGLYLSCVDIMGWRVTR-NYDVH 298
VP1 S1         241 YFGNYTGGTTTPPVLQFTNTLTTVLLDENGVGPLCKGEGLYLSCVDIMGWRVTR-NYDVH 299
VP1 S1S4       241 YFGNYTGGTTTPPVLQFTNTLTTVLLDENGVGPLCKGEGLYLSCVDIMGWRVTRSAYDVH 300
VP1 dNdC S1S4  213 YFGNYTGGTTTPPVLQFTNTLTTVLLDENGVGPLCKGEGLYLSCVDIMGWRVTRSAYDVH 272
VP1 dNdC 0000  214 YFGNYTGGTTTPPVLQFTNTLTTVLLDENGVGPLCKGEGLYLSCVDIMGWRVTRSAYDVH 273
                   ******************************************************  ****

VP1 wildtype   299 HWRGLPRYFKITLRKRWVKNPYPMASLISSLFNNMLPQVQGQPMEGENTQVEEVRVYDGT 358
VP1 S1         300 HWRGLPRYFKITLRKRWVKNPYPMASLISSLFNNMLPQVQGQPMEGENTQVEEVRVYDGT 359
VP1 S1S4       301 HWRGLPRYFKITLRKRWVKNPYPMASLISSLFNNMLPQVQGQPMEGENTQVEEVRVYDGT 360
VP1 dNdC S1S4  273 HWRGLPRYFKITLRKRWVKNPYP------------------------------------- 295
VP1 dNdC 0000  274 HWRGLPRYFKITLRKRWVKNPYV------------------------------------- 296
                   **********************

VP1 wildtype   359 EPVPGDPDMTRYVDRFGKTKTVFPGN 384
VP1 S1         360 EPVPGDPDMTRYVDRFGKTKTVFPGN 385
VP1 S1S4       361 EPVPGDPDMTRYVDRFGKTKTVFPGN 386
VP1 dNdC S1S4  296 -------------------------- 295
VP1 dNdC 0000  297 -------------------------- 296
```

Figure 1

```
VP1 wildtype       1 MAPKRKSGVSKCETKCTKACPRPAPVPKLLIKGGMEVLDLVTGPDSVTEI  50
VP1 dNdC 0000      1 ---------------------------HVLIKGGMEVLDLVTGPDSVTEI  23
VP1 dNdC 1011A     1 ---------HDSNKGVTAACPH-AGAKSVLIKGGMEVLDLVTGPDSVTEI  40
                                                 .*********************

VP1 wildtype      51 EAFLNPRMGQPPTPESLTEGGQYYGWSRGINLATSD-TEDSPGNNTLPTW  99
VP1 dNdC 0000     24 EAFLNPRMGQPPTPESLTEGGQYYGWSRGINLATSAGTEDSPGNNTLPTW  73
VP1 dNdC 1011A    41 EAFLNPRMGQPPTPESLTEGGQYYGWSRGINLATSAGTEDSPGNNTLPTW  90
                     ***********************************  *************

VP1 wildtype     100 SMAKLQLPMLNEDLTCDTLQMWEAVSVKTEVVGSGSLLDVHGFNKPTDTV 149
VP1 dNdC 0000     74 SMAKLQLPMLNEDLTCDTLQMWEAVSVKTEVVGSGSLLDVHGFNKPTDTV 123
VP1 dNdC 1011A    91 SMAKLQLPMLNEDLTCDTLQMWEAVSVKTEVVGSGSLLDVHGFNKPTDTV 140
                     **************************************************

VP1 wildtype     150 NTKGISTPVEGSQYHVFAVGGEPLDLQGLVTDARTKYKEEGVVTIKTITK 199
VP1 dNdC 0000    124 NTKGISTPVEGSQYHVFAVGGEPLDLQGLVTDARTKYKEEGVVTIKTITK 173
VP1 dNdC 1011A   141 NTKGISTPVEGSQYHVFAVGGEPLDLQGLVTDARTKYKEEGVVTIKTITK 190
                     **************************************************

VP1 wildtype     200 KDMVNKDQVLNPISKAKLDKDGMYPVEIWHPDPAKNENTRYFGNYTGGTT 249
VP1 dNdC 0000    174 KDMVNKDQVLNPISKAKLDKDGMYPVEIWHPDPAKNENTRYFGNYTGGTT 223
VP1 dNdC 1011A   191 KDMVNKDQVLNPISKAKLDKDGMYPVEIWHPDPAKNENTRYFGNYTGGTT 240
                     **************************************************

VP1 wildtype     250 TPPVLQFTNTLTTVLLDENGVGPLCKGEGLYLSCVDIMGWRVTR------ 293
VP1 dNdC 0000    224 TPPVLQFTNTLTTVLLDENGVGPLCKGEGLYLSCVDIMGWRVTR------ 267
VP1 dNdC 1011A   241 TPPVLQFTNTLTTVLLDENGVGPLCKGEGLYLSCVDIMGWRVTRSDSNKG 290
                     ********************************************

VP1 wildtype     294 ------------NYDVHHWRGLPRYFKITLRKRWVKNPYPMASLISSLFN 331
VP1 dNdC 0000    268 -----------SAYDVHHWRGLPRYFKITLRKRWVKNPYV---------- 296
VP1 dNdC 1011A   291 VTAACPHAGAKSAYDVHHWRGLPRYFKITLRKRWVKNPYDSNKGVTAACP 340
                                  **************************

VP1 wildtype     332 NMLPQVQGQPMEGENTQVEEVRVYDGTEPVPGDPDMTRYVDRFGKTKTVF 381
VP1 dNdC 0000    297 -------------------------------------------------- 296
VP1 dNdC 1011A   341 HAGAKSV------------------------------------------- 347

VP1 wildtype     382 PGN 384
VP1 dNdC 0000    297 --- 296
VP1 dNdC 1011A   348 --- 347
```

Figure 2

```
VP1 wildtype       1 MAPKRKSGVSKCETKCTKACPRPAPVPK-------------------LLI  31
VP1 dNdC 0000      1 -----------------------------------------------HVLI   4
VP1dNdC 1011M2e    1 -----------------------HSLLTEVETPTRSEWECRCSDSSDVLI  27
VP1dNdC 2022M2e    1 HSLLTEVETPTRSEWECRCSDSSDSLLTEVETPTRSEWECRCSDSSDVLI  50
                                                                      .**

VP1 wildtype      32 KGGMEVLDLVTGPDSVTEIEAFLNPRMGQPPTPESLTEGGQYYGWSRGIN  81
VP1 dNdC 0000      5 KGGMEVLDLVTGPDSVTEIEAFLNPRMGQPPTPESLTEGGQYYGWSRGIN  54
VP1dNdC 1011M2e   28 KGGMEVLDLVTGPDSVTEIEAFLNPRMGQPPTPESLTEGGQYYGWSRGIN  77
VP1dNdC 2022M2e   51 KGGMEVLDLVTGPDSVTEIEAFLNPRMGQPPTPESLTEGGQYYGWSRGIN 100
                     **************************************************

VP1 wildtype      82 LATSD-TEDSPGNNTLPTWSMAKLQLPMLNEDLTCDTLQMWEAVSVKTEV 130
VP1 dNdC 0000     55 LATSAGTEDSPGNNTLPTWSMAKLQLPMLNEDLTCDTLQMWEAVSVKTEV 104
VP1dNdC 1011M2e   78 LATSAGTEDSPGNNTLPTWSMAKLQLPMLNEDLTCDTLQMWEAVSVKTEV 127
VP1dNdC 2022M2e  101 LATSAGTEDSPGNNTLPTWSMAKLQLPMLNEDLTCDTLQMWEAVSVKTEV 150
                     ****  ********************************************

VP1 wildtype     131 VGSGSLLDVHGFNKPTDTVNTKGISTPVEGSQYHVFAVGGEPLDLQGLVT 180
VP1 dNdC 0000    105 VGSGSLLDVHGFNKPTDTVNTKGISTPVEGSQYHVFAVGGEPLDLQGLVT 154
VP1dNdC 1011M2e  128 VGSGSLLDVHGFNKPTDTVNTKGISTPVEGSQYHVFAVGGEPLDLQGLVT 177
VP1dNdC 2022M2e  151 VGSGSLLDVHGFNKPTDTVNTKGISTPVEGSQYHVFAVGGEPLDLQGLVT 200
                     **************************************************

VP1 wildtype     181 DARTKYKEEGVVTIKTITKKDMVNKDQVLNPISKAKLDKDGMYPVEIWHP 230
VP1 dNdC 0000    155 DARTKYKEEGVVTIKTITKKDMVNKDQVLNPISKAKLDKDGMYPVEIWHP 204
VP1dNdC 1011M2e  178 DARTKYKEEGVVTIKTITKKDMVNKDQVLNPISKAKLDKDGMYPVEIWHP 227
VP1dNdC 2022M2e  201 DARTKYKEEGVVTIKTITKKDMVNKDQVLNPISKAKLDKDGMYPVEIWHP 250
                     **************************************************

VP1 wildtype     231 DPAKNENTRYFGNYTGGTTTPPVLQFTNTLTTVLLDENGVGPLCKGEGLY 280
VP1 dNdC 0000    205 DPAKNENTRYFGNYTGGTTTPPVLQFTNTLTTVLLDENGVGPLCKGEGLY 254
VP1dNdC 1011M2e  228 DPAKNENTRYFGNYTGGTTTPPVLQFTNTLTTVLLDENGVGPLCKGEGLY 277
VP1dNdC 2022M2e  251 DPAKNENTRYFGNYTGGTTTPPVLQFTNTLTTVLLDENGVGPLCKGEGLY 300
                     **************************************************

VP1 wildtype     281 LSCVDIMGWRVTRN------------------------------------ 294
VP1 dNdC 0000    255 LSCVDIMGWRVTRS------------------------------------ 268
VP1dNdC 1011M2e  278 LSCVDIMGWRVTRSSLLTEVETPTRSEWECRCSDSSD------------- 314
VP1dNdC 2022M2e  301 LSCVDIMGWRVTRSSLLTEVETPTRSEWECRCSDSSDSLLTEVETPTRSE 350
                     *************

VP1 wildtype     295 -----------YDVHHWRGLPRYFKITLRKRWVKNPYPMASLISSLFNNM 333
VP1 dNdC 0000    269 ----------AYDVHHWRGLPRYFKITLRKRWVKNPYV------------ 296
VP1dNdC 1011M2e  315 ----------AYDVHHWRGLPRYFKITLRKRWVKNPYSLLTEVETPTRSE 354
VP1dNdC 2022M2e  351 WECRCSDSSDAYDVHHWRGLPRYFKITLRKRWVKNPYSLLTEVETPTRSE 400
                                **************************

VP1 wildtype     334 LPQVQGQPMEGENTQVEEVRVYDGTEPVPGDPDMTRYVDRFGKTKTVFPG 383
VP1 dNdC 0000    297 -------------------------------------------------- 296
VP1dNdC 1011M2e  355 WECRCSDSSDV--------------------------------------- 365
VP1dNdC 2022M2e  401 WECRCSDSSDSLLTEVETPTRSEWECRCSDSSDV---------------- 434

VP1 wildtype     384 N 384
VP1 dNdC 0000    297 - 296
VP1dNdC 1011M2e  366 - 365
VP1dNdC 2022M2e  435 - 434
```

Figure 6

1011M2e - elute

2022M2e - elute

```
VP1 wildtype        1 MAPKRKSGVSKCETKCTKACPRPAPVPKLLIKGGMEVLDLVTGPDSVTEI  50
VP1 dNdC 0000       1 ---------------------------HVLIKGGMEVLDLVTGPDSVTEI  23
VP1dNdC 1011G12     1 --------------HGLPNQIMLQKTTSVLIKGGMEVLDLVTGPDSVTEI  36
VP1dNdC 1011G4      1 ----------------HVRPKSDSGDYNVLIKGGMEVLDLVTGPDSVTEI  34
VP1dNdC 1011G5      1 ----------------HPIIHSKYSKAEVLIKGGMEVLDLVTGPDSVTEI  34
VP1dNdC 1011G9      1 ------------HVEIYDTGDSVIRPKLVLIKGGMEVLDLVTGPDSVTEI  38
VP1dNdC 1011G10     1 -------------HLEKIGSCTRGIAKQVLIKGGMEVLDLVTGPDSVTEI  37
                                                  .*********************

VP1 wildtype       51 EAFLNPRMGQPPTPESLTEGGQYYGWSRGINLATSD-TEDSPGNNTLPTW  99
VP1 dNdC 0000      24 EAFLNPRMGQPPTPESLTEGGQYYGWSRGINLATSAGTEDSPGNNTLPTW  73
VP1dNdC 1011G12    37 EAFLNPRMGQPPTPESLTEGGQYYGWSRGINLATSAGTEDSPGNNTLPTW  86
VP1dNdC 1011G4     35 EAFLNPRMGQPPTPESLTEGGQYYGWSRGINLATSAGTEDSPGNNTLPTW  84
VP1dNdC 1011G5     35 EAFLNPRMGQPPTPESLTEGGQYYGWSRGINLATSAGTEDSPGNNTLPTW  84
VP1dNdC 1011G9     39 EAFLNPRMGQPPTPESLTEGGQYYGWSRGINLATSAGTEDSPGNNTLPTW  88
VP1dNdC 1011G10    38 EAFLNPRMGQPPTPESLTEGGQYYGWSRGINLATSAGTEDSPGNNTLPTW  87
                      ***********************************  *************

VP1 wildtype      100 SMAKLQLPMLNEDLTCDTLQMWEAVSVKTEVVGSGSLLDVHGFNKPTDTV 149
VP1 dNdC 0000      74 SMAKLQLPMLNEDLTCDTLQMWEAVSVKTEVVGSGSLLDVHGFNKPTDTV 123
VP1dNdC 1011G12    87 SMAKLQLPMLNEDLTCDTLQMWEAVSVKTEVVGSGSLLDVHGFNKPTDTV 136
VP1dNdC 1011G4     85 SMAKLQLPMLNEDLTCDTLQMWEAVSVKTEVVGSGSLLDVHGFNKPTDTV 134
VP1dNdC 1011G5     85 SMAKLQLPMLNEDLTCDTLQMWEAVSVKTEVVGSGSLLDVHGFNKPTDTV 134
VP1dNdC 1011G9     89 SMAKLQLPMLNEDLTCDTLQMWEAVSVKTEVVGSGSLLDVHGFNKPTDTV 138
VP1dNdC 1011G10    88 SMAKLQLPMLNEDLTCDTLQMWEAVSVKTEVVGSGSLLDVHGFNKPTDTV 137
                      **************************************************

VP1 wildtype      150 NTKGISTPVEGSQYHVFAVGGEPLDLQGLVTDARTKYKEEGVVTIKTITK 199
VP1 dNdC 0000     124 NTKGISTPVEGSQYHVFAVGGEPLDLQGLVTDARTKYKEEGVVTIKTITK 173
VP1dNdC 1011G12   137 NTKGISTPVEGSQYHVFAVGGEPLDLQGLVTDARTKYKEEGVVTIKTITK 186
VP1dNdC 1011G4    135 NTKGISTPVEGSQYHVFAVGGEPLDLQGLVTDARTKYKEEGVVTIKTITK 184
VP1dNdC 1011G5    135 NTKGISTPVEGSQYHVFAVGGEPLDLQGLVTDARTKYKEEGVVTIKTITK 184
VP1dNdC 1011G9    139 NTKGISTPVEGSQYHVFAVGGEPLDLQGLVTDARTKYKEEGVVTIKTITK 188
VP1dNdC 1011G10   138 NTKGISTPVEGSQYHVFAVGGEPLDLQGLVTDARTKYKEEGVVTIKTITK 187
                      **************************************************

VP1 wildtype      200 KDMVNKDQVLNPISKAKLDKDGMYPVEIWHPDPAKNENTRYFGNYTGGTT 249
VP1 dNdC 0000     174 KDMVNKDQVLNPISKAKLDKDGMYPVEIWHPDPAKNENTRYFGNYTGGTT 223
VP1dNdC 1011G12   187 KDMVNKDQVLNPISKAKLDKDGMYPVEIWHPDPAKNENTRYFGNYTGGTT 236
VP1dNdC 1011G4    185 KDMVNKDQVLNPISKAKLDKDGMYPVEIWHPDPAKNENTRYFGNYTGGTT 234
VP1dNdC 1011G5    185 KDMVNKDQVLNPISKAKLDKDGMYPVEIWHPDPAKNENTRYFGNYTGGTT 234
VP1dNdC 1011G9    189 KDMVNKDQVLNPISKAKLDKDGMYPVEIWHPDPAKNENTRYFGNYTGGTT 238
VP1dNdC 1011G10   188 KDMVNKDQVLNPISKAKLDKDGMYPVEIWHPDPAKNENTRYFGNYTGGTT 237
                      **************************************************

VP1 wildtype      250 TPPVLQFTNTLTTVLLDENGVGPLCKGEGLYLSCVDIMGWRVTRN----- 294
VP1 dNdC 0000     224 TPPVLQFTNTLTTVLLDENGVGPLCKGEGLYLSCVDIMGWRVTRS----- 268
VP1dNdC 1011G12   237 TPPVLQFTNTLTTVLLDENGVGPLCKGEGLYLSCVDIMGWRVTRSGLPNQ 286
VP1dNdC 1011G4    235 TPPVLQFTNTLTTVLLDENGVGPLCKGEGLYLSCVDIMGWRVTRSVRPKS 284
VP1dNdC 1011G5    235 TPPVLQFTNTLTTVLLDENGVGPLCKGEGLYLSCVDIMGWRVTRSPIIHS 284
VP1dNdC 1011G9    239 TPPVLQFTNTLTTVLLDENGVGPLCKGEGLYLSCVDIMGWRVTRSVEIYD 288
VP1dNdC 1011G10   238 TPPVLQFTNTLTTVLLDENGVGPLCKGEGLYLSCVDIMGWRVTRSLEKIG 287
                      ********************************************

VP1 wildtype      295 -----------YDVHHWRGLPRYFKITLRKRWVKNPYPMASLISSLFNNM 333
VP1 dNdC 0000     269 ----------AYDVHHWRGLPRYFKITLRKRWVKNPYV------------ 296
VP1dNdC 1011G12   287 IMLQKTTS--AYDVHHWRGLPRYFKITLRKRWVKNPYGLPNQIMLQKTTS 334
VP1dNdC 1011G4    285 DSGDYN----AYDVHHWRGLPRYFKITLRKRWVKNPYVRPKSDSGDYNV- 329
VP1dNdC 1011G5    285 KYSKAE----AYDVHHWRGLPRYFKITLRKRWVKNPYPIIHSKYSKAEV- 329
VP1dNdC 1011G9    289 TGDSVIRPKLAYDVHHWRGLPRYFKITLRKRWVKNPYVEIYDTGDSVIRP 338
VP1dNdC 1011G10   288 SCTRGIAKQ-AYDVHHWRGLPRYFKITLRKRWVKNPYLEKIGSCTRGIAK 336
                                 **************************
```

Figure 12

```
VP1 wildtype     334 LPQVQGQPMEGENTQVEEVRVYDGTEPVPGDPDMTRYVDRFGKTKTVFPG 383
VP1 dNdC 0000    297 -------------------------------------------------- 296
VP1dNdC 1011G12  335 V------------------------------------------------- 335
VP1dNdC 1011G4   330 -------------------------------------------------- 329
VP1dNdC 1011G5   330 -------------------------------------------------- 329
VP1dNdC 1011G9   339 KLV----------------------------------------------- 341
VP1dNdC 1011G10  337 QV------------------------------------------------ 338

VP1 wildtype     384 N 384
VP1 dNdC 0000    297 - 296
VP1dNdC 1011G12  336 - 335
VP1dNdC 1011G4   330 - 329
VP1dNdC 1011G5   330 - 329
VP1dNdC 1011G9   342 - 341
VP1dNdC 1011G10  339 - 338
```

Figure 12 Continued

```
VP1 wildtype      1 MAPKRKSGVSKCETKCTKACPRPAPVPK-LLIKGGMEVLDLVTGPDSVTE  49
VP1 dNdC 0000     1 ----------------------------HVLIKGGMEVLDLVTGPDSVTE  22
1011GAS1          1 HNSKTPAPAPAVPVKKEATKSKLSEAELHVLIKGGMEVLDLVTGPDSVTE  50
1011GAS2          1 HNSKNP-----VPVKKEA---KLSEAEL-VLIKGGMEVLDLVTGPDSVTE  41
1011GAS3          1 HLKMLN-------RDLEQAYNELSGEAH-VLIKGGMEVLDLVTGPDSVTE  42
                                                .********************

VP1 wildtype     50 IEAFLNPRMGQPPTPESLTEGGQYYGWSRGINLATSD-TEDSPGNNTLPT  98
VP1 dNdC 0000    23 IEAFLNPRMGQPPTPESLTEGGQYYGWSRGINLATSAGTEDSPGNNTLPT  72
1011GAS1         51 IEAFLNPRMGQPPTPESLTEGGQYYGWSRGINLATSAGTEDSPGNNTLPT 100
1011GAS2         42 IEAFLNPRMGQPPTPESLTEGGQYYGWSRGINLATSAGTEDSPGNNTLPT  91
1011GAS3         43 IEAFLNPRMGQPPTPESLTEGGQYYGWSRGINLATSAGTEDSPGNNTLPT  92
                    ************************************  ************

VP1 wildtype     99 WSMAKLQLPMLNEDLTCDTLQMWEAVSVKTEVVGSGSLLDVHGFNKPTDT 148
VP1 dNdC 0000    73 WSMAKLQLPMLNEDLTCDTLQMWEAVSVKTEVVGSGSLLDVHGFNKPTDT 122
1011GAS1        101 WSMAKLQLPMLNEDLTCDTLQMWEAVSVKTEVVGSGSLLDVHGFNKPTDT 150
1011GAS2         92 WSMAKLQLPMLNEDLTCDTLQMWEAVSVKTEVVGSGSLLDVHGFNKPTDT 141
1011GAS3         93 WSMAKLQLPMLNEDLTCDTLQMWEAVSVKTEVVGSGSLLDVHGFNKPTDT 142
                    **************************************************

VP1 wildtype    149 VNTKGISTPVEGSQYHVFAVGGEPLDLQGLVTDARTKYKEEGVVTIKTIT 198
VP1 dNdC 0000   123 VNTKGISTPVEGSQYHVFAVGGEPLDLQGLVTDARTKYKEEGVVTIKTIT 172
1011GAS1        151 VNTKGISTPVEGSQYHVFAVGGEPLDLQGLVTDARTKYKEEGVVTIKTIT 200
1011GAS2        142 VNTKGISTPVEGSQYHVFAVGGEPLDLQGLVTDARTKYKEEGVVTIKTIT 191
1011GAS3        143 VNTKGISTPVEGSQYHVFAVGGEPLDLQGLVTDARTKYKEEGVVTIKTIT 192
                    **************************************************

VP1 wildtype    199 KKDMVNKDQVLNPISKAKLDKDGMYPVEIWHPDPAKNENTRYFGNYTGGT 248
VP1 dNdC 0000   173 KKDMVNKDQVLNPISKAKLDKDGMYPVEIWHPDPAKNENTRYFGNYTGGT 222
1011GAS1        201 KKDMVNKDQVLNPISKAKLDKDGMYPVEIWHPDPAKNENTRYFGNYTGGT 250
1011GAS2        192 KKDMVNKDQVLNPISKAKLDKDGMYPVEIWHPDPAKNENTRYFGNYTGGT 241
1011GAS3        193 KKDMVNKDQVLNPISKAKLDKDGMYPVEIWHPDPAKNENTRYFGNYTGGT 242
                    **************************************************

VP1 wildtype    249 TTPPVLQFTNTLTTVLLDENGVGPLCKGEGLYLSCVDIMGWRVTRN---- 294
VP1 dNdC 0000   223 TTPPVLQFTNTLTTVLLDENGVGPLCKGEGLYLSCVDIMGWRVTRS---- 268
1011GAS1        251 TTPPVLQFTNTLTTVLLDENGVGPLCKGEGLYLSCVDIMGWRVTRSNSKT 300
1011GAS2        242 TTPPVLQFTNTLTTVLLDENGVGPLCKGEGLYLSCVDIMGWRVTRSNSKN 291
1011GAS3        243 TTPPVLQFTNTLTTVLLDENGVGPLCKGEGLYLSCVDIMGWRVTRSLKML 292
                    *********************************************

VP1 wildtype    295 -------------------------YDVHHWRGLPRYFKITLRKRWVKNP 319
VP1 dNdC 0000   269 ------------------------AYDVHHWRGLPRYFKITLRKRWVKNP 294
1011GAS1        301 PAPAPAVPVKKEATKSKLSEAELHAYDVHHWRGLPRYFKITLRKRWVKNP 350
1011GAS2        292 P-----VPVKKEA---KLSEAEL-AYDVHHWRGLPRYFKITLRKRWVKNP 332
1011GAS3        293 N-------RDLEQAYNELSGEAH-AYDVHHWRGLPRYFKITLRKRWVKNP 334
                                             *************************

VP1 wildtype    320 YPMASLISSLFNNMLPQVQGQPMEGENTQVEEVRVYDGTEPVPGDPDMTR 369
VP1 dNdC 0000   295 YV------------------------------------------------ 296
1011GAS1        351 YNSKTPAPAPAVPVKKEATKSKLSEAELHV-------------------- 380
1011GAS2        333 YNSKNP-----VPVKKEA---KLSEAELV--------------------- 353
1011GAS3        335 YLKMLN-------RDLEQAYNELSGEAHV--------------------- 356
                    *

VP1 wildtype    370 YVDRFGKTKTVFPGN 384
VP1 dNdC 0000   297 --------------- 296
1011GAS1        381 --------------- 380
1011GAS2        354 --------------- 353
1011GAS3        357 --------------- 356
```

Figure 13

```
VP1 wildtype        1 ---------------------------MAPKRKSGVSKCETKCTKACPRP  23
M2e-VP1-S1A         1 SLLTEVETPTRNEWECRCSDSSDGSGGMAPKRKSGVSKCETKCTKACPRP  50
M2e-VP1-S1B-S4A     1 SLLTEVETPTRNEWECRCSDSSDGSGGMAPKRKSGVSKCETKCTKACPRP  50
                                                 ***********************

VP1 wildtype       24 APVPKLLIKGGMEVLDLVTGPDSVTEIEAFLNPRMGQPPTPESLTEGGQY  73
M2e-VP1-S1A        51 APVPKLLIKGGMEVLDLVTGPDSVTEIEAFLNPRMGQPPTPESLTEGGQY 100
M2e-VP1-S1B-S4A    51 APVPKLLIKGGMEVLDLVTGPDSVTEIEAFLNPRMGQPPTPESLTEGGQY 100
                      **************************************************

VP1 wildtype       74 YGWSRGINLAT------------------SDTEDSPGNNTLPTWSMAKLQ 105
M2e-VP1-S1A       101 YGWSRGINLATSAP----------YNGKSSGTEDSPGNNTLPTWSMAKLQ 140
M2e-VP1-S1B-S4A   101 YGWSRGINLATSAGNDAAEQTKLYQNPTTYGTEDSPGNNTLPTWSMAKLQ 150
                      ***********                    *******************

VP1 wildtype      106 LPMLNEDLTCDTLQMWEAVSVKTEVVGSGSLLDVHGFNKPTDTVNTKGIS 155
M2e-VP1-S1A       141 LPMLNEDLTCDTLQMWEAVSVKTEVVGSGSLLDVHGFNKPTDTVNTKGIS 190
M2e-VP1-S1B-S4A   151 LPMLNEDLTCDTLQMWEAVSVKTEVVGSGSLLDVHGFNKPTDTVNTKGIS 200
                      **************************************************

VP1 wildtype      156 TPVEGSQYHVFAVGGEPLDLQGLVTDARTKYKEEGVVTIKTITKKDMVNK 205
M2e-VP1-S1A       191 TPVEGSQYHVFAVGGEPLDLQGLVTDARTKYKEEGVVTIKTITKKDMVNK 240
M2e-VP1-S1B-S4A   201 TPVEGSQYHVFAVGGEPLDLQGLVTDARTKYKEEGVVTIKTITKKDMVNK 250
                      **************************************************

VP1 wildtype      206 DQVLNPISKAKLDKDGMYPVEIWHPDPAKNENTRYFGNYTGGTTTPPVLQ 255
M2e-VP1-S1A       241 DQVLNPISKAKLDKDGMYPVEIWHPDPAKNENTRYFGNYTGGTTTPPVLQ 290
M2e-VP1-S1B-S4A   251 DQVLNPISKAKLDKDGMYPVEIWHPDPAKNENTRYFGNYTGGTTTPPVLQ 300
                      **************************************************

VP1 wildtype      256 FTNTLTTVLLDENGVGPLCKGEGLYLSCVDIMGWRVTRN--------YDV 297
M2e-VP1-S1A       291 FTNTLTTVLLDENGVGPLCKGEGLYLSCVDIMGWRVTRN--------YDV 332
M2e-VP1-S1B-S4A   301 FTNTLTTVLLDENGVGPLCKGEGLYLSCVDIMGWRVTRSPYNGKSSAYDV 350
                      ***************************************        ***

VP1 wildtype      298 HHWRGLPRYFKITLRKRWVKNPYPMASLISSLFNNMLPQVQGQPMEGENT 347
M2e-VP1-S1A       333 HHWRGLPRYFKITLRKRWVKNPYPMASLISSLFNNMLPQVQGQPMEGENT 382
M2e-VP1-S1B-S4A   351 HHWRGLPRYFKITLRKRWVKNPYPMASLISSLFNNMLPQVQGQPMEGENT 400
                      **************************************************

VP1 wildtype      348 QVEEVRVYDGTEPVPGDPDMTRYVDRFGKTKTVFPGN 384
M2e-VP1-S1A       383 QVEEVRVYDGTEPVPGDPDMTRYVDRFGKTKTVFPGN 419
M2e-VP1-S1B-S4A   401 QVEEVRVYDGTEPVPGDPDMTRYVDRFGKTKTVFPGN 437
                      *************************************
```

Figure 14

```
VP1 wildtype       1 MAPKRKSGVSKCETKCTKACPRPAPVPKLLIKGGMEVLDLVTGPDSVTEI  50
VP1 dNdC 0000      1 ---------------------------HVLIKGGMEVLDLVTGPDSVTEI  23
VP1 dNdC 1011E7    1 --------HQAEPDRAHYNIVTFCCKCDVLIKGGMEVLDLVTGPDSVTEI  42
VP1 dNdC 1011CTL   1 -------------HRAHYNIVTF-----VLIKGGMEVLDLVTGPDSVTEI  32
                                                 .*********************

VP1 wildtype      51 EAFLNPRMGQPPTPESLTEGGQYYGWSRGINLATSD-TEDSPGNNTLPTW  99
VP1 dNdC 0000     24 EAFLNPRMGQPPTPESLTEGGQYYGWSRGINLATSAGTEDSPGNNTLPTW  73
VP1 dNdC 1011E7   43 EAFLNPRMGQPPTPESLTEGGQYYGWSRGINLATSAGTEDSPGNNTLPTW  92
VP1 dNdC 1011CTL  33 EAFLNPRMGQPPTPESLTEGGQYYGWSRGINLATSAGTEDSPGNNTLPTW  82
                     ***********************************  *************

VP1 wildtype     100 SMAKLQLPMLNEDLTCDTLQMWEAVSVKTEVVGSGSLLDVHGFNKPTDTV 149
VP1 dNdC 0000     74 SMAKLQLPMLNEDLTCDTLQMWEAVSVKTEVVGSGSLLDVHGFNKPTDTV 123
VP1 dNdC 1011E7   93 SMAKLQLPMLNEDLTCDTLQMWEAVSVKTEVVGSGSLLDVHGFNKPTDTV 142
VP1 dNdC 1011CTL  83 SMAKLQLPMLNEDLTCDTLQMWEAVSVKTEVVGSGSLLDVHGFNKPTDTV 132
                     **************************************************

VP1 wildtype     150 NTKGISTPVEGSQYHVFAVGGEPLDLQGLVTDARTKYKEEGVVTIKTITK 199
VP1 dNdC 0000    124 NTKGISTPVEGSQYHVFAVGGEPLDLQGLVTDARTKYKEEGVVTIKTITK 173
VP1 dNdC 1011E7  143 NTKGISTPVEGSQYHVFAVGGEPLDLQGLVTDARTKYKEEGVVTIKTITK 192
VP1 dNdC 1011CTL133 NTKGISTPVEGSQYHVFAVGGEPLDLQGLVTDARTKYKEEGVVTIKTITK 182
                     **************************************************

VP1 wildtype     200 KDMVNKDQVLNPISKAKLDKDGMYPVEIWHPDPAKNENTRYFGNYTGGTT 249
VP1 dNdC 0000    174 KDMVNKDQVLNPISKAKLDKDGMYPVEIWHPDPAKNENTRYFGNYTGGTT 223
VP1 dNdC 1011E7  193 KDMVNKDQVLNPISKAKLDKDGMYPVEIWHPDPAKNENTRYFGNYTGGTT 242
VP1 dNdC 1011CTL183 KDMVNKDQVLNPISKAKLDKDGMYPVEIWHPDPAKNENTRYFGNYTGGTT 232
                     **************************************************

VP1 wildtype     250 TPPVLQFTNTLTTVLLDENGVGPLCKGEGLYLSCVDIMGWRVTRN----- 294
VP1 dNdC 0000    224 TPPVLQFTNTLTTVLLDENGVGPLCKGEGLYLSCVDIMGWRVTRS----- 268
VP1 dNdC 1011E7  243 TPPVLQFTNTLTTVLLDENGVGPLCKGEGLYLSCVDIMGWRVTRSQAEPD 292
VP1 dNdC 1011CTL233 TPPVLQFTNTLTTVLLDENGVGPLCKGEGLYLSCVDIMGWRVTRS----- 277
                     ********************************************

VP1 wildtype     295 ---------------YDVHHWRGLPRYFKITLRKRWVKNPYPMASLISSL 329
VP1 dNdC 0000    269 --------------AYDVHHWRGLPRYFKITLRKRWVKNPYV-------- 296
VP1 dNdC 1011E7  293 RAHYNIVTFCCKCDAYDVHHWRGLPRYFKITLRKRWVKNPYQAEPDRAHY 342
VP1 dNdC 1011CTL278 RAHYNIVTF-----AYDVHHWRGLPRYFKITLRKRWVKNPY-----RAHY 317
                                    **************************

VP1 wildtype     330 FNNMLPQVQGQPMEGENTQVEEVRVYDGTEPVPGDPDMTRYVDRFGKTKT 379
VP1 dNdC 0000    297 -------------------------------------------------- 296
VP1 dNdC 1011E7  343 NIVTFCCKCDV--------------------------------------- 353
VP1 dNdC 1011CTL318 NIVTFV-------------------------------------------- 323

VP1 wildtype     380 VFPGN 384
VP1 dNdC 0000    297 ----- 296
VP1 dNdC 1011E7  354 ----- 353
VP1 dNdC 1011CTL324 ----- 323
```

A.

MTAQTPIHVYSEIGKLKKVLLHRPGKEIENLMPDYLERLLFDDIPFLEDAQKEHDAF
AQALRDEGIEVLYLETLAAESLVTPEIREAFIDEYLSEANIRGRATKKAIRELLMAIE
DNQELIEKTMAGVQKSELPEIPASEKGLTDLVESSYPFAIDPMPNLYFTRDPFATI
GTGVSLNHMFSETRNRETLYGKYIFTHHPIYGGGKVPMVYDRNETTRIEGGDELV
LSKDVLAVGISQRTDAASIEKLLVNIFKQNLGFKKVLAFEFANNRKFMHLDTVFTM
VDYDKFTIHPEIEGDLRVYSVTYDNEELHIVEEKGDLAELLAANLGVEKVDLIRCG
GDNLVAAGREQWNDGSNTLTIAPGVVVVYNRNTITNAILESKGLKLIKIHGSELVR
GRGGPRCMSMPFEREDI

B.

MSTSFENKATNRGVITFTISQDKIKPALDKAFNKIKKDLNAPGFRKGHMPRPVFNQ
KFGEEVLYEDALNIVLPEAYEAAVTELGLDVVAQPKIDVVSMEKGKEWTLSAEVV
TKPEVKLGDYKNLVVEVDASKEVSDEDVDAKIERERQNLAELIIKDGEAAQGDTV
VIDFVGSVDGVEFDGGKGDNFSLELGSGQFIPGFEDQLVGAKAGDEVEVNVTFP
ESYQAEDLAGKAAKFMTTIHEVKTKEVPELDDELAKDIDEDVDTLEDLKVKYRKEL
EAAQETAYDDAVEGAAIELAVANAEIVDLPEEMIHEEVNRSVNEFMGNMQRQGIS
PEMYFQLTGTTQEDLHNQYSAEADKRVKTNLVIEAIAKAEGFEATDSEIEQEINDL
ATEYNMPADQVRSLLSADMLKHDIAMKKAVEVITSTASVK

A.

MTAQTPIHVYSEIGKLKKVLLHRPGKEIENLMPDYLERLLFDDIPFLEDAQKEHDAFAQALRDEGIE
VLYLETLAAESLVTPEIREAFIDEYLSEANIRGRATKKAIRELLMAIEDNQELIEKTMAGVQKSELPEI
PASEKGLTDLVESNYPFAIDPMPNLYFTRDPFATIGTGVSLNHMFSETRNRETLYGKYIFTHHPIYG
GGKVPMVYDRNETTRIEGGDELVLSKDVLAVGISQRTDAASIEKLLVNIFKQNLGFKKVLAFEFANN
RKFMHLDTVFTMVDYDKFTIHPEIEGDLRVYSVTYDNEELHIVEEKGDLAELLAANLGVEKVDLIRC
GGDNLVAAGREQWNDGSNTLTIAPGVVVVYNRNTITNAILESKGLKLIKIHGSELVRGRGGPRCMS
MPFEREDIGSMLLIKGGMEVLDLVTGPDSVTEIEAFLNPRMGQPPTPESLTEGGQYYGWSRGINL
ATSAGTEDSPGNNTLPTWSMAKLQLPMLNEDLTCDTLQMWEAVSVKTEVVGSGSLLDVHGFNK
PTDTVNTKGISTPVEGSQYHVFAVGGEPLDLQGLVTDARTKYKEEGVVTIKTITKKDMVNKDQVLN
PISKAKLDKDGMYPVEIWHPDPAKNENTRYFGNYTGGTTTPPVLQFTNTLTTVLLDENGVGPLCK
GEGLYLSCVDIMGWRVTRSAYDVHHWRGLPRYFKITLRKRWVKNPYP

B.

MSTSFENKATNRGVITFTISQDKIKPALDKAFNKIKKDLNAPGFRKGHMPRPVFNQKFGEEVLYED
ALNIVLPEAYEAAVTELGLDVVAQPKIDVVSMEKGKEWTLSAEVVTKPEVKLGDYKNLVVEVDASK
EVSDEDVDAKIERERQNLAELIIKDGEAAQGDTVVIDFVGSVDGVEFDGGKGDNFSLELGSGQFIP
GFEDQLVGAKAGDEVEVNVTFPESYQAEDLAGKAAKFMTTIHEVKTKEVPELDDELAKDIDEDVD
TLEDLKVKYRKELEAAQETAYDDAVEGAAIELAVANAEIVDLPEEMIHEEVNRSVNEFMGNMQRQ
GISPEMYFQLTGTTQEDLHNQYSAEADKRVKTNLVIEAIAKAEGFEATDSEIEQEINDLATEYNMPA
DQVRSLLSADMLKHDIAMKKAVEVITSTASVKGSMLLIKGGMEVLDLVTGPDSVTEIEAFLNPRMG
QPPTPESLTEGGQYYGWSRGINLATSAGTEDSPGNNTLPTWSMAKLQLPMLNEDLTCDTLQMW
EAVSVKTEVVGSGSLLDVHGFNKPTDTVNTKGISTPVEGSQYHVFAVGGEPLDLQGLVTDARTKY
KEEGVVTIKTITKKDMVNKDQVLNPISKAKLDKDGMYPVEIWHPDPAKNENTRYFGNYTGGTTTPP
VLQFTNTLTTVLLDENGVGPLCKGEGLYLSCVDIMGWRVTRSAYDVHHWRGLPRYFKITLRKRW
VKNPYP

Figure 29

SEQUENCE LISTING

<160> NUMBER OF SEQ ID NOS: 49

<210> SEQ ID NO 1
<211> LENGTH: 384
<212> TYPE: PRT
<213> ORGANISM: Murine Polyomavirus

<400> SEQUENCE: 1

Met Ala Pro Lys Arg Lys Ser Gly Val Ser Lys Cys Glu Thr Lys Cys

-continued

```
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Asp Thr Glu Asp Ser Pro Gly Asn Asn Thr Leu
                85                  90                  95

Pro Thr Trp Ser Met Ala Lys Leu Gln Leu Pro Met Leu Asn Glu Asp
            100                 105                 110

Leu Thr Cys Asp Thr Leu Gln Met Trp Glu Ala Val Ser Val Lys Thr
        115                 120                 125

Glu Val Val Gly Ser Gly Ser Leu Leu Asp Val His Gly Phe Asn Lys
    130                 135                 140

Pro Thr Asp Thr Val Asn Thr Lys Gly Ile Ser Thr Pro Val Glu Gly
145                 150                 155                 160

Ser Gln Tyr His Val Phe Ala Val Gly Gly Glu Pro Leu Asp Leu Gln
                165                 170                 175

Gly Leu Val Thr Asp Ala Arg Thr Lys Tyr Lys Glu Glu Gly Val Val
            180                 185                 190

Thr Ile Lys Thr Ile Thr Lys Lys Asp Met Val Asn Lys Asp Gln Val
        195                 200                 205

Leu Asn Pro Ile Ser Lys Ala Lys Leu Asp Lys Asp Gly Met Tyr Pro
    210                 215                 220

Val Glu Ile Trp His Pro Asp Pro Ala Lys Asn Glu Asn Thr Arg Tyr
225                 230                 235                 240

Phe Gly Asn Tyr Thr Gly Gly Thr Thr Thr Pro Pro Val Leu Gln Phe
                245                 250                 255

Thr Asn Thr Leu Thr Thr Val Leu Leu Asp Glu Asn Gly Val Gly Pro
            260                 265                 270

Leu Cys Lys Gly Glu Gly Leu Tyr Leu Ser Cys Val Asp Ile Met Gly
        275                 280                 285

Trp Arg Val Thr Arg Asn Tyr Asp Val His His Trp Arg Gly Leu Pro
    290                 295                 300

Arg Tyr Phe Lys Ile Thr Leu Arg Lys Arg Trp Val Lys Asn Pro Tyr
305                 310                 315                 320

Pro Met Ala Ser Leu Ile Ser Ser Leu Phe Asn Asn Met Leu Pro Gln
                325                 330                 335

Val Gln Gly Gln Pro Met Glu Gly Glu Asn Thr Gln Val Glu Glu Val
            340                 345                 350

Arg Val Tyr Asp Gly Thr Glu Pro Val Pro Gly Asp Pro Asp Met Thr
        355                 360                 365

Arg Tyr Val Asp Arg Phe Gly Lys Thr Lys Thr Val Phe Pro Gly Asn
    370                 375                 380
```

<210> SEQ ID NO 2
<211> LENGTH: 385
<212> TYPE: PRT
<213> ORGANISM: Artificial Sequence
<220> FEATURE:
<223> OTHER INFORMATION: S1 of VP1 mutated to include NaeI restriction site -continued

<400> SEQUENCE: 2

```
Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Ala Gly Thr Glu Asp Ser Pro Gly Asn Asn Thr
                85                  90                  95

Leu Pro Thr Trp Ser Met Ala Lys Leu Gln Leu Pro Met Leu Asn Glu
            100                 105                 110

Asp Leu Thr Cys Asp Thr Leu Gln Met Trp Glu Ala Val Ser Val Lys
        115                 120                 125

Thr Glu Val Val Gly Ser Gly Ser Leu Leu Asp Val His Gly Phe Asn
    130                 135                 140

Lys Pro Thr Asp Thr Val Asn Thr Lys Gly Ile Ser Thr Pro Val Glu
145                 150                 155                 160

Gly Ser Gln Tyr His Val Phe Ala Val Gly Gly Glu Pro Leu Asp Leu
                165                 170                 175

Gln Gly Leu Val Thr Asp Ala Arg Thr Lys Tyr Lys Glu Glu Gly Val
            180                 185                 190

Val Thr Ile Lys Thr Ile Thr Lys Lys Asp Met Val Asn Lys Asp Gln
        195                 200                 205

Val Leu Asn Pro Ile Ser Lys Ala Lys Leu Asp Lys Asp Gly Met Tyr
    210                 215                 220

Pro Val Glu Ile Trp His Pro Asp Pro Ala Lys Asn Glu Asn Thr Arg
225                 230                 235                 240

Tyr Phe Gly Asn Tyr Thr Gly Gly Thr Thr Thr Pro Pro Val Leu Gln
                245                 250                 255

Phe Thr Asn Thr Leu Thr Thr Val Leu Leu Asp Glu Asn Gly Val Gly
            260                 265                 270

Pro Leu Cys Lys Gly Glu Gly Leu Tyr Leu Ser Cys Val Asp Ile Met
        275                 280                 285

Gly Trp Arg Val Thr Arg Asn Tyr Asp Val His His Trp Arg Gly Leu
    290                 295                 300

Pro Arg Tyr Phe Lys Ile Thr Leu Arg Lys Arg Trp Val Lys Asn Pro
305                 310                 315                 320

Tyr Pro Met Ala Ser Leu Ile Ser Ser Leu Phe Asn Asn Met Leu Pro
                325                 330                 335

Gln Val Gln Gly Gln Pro Met Glu Gly Glu Asn Thr Gln Val Glu Glu
            340                 345                 350

Val Arg Val Tyr Asp Gly Thr Glu Pro Val Pro Gly Asp Pro Asp Met
        355                 360                 365

Thr Arg Tyr Val Asp Arg Phe Gly Lys Thr Lys Thr Val Phe Pro Gly
    370                 375                 380

Asn
385
```

<210> SEQ ID NO 3
<211> LENGTH: 386
<212> TYPE: PRT
<213> ORGANISM: Artificial Sequence
<220> FEATURE:
<223> OTHER INFORMATION: S1 of VP1 mutated to include NaeI restriction site and S4 of VP1 mutated to include AfeI restriction site

<400> SEQUENCE: 3

```
Met Ala Pro Lys Arg Lys Ser Gly Val Ser Lys Cys Glu Thr Lys Cys
1               5                   10                  15

Thr Lys Ala Cys Pro Arg Pro Ala Pro Val Pro Lys Leu Leu Ile Lys
            20                  25                  30

Gly Gly Met Glu Val Leu Asp Leu Val Thr Gly Pro Asp Ser Val Thr
        35                  40                  45

Glu Ile Glu Ala Phe Leu Asn Pro Arg Met Gly Gln Pro Pro Thr Pro
    50                  55                  60

Glu Ser Leu Thr Glu Gly Gly Gln Tyr Tyr Gly Trp Ser Arg Gly Ile
65                  70                  75                  80

Asn Leu Ala Thr Ser Ala Gly Thr Glu Asp Ser Pro Gly Asn Asn Thr
                85                  90                  95

Leu Pro Thr Trp Ser Met Ala Lys Leu Gln Leu Pro Met Leu Asn Glu
            100                 105                 110

Asp Leu Thr Cys Asp Thr Leu Gln Met Trp Glu Ala Val Ser Val Lys
        115                 120                 125

Thr Glu Val Val Gly Ser Gly Ser Leu Leu Asp Val His Gly Phe Asn
    130                 135                 140

Lys Pro Thr Asp Thr Val Asn Thr Lys Gly Ile Ser Thr Pro Val Glu
145                 150                 155                 160

Gly Ser Gln Tyr His Val Phe Ala Val Gly Gly Glu Pro Leu Asp Leu
                165                 170                 175

Gln Gly Leu Val Thr Asp Ala Arg Thr Lys Tyr Lys Glu Glu Gly Val
            180                 185                 190

Val Thr Ile Lys Thr Ile Thr Lys Lys Asp Met Val Asn Lys Asp Gln
        195                 200                 205

Val Leu Asn Pro Ile Ser Lys Ala Lys Leu Asp Lys Asp Gly Met Tyr
    210                 215                 220

Pro Val Glu Ile Trp His Pro Asp Pro Ala Lys Asn Glu Asn Thr Arg
225                 230                 235                 240

Tyr Phe Gly Asn Tyr Thr Gly Gly Thr Thr Thr Pro Pro Val Leu Gln
                245                 250                 255

Phe Thr Asn Thr Leu Thr Thr Val Leu Leu Asp Glu Asn Gly Val Gly
            260                 265                 270

Pro Leu Cys Lys Gly Glu Gly Leu Tyr Leu Ser Cys Val Asp Ile Met
        275                 280                 285

Gly Trp Arg Val Thr Arg Ser Ala Tyr Asp Val His His Trp Arg Gly
    290                 295                 300

Leu Pro Arg Tyr Phe Lys Ile Thr Leu Arg Lys Arg Trp Val Lys Asn
305                 310                 315                 320

Pro Tyr Pro Met Ala Ser Leu Ile Ser Ser Leu Phe Asn Asn Met Leu
                325                 330                 335

Pro Gln Val Gln Gly Gln Pro Met Glu Gly Glu Asn Thr Gln Val Glu
            340                 345                 350

Glu Val Arg Val Tyr Asp Gly Thr Glu Pro Val Pro Gly Asp Pro Asp
        355                 360                 365
```

-continued

```
Met Thr Arg Tyr Val Asp Arg Phe Gly Lys Thr Lys Thr Val Phe Pro
    370                 375                 380

Gly Asn
385


<210> SEQ ID NO 4
<211> LENGTH: 295
<212> TYPE: PRT
<213> ORGANISM: Artificial Sequence
<220> FEATURE:
<223> OTHER INFORMATION: A delta N28 and delta C63 VP1 along with
      mutated S1 and S4 sites

<400> SEQUENCE: 4

Leu Leu Ile Lys Gly Gly Met Glu Val Leu Asp Leu Val Thr Gly Pro
1               5                   10                  15

Asp Ser Val Thr Glu Ile Glu Ala Phe Leu Asn Pro Arg Met Gly Gln
            20                  25                  30

Pro Pro Thr Pro Glu Ser Leu Thr Glu Gly Gly Gln Tyr Tyr Gly Trp
        35                  40                  45

Ser Arg Gly Ile Asn Leu Ala Thr Ser Ala Gly Thr Glu Asp Ser Pro
    50                  55                  60

Gly Asn Asn Thr Leu Pro Thr Trp Ser Met Ala Lys Leu Gln Leu Pro
65                  70                  75                  80

Met Leu Asn Glu Asp Leu Thr Cys Asp Thr Leu Gln Met Trp Glu Ala
                85                  90                  95

Val Ser Val Lys Thr Glu Val Val Gly Ser Gly Ser Leu Leu Asp Val
            100                 105                 110

His Gly Phe Asn Lys Pro Thr Asp Thr Val Asn Thr Lys Gly Ile Ser
        115                 120                 125

Thr Pro Val Glu Gly Ser Gln Tyr His Val Phe Ala Val Gly Gly Glu
    130                 135                 140

Pro Leu Asp Leu Gln Gly Leu Val Thr Asp Ala Arg Thr Lys Tyr Lys
145                 150                 155                 160

Glu Glu Gly Val Val Thr Ile Lys Thr Ile Thr Lys Lys Asp Met Val
                165                 170                 175

Asn Lys Asp Gln Val Leu Asn Pro Ile Ser Lys Ala Lys Leu Asp Lys
            180                 185                 190

Asp Gly Met Tyr Pro Val Glu Ile Trp His Pro Asp Pro Ala Lys Asn
        195                 200                 205

Glu Asn Thr Arg Tyr Phe Gly Asn Tyr Thr Gly Gly Thr Thr Thr Pro
    210                 215                 220

Pro Val Leu Gln Phe Thr Asn Thr Leu Thr Thr Val Leu Leu Asp Glu
225                 230                 235                 240

Asn Gly Val Gly Pro Leu Cys Lys Gly Glu Gly Leu Tyr Leu Ser Cys
                245                 250                 255

Val Asp Ile Met Gly Trp Arg Val Thr Arg Ser Ala Tyr Asp Val His
            260                 265                 270

His Trp Arg Gly Leu Pro Arg Tyr Phe Lys Ile Thr Leu Arg Lys Arg
        275                 280                 285

Trp Val Lys Asn Pro Tyr Pro
    290                 295


<210> SEQ ID NO 5
<211> LENGTH: 296
<212> TYPE: PRT
<213> ORGANISM: Artificial Sequence
```

-continued

<220> FEATURE:
<223> OTHER INFORMATION: Delta N28 and delta C63 VP1 with mutated S1 and S4 sites. Restriction site PmlI introduced at the N-terminus and restriction site SnaBI introduced at the C-terminus.

<400> SEQUENCE: 5

```
His Val Leu Ile Lys Gly Gly Met Glu Val Leu Asp Leu Val Thr Gly
1               5                   10                  15

Pro Asp Ser Val Thr Glu Ile Glu Ala Phe Leu Asn Pro Arg Met Gly
            20                  25                  30

Gln Pro Pro Thr Pro Glu Ser Leu Thr Glu Gly Gly Gln Tyr Tyr Gly
        35                  40                  45

Trp Ser Arg Gly Ile Asn Leu Ala Thr Ser Ala Gly Thr Glu Asp Ser
    50                  55                  60

Pro Gly Asn Asn Thr Leu Pro Thr Trp Ser Met Ala Lys Leu Gln Leu
65                  70                  75                  80

Pro Met Leu Asn Glu Asp Leu Thr Cys Asp Thr Leu Gln Met Trp Glu
                85                  90                  95

Ala Val Ser Val Lys Thr Glu Val Val Gly Ser Gly Ser Leu Leu Asp
            100                 105                 110

Val His Gly Phe Asn Lys Pro Thr Asp Thr Val Asn Thr Lys Gly Ile
        115                 120                 125

Ser Thr Pro Val Glu Gly Ser Gln Tyr His Val Phe Ala Val Gly Gly
    130                 135                 140

Glu Pro Leu Asp Leu Gln Gly Leu Val Thr Asp Ala Arg Thr Lys Tyr
145                 150                 155                 160

Lys Glu Glu Gly Val Val Thr Ile Lys Thr Ile Thr Lys Lys Asp Met
                165                 170                 175

Val Asn Lys Asp Gln Val Leu Asn Pro Ile Ser Lys Ala Lys Leu Asp
            180                 185                 190

Lys Asp Gly Met Tyr Pro Val Glu Ile Trp His Pro Asp Pro Ala Lys
        195                 200                 205

Asn Glu Asn Thr Arg Tyr Phe Gly Asn Tyr Thr Gly Gly Thr Thr Thr
    210                 215                 220

Pro Pro Val Leu Gln Phe Thr Asn Thr Leu Thr Thr Val Leu Leu Asp
225                 230                 235                 240

Glu Asn Gly Val Gly Pro Leu Cys Lys Gly Glu Gly Leu Tyr Leu Ser
                245                 250                 255

Cys Val Asp Ile Met Gly Trp Arg Val Thr Arg Ser Ala Tyr Asp Val
            260                 265                 270

His His Trp Arg Gly Leu Pro Arg Tyr Phe Lys Ile Thr Leu Arg Lys
        275                 280                 285

Arg Trp Val Lys Asn Pro Tyr Val
    290                 295
```

<210> SEQ ID NO 6
<211> LENGTH: 347
<212> TYPE: PRT
<213> ORGANISM: Artificial Sequence
<220> FEATURE:
<223> OTHER INFORMATION: VP1 with HA epitope from loop A of H1N1

<400> SEQUENCE: 6

```
His Asp Ser Asn Lys Gly Val Thr Ala Ala Cys Pro His Ala Gly Ala
1               5                   10                  15

Lys Ser Val Leu Ile Lys Gly Gly Met Glu Val Leu Asp Leu Val Thr
            20                  25                  30
```

```
Gly Pro Asp Ser Val Thr Glu Ile Glu Ala Phe Leu Asn Pro Arg Met
        35                  40                  45

Gly Gln Pro Pro Thr Pro Glu Ser Leu Thr Glu Gly Gly Gln Tyr Tyr
    50                  55                  60

Gly Trp Ser Arg Gly Ile Asn Leu Ala Thr Ser Ala Gly Thr Glu Asp
65                  70                  75                  80

Ser Pro Gly Asn Asn Thr Leu Pro Thr Trp Ser Met Ala Lys Leu Gln
                85                  90                  95

Leu Pro Met Leu Asn Glu Asp Leu Thr Cys Asp Thr Leu Gln Met Trp
            100                 105                 110

Glu Ala Val Ser Val Lys Thr Glu Val Val Gly Ser Gly Ser Leu Leu
        115                 120                 125

Asp Val His Gly Phe Asn Lys Pro Thr Asp Thr Val Asn Thr Lys Gly
    130                 135                 140

Ile Ser Thr Pro Val Glu Gly Ser Gln Tyr His Val Phe Ala Val Gly
145                 150                 155                 160

Gly Glu Pro Leu Asp Leu Gln Gly Leu Val Thr Asp Ala Arg Thr Lys
                165                 170                 175

Tyr Lys Glu Glu Gly Val Val Thr Ile Lys Thr Ile Thr Lys Lys Asp
            180                 185                 190

Met Val Asn Lys Asp Gln Val Leu Asn Pro Ile Ser Lys Ala Lys Leu
        195                 200                 205

Asp Lys Asp Gly Met Tyr Pro Val Glu Ile Trp His Pro Asp Pro Ala
    210                 215                 220

Lys Asn Glu Asn Thr Arg Tyr Phe Gly Asn Tyr Thr Gly Gly Thr Thr
225                 230                 235                 240

Thr Pro Pro Val Leu Gln Phe Thr Asn Thr Leu Thr Thr Val Leu Leu
                245                 250                 255

Asp Glu Asn Gly Val Gly Pro Leu Cys Lys Gly Glu Gly Leu Tyr Leu
            260                 265                 270

Ser Cys Val Asp Ile Met Gly Trp Arg Val Thr Arg Ser Asp Ser Asn
        275                 280                 285

Lys Gly Val Thr Ala Ala Cys Pro His Ala Gly Ala Lys Ser Ala Tyr
    290                 295                 300

Asp Val His His Trp Arg Gly Leu Pro Arg Tyr Phe Lys Ile Thr Leu
305                 310                 315                 320

Arg Lys Arg Trp Val Lys Asn Pro Tyr Asp Ser Asn Lys Gly Val Thr
                325                 330                 335

Ala Ala Cys Pro His Ala Gly Ala Lys Ser Val
            340                 345


<210> SEQ ID NO 7
<211> LENGTH: 365
<212> TYPE: PRT
<213> ORGANISM: Artificial Sequence
<220> FEATURE:
<223> OTHER INFORMATION: VP1 with the M2e insert

<400> SEQUENCE: 7

His Ser Leu Leu Thr Glu Val Glu Thr Pro Thr Arg Ser Glu Trp Glu
1               5                   10                  15

Cys Arg Cys Ser Asp Ser Ser Asp Val Leu Ile Lys Gly Gly Met Glu
            20                  25                  30

Val Leu Asp Leu Val Thr Gly Pro Asp Ser Val Thr Glu Ile Glu Ala
        35                  40                  45
```

```
Phe Leu Asn Pro Arg Met Gly Gln Pro Pro Thr Pro Glu Ser Leu Thr
    50                  55                  60

Glu Gly Gly Gln Tyr Tyr Gly Trp Ser Arg Gly Ile Asn Leu Ala Thr
65                  70                  75                  80

Ser Ala Gly Thr Glu Asp Ser Pro Gly Asn Asn Thr Leu Pro Thr Trp
                85                  90                  95

Ser Met Ala Lys Leu Gln Leu Pro Met Leu Asn Glu Asp Leu Thr Cys
            100                 105                 110

Asp Thr Leu Gln Met Trp Glu Ala Val Ser Val Lys Thr Glu Val Val
        115                 120                 125

Gly Ser Gly Ser Leu Leu Asp Val His Gly Phe Asn Lys Pro Thr Asp
    130                 135                 140

Thr Val Asn Thr Lys Gly Ile Ser Thr Pro Val Glu Gly Ser Gln Tyr
145                 150                 155                 160

His Val Phe Ala Val Gly Gly Glu Pro Leu Asp Leu Gln Gly Leu Val
                165                 170                 175

Thr Asp Ala Arg Thr Lys Tyr Lys Glu Glu Gly Val Val Thr Ile Lys
            180                 185                 190

Thr Ile Thr Lys Lys Asp Met Val Asn Lys Asp Gln Val Leu Asn Pro
        195                 200                 205

Ile Ser Lys Ala Lys Leu Asp Lys Asp Gly Met Tyr Pro Val Glu Ile
    210                 215                 220

Trp His Pro Asp Pro Ala Lys Asn Glu Asn Thr Arg Tyr Phe Gly Asn
225                 230                 235                 240

Tyr Thr Gly Gly Thr Thr Thr Pro Pro Val Leu Gln Phe Thr Asn Thr
                245                 250                 255

Leu Thr Thr Val Leu Leu Asp Glu Asn Gly Val Gly Pro Leu Cys Lys
            260                 265                 270

Gly Glu Gly Leu Tyr Leu Ser Cys Val Asp Ile Met Gly Trp Arg Val
        275                 280                 285

Thr Arg Ser Ser Leu Leu Thr Glu Val Glu Thr Pro Thr Arg Ser Glu
    290                 295                 300

Trp Glu Cys Arg Cys Ser Asp Ser Ser Asp Ala Tyr Asp Val His His
305                 310                 315                 320

Trp Arg Gly Leu Pro Arg Tyr Phe Lys Ile Thr Leu Arg Lys Arg Trp
                325                 330                 335

Val Lys Asn Pro Tyr Ser Leu Leu Thr Glu Val Glu Thr Pro Thr Arg
            340                 345                 350

Ser Glu Trp Glu Cys Arg Cys Ser Asp Ser Ser Asp Val
        355                 360                 365


<210> SEQ ID NO 8
<211> LENGTH: 434
<212> TYPE: PRT
<213> ORGANISM: Artificial Sequence
<220> FEATURE:
<223> OTHER INFORMATION: VP1 with M2e insert

<400> SEQUENCE: 8

His Ser Leu Leu Thr Glu Val Glu Thr Pro Thr Arg Ser Glu Trp Glu
1               5                   10                  15

Cys Arg Cys Ser Asp Ser Ser Asp Ser Leu Leu Thr Glu Val Glu Thr
            20                  25                  30

Pro Thr Arg Ser Glu Trp Glu Cys Arg Cys Ser Asp Ser Ser Asp Val
        35                  40                  45
```

-continued

```
Leu Ile Lys Gly Gly Met Glu Val Leu Asp Leu Val Thr Gly Pro Asp
    50                  55                  60

Ser Val Thr Glu Ile Glu Ala Phe Leu Asn Pro Arg Met Gly Gln Pro
65                  70                  75                  80

Pro Thr Pro Glu Ser Leu Thr Glu Gly Gly Gln Tyr Tyr Gly Trp Ser
                85                  90                  95

Arg Gly Ile Asn Leu Ala Thr Ser Ala Gly Thr Glu Asp Ser Pro Gly
            100                 105                 110

Asn Asn Thr Leu Pro Thr Trp Ser Met Ala Lys Leu Gln Leu Pro Met
        115                 120                 125

Leu Asn Glu Asp Leu Thr Cys Asp Thr Leu Gln Met Trp Glu Ala Val
    130                 135                 140

Ser Val Lys Thr Glu Val Val Gly Ser Gly Ser Leu Leu Asp Val His
145                 150                 155                 160

Gly Phe Asn Lys Pro Thr Asp Thr Val Asn Thr Lys Gly Ile Ser Thr
                165                 170                 175

Pro Val Glu Gly Ser Gln Tyr His Val Phe Ala Val Gly Gly Glu Pro
            180                 185                 190

Leu Asp Leu Gln Gly Leu Val Thr Asp Ala Arg Thr Lys Tyr Lys Glu
        195                 200                 205

Glu Gly Val Val Thr Ile Lys Thr Ile Thr Lys Lys Asp Met Val Asn
    210                 215                 220

Lys Asp Gln Val Leu Asn Pro Ile Ser Lys Ala Lys Leu Asp Lys Asp
225                 230                 235                 240

Gly Met Tyr Pro Val Glu Ile Trp His Pro Asp Pro Ala Lys Asn Glu
                245                 250                 255

Asn Thr Arg Tyr Phe Gly Asn Tyr Thr Gly Gly Thr Thr Thr Pro Pro
            260                 265                 270

Val Leu Gln Phe Thr Asn Thr Leu Thr Thr Val Leu Leu Asp Glu Asn
        275                 280                 285

Gly Val Gly Pro Leu Cys Lys Gly Glu Gly Leu Tyr Leu Ser Cys Val
    290                 295                 300

Asp Ile Met Gly Trp Arg Val Thr Arg Ser Ser Leu Leu Thr Glu Val
305                 310                 315                 320

Glu Thr Pro Thr Arg Ser Glu Trp Glu Cys Arg Cys Ser Asp Ser Ser
                325                 330                 335

Asp Ser Leu Leu Thr Glu Val Glu Thr Pro Thr Arg Ser Glu Trp Glu
            340                 345                 350

Cys Arg Cys Ser Asp Ser Ser Asp Ala Tyr Asp Val His His Trp Arg
        355                 360                 365

Gly Leu Pro Arg Tyr Phe Lys Ile Thr Leu Arg Lys Arg Trp Val Lys
    370                 375                 380

Asn Pro Tyr Ser Leu Leu Thr Glu Val Glu Thr Pro Thr Arg Ser Glu
385                 390                 395                 400

Trp Glu Cys Arg Cys Ser Asp Ser Ser Asp Ser Leu Leu Thr Glu Val
                405                 410                 415

Glu Thr Pro Thr Arg Ser Glu Trp Glu Cys Arg Cys Ser Asp Ser Ser
            420                 425                 430

Asp Val
```

<210> SEQ ID NO 9
<211> LENGTH: 335
<212> TYPE: PRT

```
<213> ORGANISM: Artificial Sequence
<220> FEATURE:
<223> OTHER INFORMATION: Amino acid sequence of VP1 dNdC 0000 with
      inserted peptides from Hendra Virus antigenic sequences

<400> SEQUENCE: 9

His Gly Leu Pro Asn Gln Ile Met Leu Gln Lys Thr Thr Ser Val Leu
1               5                   10                  15

Ile Lys Gly Gly Met Glu Val Leu Asp Leu Val Thr Gly Pro Asp Ser
            20                  25                  30

Val Thr Glu Ile Glu Ala Phe Leu Asn Pro Arg Met Gly Gln Pro Pro
        35                  40                  45

Thr Pro Glu Ser Leu Thr Glu Gly Gly Gln Tyr Tyr Gly Trp Ser Arg
    50                  55                  60

Gly Ile Asn Leu Ala Thr Ser Ala Gly Thr Glu Asp Ser Pro Gly Asn
65                  70                  75                  80

Asn Thr Leu Pro Thr Trp Ser Met Ala Lys Leu Gln Leu Pro Met Leu
                85                  90                  95

Asn Glu Asp Leu Thr Cys Asp Thr Leu Gln Met Trp Glu Ala Val Ser
            100                 105                 110

Val Lys Thr Glu Val Val Gly Ser Gly Ser Leu Leu Asp Val His Gly
        115                 120                 125

Phe Asn Lys Pro Thr Asp Thr Val Asn Thr Lys Gly Ile Ser Thr Pro
    130                 135                 140

Val Glu Gly Ser Gln Tyr His Val Phe Ala Val Gly Gly Glu Pro Leu
145                 150                 155                 160

Asp Leu Gln Gly Leu Val Thr Asp Ala Arg Thr Lys Tyr Lys Glu Glu
                165                 170                 175

Gly Val Val Thr Ile Lys Thr Ile Thr Lys Lys Asp Met Val Asn Lys
            180                 185                 190

Asp Gln Val Leu Asn Pro Ile Ser Lys Ala Lys Leu Asp Lys Asp Gly
        195                 200                 205

Met Tyr Pro Val Glu Ile Trp His Pro Asp Pro Ala Lys Asn Glu Asn
    210                 215                 220

Thr Arg Tyr Phe Gly Asn Tyr Thr Gly Gly Thr Thr Thr Pro Pro Val
225                 230                 235                 240

Leu Gln Phe Thr Asn Thr Leu Thr Thr Val Leu Leu Asp Glu Asn Gly
                245                 250                 255

Val Gly Pro Leu Cys Lys Gly Glu Gly Leu Tyr Leu Ser Cys Val Asp
            260                 265                 270

Ile Met Gly Trp Arg Val Thr Arg Ser Gly Leu Pro Asn Gln Ile Met
        275                 280                 285

Leu Gln Lys Thr Thr Ser Ala Tyr Asp Val His His Trp Arg Gly Leu
    290                 295                 300

Pro Arg Tyr Phe Lys Ile Thr Leu Arg Lys Arg Trp Val Lys Asn Pro
305                 310                 315                 320

Tyr Gly Leu Pro Asn Gln Ile Met Leu Gln Lys Thr Thr Ser Val
                325                 330                 335


<210> SEQ ID NO 10
<211> LENGTH: 329
<212> TYPE: PRT
<213> ORGANISM: Artificial Sequence
<220> FEATURE:
<223> OTHER INFORMATION: Amino acid sequence of VP1 dNdC 0000 with
      inserted peptides from Hendra Virus antigenic sequences
```

<400> SEQUENCE: 10

His Val Arg Pro Lys Ser Asp Ser Gly Asp Tyr Asn Val Leu Ile Lys
1 5 10 15

Gly Gly Met Glu Val Leu Asp Leu Val Thr Gly Pro Asp Ser Val Thr
20 25 30

Glu Ile Glu Ala Phe Leu Asn Pro Arg Met Gly Gln Pro Pro Thr Pro
35 40 45

Glu Ser Leu Thr Glu Gly Gly Gln Tyr Tyr Gly Trp Ser Arg Gly Ile
50 55 60

Asn Leu Ala Thr Ser Ala Gly Thr Glu Asp Ser Pro Gly Asn Asn Thr
65 70 75 80

Leu Pro Thr Trp Ser Met Ala Lys Leu Gln Leu Pro Met Leu Asn Glu
85 90 95

Asp Leu Thr Cys Asp Thr Leu Gln Met Trp Glu Ala Val Ser Val Lys
100 105 110

Thr Glu Val Val Gly Ser Gly Ser Leu Leu Asp Val His Gly Phe Asn
115 120 125

Lys Pro Thr Asp Thr Val Asn Thr Lys Gly Ile Ser Thr Pro Val Glu
130 135 140

Gly Ser Gln Tyr His Val Phe Ala Val Gly Gly Glu Pro Leu Asp Leu
145 150 155 160

Gln Gly Leu Val Thr Asp Ala Arg Thr Lys Tyr Lys Glu Glu Gly Val
165 170 175

Val Thr Ile Lys Thr Ile Thr Lys Lys Asp Met Val Asn Lys Asp Gln
180 185 190

Val Leu Asn Pro Ile Ser Lys Ala Lys Leu Asp Lys Asp Gly Met Tyr
195 200 205

Pro Val Glu Ile Trp His Pro Asp Pro Ala Lys Asn Glu Asn Thr Arg
210 215 220

Tyr Phe Gly Asn Tyr Thr Gly Gly Thr Thr Thr Pro Pro Val Leu Gln
225 230 235 240

Phe Thr Asn Thr Leu Thr Thr Val Leu Leu Asp Glu Asn Gly Val Gly
245 250 255

Pro Leu Cys Lys Gly Glu Gly Leu Tyr Leu Ser Cys Val Asp Ile Met
260 265 270

Gly Trp Arg Val Thr Arg Ser Val Arg Pro Lys Ser Asp Ser Gly Asp
275 280 285

Tyr Asn Ala Tyr Asp Val His His Trp Arg Gly Leu Pro Arg Tyr Phe
290 295 300

Lys Ile Thr Leu Arg Lys Arg Trp Val Lys Asn Pro Tyr Val Arg Pro
305 310 315 320

Lys Ser Asp Ser Gly Asp Tyr Asn Val
325

<210> SEQ ID NO 11
<211> LENGTH: 329
<212> TYPE: PRT
<213> ORGANISM: Artificial Sequence
<220> FEATURE:
<223> OTHER INFORMATION: Amino acid sequence of VP1 dNdC 0000 with inserted peptides from Hendra Virus antigenic sequences

<400> SEQUENCE: 11

His Pro Ile Ile His Ser Lys Tyr Ser Lys Ala Glu Val Leu Ile Lys
1 5 10 15

```
Gly Gly Met Glu Val Leu Asp Leu Val Thr Gly Pro Asp Ser Val Thr
            20                  25                  30

Glu Ile Glu Ala Phe Leu Asn Pro Arg Met Gly Gln Pro Pro Thr Pro
        35                  40                  45

Glu Ser Leu Thr Glu Gly Gly Gln Tyr Tyr Gly Trp Ser Arg Gly Ile
    50                  55                  60

Asn Leu Ala Thr Ser Ala Gly Thr Glu Asp Ser Pro Gly Asn Asn Thr
65                  70                  75                  80

Leu Pro Thr Trp Ser Met Ala Lys Leu Gln Leu Pro Met Leu Asn Glu
                85                  90                  95

Asp Leu Thr Cys Asp Thr Leu Gln Met Trp Glu Ala Val Ser Val Lys
            100                 105                 110

Thr Glu Val Val Gly Ser Gly Ser Leu Leu Asp Val His Gly Phe Asn
        115                 120                 125

Lys Pro Thr Asp Thr Val Asn Thr Lys Gly Ile Ser Thr Pro Val Glu
    130                 135                 140

Gly Ser Gln Tyr His Val Phe Ala Val Gly Gly Glu Pro Leu Asp Leu
145                 150                 155                 160

Gln Gly Leu Val Thr Asp Ala Arg Thr Lys Tyr Lys Glu Glu Gly Val
                165                 170                 175

Val Thr Ile Lys Thr Ile Thr Lys Lys Asp Met Val Asn Lys Asp Gln
            180                 185                 190

Val Leu Asn Pro Ile Ser Lys Ala Lys Leu Asp Lys Asp Gly Met Tyr
        195                 200                 205

Pro Val Glu Ile Trp His Pro Asp Pro Ala Lys Asn Glu Asn Thr Arg
    210                 215                 220

Tyr Phe Gly Asn Tyr Thr Gly Gly Thr Thr Thr Pro Pro Val Leu Gln
225                 230                 235                 240

Phe Thr Asn Thr Leu Thr Thr Val Leu Leu Asp Glu Asn Gly Val Gly
                245                 250                 255

Pro Leu Cys Lys Gly Glu Gly Leu Tyr Leu Ser Cys Val Asp Ile Met
            260                 265                 270

Gly Trp Arg Val Thr Arg Ser Pro Ile Ile His Ser Lys Tyr Ser Lys
        275                 280                 285

Ala Glu Ala Tyr Asp Val His His Trp Arg Gly Leu Pro Arg Tyr Phe
    290                 295                 300

Lys Ile Thr Leu Arg Lys Arg Trp Val Lys Asn Pro Tyr Pro Ile Ile
305                 310                 315                 320

His Ser Lys Tyr Ser Lys Ala Glu Val
                325
```

```
<210> SEQ ID NO 12
<211> LENGTH: 341
<212> TYPE: PRT
<213> ORGANISM: Artificial Sequence
<220> FEATURE:
<223> OTHER INFORMATION: Amino acid sequence of VP1 dNdC 0000 with
      inserted peptides from Hendra Virus antigenic sequences

<400> SEQUENCE: 12

His Val Glu Ile Tyr Asp Thr Gly Asp Ser Val Ile Arg Pro Lys Leu
1               5                   10                  15

Val Leu Ile Lys Gly Gly Met Glu Val Leu Asp Leu Val Thr Gly Pro
            20                  25                  30

Asp Ser Val Thr Glu Ile Glu Ala Phe Leu Asn Pro Arg Met Gly Gln
        35                  40                  45
```

```
Pro Pro Thr Pro Glu Ser Leu Thr Glu Gly Gly Gln Tyr Tyr Gly Trp
    50                  55                  60

Ser Arg Gly Ile Asn Leu Ala Thr Ser Ala Gly Thr Glu Asp Ser Pro
65                  70                  75                  80

Gly Asn Asn Thr Leu Pro Thr Trp Ser Met Ala Lys Leu Gln Leu Pro
                85                  90                  95

Met Leu Asn Glu Asp Leu Thr Cys Asp Thr Leu Gln Met Trp Glu Ala
            100                 105                 110

Val Ser Val Lys Thr Glu Val Val Gly Ser Gly Ser Leu Leu Asp Val
        115                 120                 125

His Gly Phe Asn Lys Pro Thr Asp Thr Val Asn Thr Lys Gly Ile Ser
    130                 135                 140

Thr Pro Val Glu Gly Ser Gln Tyr His Val Phe Ala Val Gly Gly Glu
145                 150                 155                 160

Pro Leu Asp Leu Gln Gly Leu Val Thr Asp Ala Arg Thr Lys Tyr Lys
                165                 170                 175

Glu Glu Gly Val Val Thr Ile Lys Thr Ile Thr Lys Lys Asp Met Val
            180                 185                 190

Asn Lys Asp Gln Val Leu Asn Pro Ile Ser Lys Ala Lys Leu Asp Lys
        195                 200                 205

Asp Gly Met Tyr Pro Val Glu Ile Trp His Pro Asp Pro Ala Lys Asn
    210                 215                 220

Glu Asn Thr Arg Tyr Phe Gly Asn Tyr Thr Gly Gly Thr Thr Thr Pro
225                 230                 235                 240

Pro Val Leu Gln Phe Thr Asn Thr Leu Thr Thr Val Leu Leu Asp Glu
                245                 250                 255

Asn Gly Val Gly Pro Leu Cys Lys Gly Glu Gly Leu Tyr Leu Ser Cys
            260                 265                 270

Val Asp Ile Met Gly Trp Arg Val Thr Arg Ser Val Glu Ile Tyr Asp
        275                 280                 285

Thr Gly Asp Ser Val Ile Arg Pro Lys Leu Ala Tyr Asp Val His His
    290                 295                 300

Trp Arg Gly Leu Pro Arg Tyr Phe Lys Ile Thr Leu Arg Lys Arg Trp
305                 310                 315                 320

Val Lys Asn Pro Tyr Val Glu Ile Tyr Asp Thr Gly Asp Ser Val Ile
     325                 330                 335

Arg Pro Lys Leu Val
    340


<210> SEQ ID NO 13
<211> LENGTH: 338
<212> TYPE: PRT
<213> ORGANISM: Artificial Sequence
<220> FEATURE:
<223> OTHER INFORMATION: Amino acid sequence of VP1 dNdC 0000 with
      inserted peptides from Hendra Virus antigenic sequences

<400> SEQUENCE: 13

His Leu Glu Lys Ile Gly Ser Cys Thr Arg Gly Ile Ala Lys Gln Val
1               5                   10                  15

Leu Ile Lys Gly Gly Met Glu Val Leu Asp Leu Val Thr Gly Pro Asp
            20                  25                  30

Ser Val Thr Glu Ile Glu Ala Phe Leu Asn Pro Arg Met Gly Gln Pro
        35                  40                  45

Pro Thr Pro Glu Ser Leu Thr Glu Gly Gly Gln Tyr Tyr Gly Trp Ser
```

```
    50                  55                  60

Arg Gly Ile Asn Leu Ala Thr Ser Ala Gly Thr Glu Asp Ser Pro Gly
65                  70                  75                  80

Asn Asn Thr Leu Pro Thr Trp Ser Met Ala Lys Leu Gln Leu Pro Met
                85                  90                  95

Leu Asn Glu Asp Leu Thr Cys Asp Thr Leu Gln Met Trp Glu Ala Val
            100                 105                 110

Ser Val Lys Thr Glu Val Val Gly Ser Gly Ser Leu Leu Asp Val His
        115                 120                 125

Gly Phe Asn Lys Pro Thr Asp Thr Val Asn Thr Lys Gly Ile Ser Thr
    130                 135                 140

Pro Val Glu Gly Ser Gln Tyr His Val Phe Ala Val Gly Gly Glu Pro
145                 150                 155                 160

Leu Asp Leu Gln Gly Leu Val Thr Asp Ala Arg Thr Lys Tyr Lys Glu
                165                 170                 175

Glu Gly Val Val Thr Ile Lys Thr Ile Thr Lys Lys Asp Met Val Asn
            180                 185                 190

Lys Asp Gln Val Leu Asn Pro Ile Ser Lys Ala Lys Leu Asp Lys Asp
        195                 200                 205

Gly Met Tyr Pro Val Glu Ile Trp His Pro Asp Pro Ala Lys Asn Glu
    210                 215                 220

Asn Thr Arg Tyr Phe Gly Asn Tyr Thr Gly Gly Thr Thr Thr Pro Pro
225                 230                 235                 240

Val Leu Gln Phe Thr Asn Thr Leu Thr Thr Val Leu Leu Asp Glu Asn
                245                 250                 255

Gly Val Gly Pro Leu Cys Lys Gly Glu Gly Leu Tyr Leu Ser Cys Val
            260                 265                 270

Asp Ile Met Gly Trp Arg Val Thr Arg Ser Leu Glu Lys Ile Gly Ser
        275                 280                 285

Cys Thr Arg Gly Ile Ala Lys Gln Ala Tyr Asp Val His His Trp Arg
    290                 295                 300

Gly Leu Pro Arg Tyr Phe Lys Ile Thr Leu Arg Lys Arg Trp Val Lys
305                 310                 315                 320

Asn Pro Tyr Leu Glu Lys Ile Gly Ser Cys Thr Arg Gly Ile Ala Lys
                325                 330                 335

Gln Val


<210> SEQ ID NO 14
<211> LENGTH: 380
<212> TYPE: PRT
<213> ORGANISM: Artificial Sequence
<220> FEATURE:
<223> OTHER INFORMATION: VP1 dNdC 0000 with inserted peptides from GAS
      antigenic sequences

<400> SEQUENCE: 14

His Asn Ser Lys Thr Pro Ala Pro Ala Pro Ala Val Pro Val Lys Lys
1               5                   10                  15

Glu Ala Thr Lys Ser Lys Leu Ser Glu Ala Glu Leu His Val Leu Ile
            20                  25                  30

Lys Gly Gly Met Glu Val Leu Asp Leu Val Thr Gly Pro Asp Ser Val
        35                  40                  45

Thr Glu Ile Glu Ala Phe Leu Asn Pro Arg Met Gly Gln Pro Pro Thr
    50                  55                  60

Pro Glu Ser Leu Thr Glu Gly Gly Gln Tyr Tyr Gly Trp Ser Arg Gly
```

-continued

```
65                  70                  75                  80

Ile Asn Leu Ala Thr Ser Ala Gly Thr Glu Asp Ser Pro Gly Asn Asn
                85                  90                  95

Thr Leu Pro Thr Trp Ser Met Ala Lys Leu Gln Leu Pro Met Leu Asn
            100                 105                 110

Glu Asp Leu Thr Cys Asp Thr Leu Gln Met Trp Glu Ala Val Ser Val
        115                 120                 125

Lys Thr Glu Val Val Gly Ser Gly Ser Leu Leu Asp Val His Gly Phe
    130                 135                 140

Asn Lys Pro Thr Asp Thr Val Asn Thr Lys Gly Ile Ser Thr Pro Val
145                 150                 155                 160

Glu Gly Ser Gln Tyr His Val Phe Ala Val Gly Gly Glu Pro Leu Asp
                165                 170                 175

Leu Gln Gly Leu Val Thr Asp Ala Arg Thr Lys Tyr Lys Glu Glu Gly
            180                 185                 190

Val Val Thr Ile Lys Thr Ile Thr Lys Lys Asp Met Val Asn Lys Asp
        195                 200                 205

Gln Val Leu Asn Pro Ile Ser Lys Ala Lys Leu Asp Lys Asp Gly Met
    210                 215                 220

Tyr Pro Val Glu Ile Trp His Pro Asp Pro Ala Lys Asn Glu Asn Thr
225                 230                 235                 240

Arg Tyr Phe Gly Asn Tyr Thr Gly Gly Thr Thr Thr Pro Pro Val Leu
                245                 250                 255

Gln Phe Thr Asn Thr Leu Thr Thr Val Leu Leu Asp Glu Asn Gly Val
            260                 265                 270

Gly Pro Leu Cys Lys Gly Glu Gly Leu Tyr Leu Ser Cys Val Asp Ile
        275                 280                 285

Met Gly Trp Arg Val Thr Arg Ser Asn Ser Lys Thr Pro Ala Pro Ala
    290                 295                 300

Pro Ala Val Pro Val Lys Lys Glu Ala Thr Lys Ser Lys Leu Ser Glu
305                 310                 315                 320

Ala Glu Leu His Ala Tyr Asp Val His His Trp Arg Gly Leu Pro Arg
                325                 330                 335

Tyr Phe Lys Ile Thr Leu Arg Lys Arg Trp Val Lys Asn Pro Tyr Asn
            340                 345                 350

Ser Lys Thr Pro Ala Pro Ala Pro Ala Val Pro Val Lys Lys Glu Ala
        355                 360                 365

Thr Lys Ser Lys Leu Ser Glu Ala Glu Leu His Val
    370                 375                 380
```

<210> SEQ ID NO 15
<211> LENGTH: 353
<212> TYPE: PRT
<213> ORGANISM: Artificial Sequence
<220> FEATURE:
<223> OTHER INFORMATION: VP1 dNdC 0000 with inserted peptides from GAS antigenic sequences

<400> SEQUENCE: 15

```
His Asn Ser Lys Asn Pro Val Pro Val Lys Lys Glu Ala Lys Leu Ser
1               5                   10                  15

Glu Ala Glu Leu Val Leu Ile Lys Gly Gly Met Glu Val Leu Asp Leu
            20                  25                  30

Val Thr Gly Pro Asp Ser Val Thr Glu Ile Glu Ala Phe Leu Asn Pro
        35                  40                  45
```

```
Arg Met Gly Gln Pro Pro Thr Pro Glu Ser Leu Thr Glu Gly Gly Gln
    50                  55                  60

Tyr Tyr Gly Trp Ser Arg Gly Ile Asn Leu Ala Thr Ser Ala Gly Thr
65                  70                  75                  80

Glu Asp Ser Pro Gly Asn Asn Thr Leu Pro Thr Trp Ser Met Ala Lys
                85                  90                  95

Leu Gln Leu Pro Met Leu Asn Glu Asp Leu Thr Cys Asp Thr Leu Gln
            100                 105                 110

Met Trp Glu Ala Val Ser Val Lys Thr Glu Val Val Gly Ser Gly Ser
        115                 120                 125

Leu Leu Asp Val His Gly Phe Asn Lys Pro Thr Asp Thr Val Asn Thr
    130                 135                 140

Lys Gly Ile Ser Thr Pro Val Glu Gly Ser Gln Tyr His Val Phe Ala
145                 150                 155                 160

Val Gly Gly Glu Pro Leu Asp Leu Gln Gly Leu Val Thr Asp Ala Arg
                165                 170                 175

Thr Lys Tyr Lys Glu Glu Gly Val Val Thr Ile Lys Thr Ile Thr Lys
            180                 185                 190

Lys Asp Met Val Asn Lys Asp Gln Val Leu Asn Pro Ile Ser Lys Ala
        195                 200                 205

Lys Leu Asp Lys Asp Gly Met Tyr Pro Val Glu Ile Trp His Pro Asp
    210                 215                 220

Pro Ala Lys Asn Glu Asn Thr Arg Tyr Phe Gly Asn Tyr Thr Gly Gly
225                 230                 235                 240

Thr Thr Thr Pro Pro Val Leu Gln Phe Thr Asn Thr Leu Thr Thr Val
                245                 250                 255

Leu Leu Asp Glu Asn Gly Val Gly Pro Leu Cys Lys Gly Glu Gly Leu
            260                 265                 270

Tyr Leu Ser Cys Val Asp Ile Met Gly Trp Arg Val Thr Arg Ser Asn
        275                 280                 285

Ser Lys Asn Pro Val Pro Val Lys Lys Glu Ala Lys Leu Ser Glu Ala
    290                 295                 300

Glu Leu Ala Tyr Asp Val His His Trp Arg Gly Leu Pro Arg Tyr Phe
305                 310                 315                 320

Lys Ile Thr Leu Arg Lys Arg Trp Val Lys Asn Pro Tyr Asn Ser Lys
                325                 330                 335

Asn Pro Val Pro Val Lys Lys Glu Ala Lys Leu Ser Glu Ala Glu Leu
            340                 345                 350

Val
```

<210> SEQ ID NO 16
<211> LENGTH: 356
<212> TYPE: PRT
<213> ORGANISM: Artificial Sequence
<220> FEATURE:
<223> OTHER INFORMATION: VP1 dNdC 0000 with inserted peptides from GAS
antigenic sequences

<400> SEQUENCE: 16

```
His Leu Lys Met Leu Asn Arg Asp Leu Glu Gln Ala Tyr Asn Glu Leu
1               5                   10                  15

Ser Gly Glu Ala His Val Leu Ile Lys Gly Gly Met Glu Val Leu Asp
            20                  25                  30

Leu Val Thr Gly Pro Asp Ser Val Thr Glu Ile Glu Ala Phe Leu Asn
        35                  40                  45
```

-continued

```
Pro Arg Met Gly Gln Pro Pro Thr Pro Glu Ser Leu Thr Glu Gly Gly
    50                  55                  60

Gln Tyr Tyr Gly Trp Ser Arg Gly Ile Asn Leu Ala Thr Ser Ala Gly
65                  70                  75                  80

Thr Glu Asp Ser Pro Gly Asn Asn Thr Leu Pro Thr Trp Ser Met Ala
                85                  90                  95

Lys Leu Gln Leu Pro Met Leu Asn Glu Asp Leu Thr Cys Asp Thr Leu
            100                 105                 110

Gln Met Trp Glu Ala Val Ser Val Lys Thr Glu Val Val Gly Ser Gly
        115                 120                 125

Ser Leu Leu Asp Val His Gly Phe Asn Lys Pro Thr Asp Thr Val Asn
    130                 135                 140

Thr Lys Gly Ile Ser Thr Pro Val Glu Gly Ser Gln Tyr His Val Phe
145                 150                 155                 160

Ala Val Gly Gly Glu Pro Leu Asp Leu Gln Gly Leu Val Thr Asp Ala
                165                 170                 175

Arg Thr Lys Tyr Lys Glu Glu Gly Val Val Thr Ile Lys Thr Ile Thr
            180                 185                 190

Lys Lys Asp Met Val Asn Lys Asp Gln Val Leu Asn Pro Ile Ser Lys
        195                 200                 205

Ala Lys Leu Asp Lys Asp Gly Met Tyr Pro Val Glu Ile Trp His Pro
    210                 215                 220

Asp Pro Ala Lys Asn Glu Asn Thr Arg Tyr Phe Gly Asn Tyr Thr Gly
225                 230                 235                 240

Gly Thr Thr Thr Pro Pro Val Leu Gln Phe Thr Asn Thr Leu Thr Thr
                245                 250                 255

Val Leu Leu Asp Glu Asn Gly Val Gly Pro Leu Cys Lys Gly Glu Gly
            260                 265                 270

Leu Tyr Leu Ser Cys Val Asp Ile Met Gly Trp Arg Val Thr Arg Ser
        275                 280                 285

Leu Lys Met Leu Asn Arg Asp Leu Glu Gln Ala Tyr Asn Glu Leu Ser
    290                 295                 300

Gly Glu Ala His Ala Tyr Asp Val His His Trp Arg Gly Leu Pro Arg
305                 310                 315                 320

Tyr Phe Lys Ile Thr Leu Arg Lys Arg Trp Val Lys Asn Pro Tyr Leu
                325                 330                 335

Lys Met Leu Asn Arg Asp Leu Glu Gln Ala Tyr Asn Glu Leu Ser Gly
            340                 345                 350

Glu Ala His Val
        355


<210> SEQ ID NO 17
<211> LENGTH: 419
<212> TYPE: PRT
<213> ORGANISM: Artificial Sequence
<220> FEATURE:
<223> OTHER INFORMATION: Chimeric VP1 with inserted peptide M2e epitope A

<400> SEQUENCE: 17

Ser Leu Leu Thr Glu Val Glu Thr Pro Thr Arg Asn Glu Trp Glu Cys
1               5                   10                  15

Arg Cys Ser Asp Ser Ser Asp Gly Ser Gly Gly Met Ala Pro Lys Arg
            20                  25                  30

Lys Ser Gly Val Ser Lys Cys Glu Thr Lys Cys Thr Lys Ala Cys Pro
        35                  40                  45
```

-continued

```
Arg Pro Ala Pro Val Pro Lys Leu Leu Ile Lys Gly Gly Met Glu Val
    50                  55                  60

Leu Asp Leu Val Thr Gly Pro Asp Ser Val Thr Glu Ile Glu Ala Phe
65                  70                  75                  80

Leu Asn Pro Arg Met Gly Gln Pro Pro Thr Pro Glu Ser Leu Thr Glu
                85                  90                  95

Gly Gly Gln Tyr Tyr Gly Trp Ser Arg Gly Ile Asn Leu Ala Thr Ser
            100                 105                 110

Ala Pro Tyr Asn Gly Lys Ser Ser Gly Thr Glu Asp Ser Pro Gly Asn
        115                 120                 125

Asn Thr Leu Pro Thr Trp Ser Met Ala Lys Leu Gln Leu Pro Met Leu
    130                 135                 140

Asn Glu Asp Leu Thr Cys Asp Thr Leu Gln Met Trp Glu Ala Val Ser
145                 150                 155                 160

Val Lys Thr Glu Val Val Gly Ser Gly Ser Leu Leu Asp Val His Gly
                165                 170                 175

Phe Asn Lys Pro Thr Asp Thr Val Asn Thr Lys Gly Ile Ser Thr Pro
            180                 185                 190

Val Glu Gly Ser Gln Tyr His Val Phe Ala Val Gly Gly Glu Pro Leu
        195                 200                 205

Asp Leu Gln Gly Leu Val Thr Asp Ala Arg Thr Lys Tyr Lys Glu Glu
    210                 215                 220

Gly Val Val Thr Ile Lys Thr Ile Thr Lys Lys Asp Met Val Asn Lys
225                 230                 235                 240

Asp Gln Val Leu Asn Pro Ile Ser Lys Ala Lys Leu Asp Lys Asp Gly
                245                 250                 255

Met Tyr Pro Val Glu Ile Trp His Pro Asp Pro Ala Lys Asn Glu Asn
            260                 265                 270

Thr Arg Tyr Phe Gly Asn Tyr Thr Gly Gly Thr Thr Thr Pro Pro Val
        275                 280                 285

Leu Gln Phe Thr Asn Thr Leu Thr Thr Val Leu Leu Asp Glu Asn Gly
    290                 295                 300

Val Gly Pro Leu Cys Lys Gly Glu Gly Leu Tyr Leu Ser Cys Val Asp
305                 310                 315                 320

Ile Met Gly Trp Arg Val Thr Arg Asn Tyr Asp Val His His Trp Arg
                325                 330                 335

Gly Leu Pro Arg Tyr Phe Lys Ile Thr Leu Arg Lys Arg Trp Val Lys
            340                 345                 350

Asn Pro Tyr Pro Met Ala Ser Leu Ile Ser Ser Leu Phe Asn Asn Met
        355                 360                 365

Leu Pro Gln Val Gln Gly Gln Pro Met Glu Gly Glu Asn Thr Gln Val
    370                 375                 380

Glu Glu Val Arg Val Tyr Asp Gly Thr Glu Pro Val Pro Gly Asp Pro
385                 390                 395                 400

Asp Met Thr Arg Tyr Val Asp Arg Phe Gly Lys Thr Lys Thr Val Phe
                405                 410                 415

Pro Gly Asn
```

<210> SEQ ID NO 18
<211> LENGTH: 437
<212> TYPE: PRT
<213> ORGANISM: Artificial Sequence
<220> FEATURE:
<223> OTHER INFORMATION: Chimeric VP1 with inserted peptide M2e epitopes
      A and B -continued

<400> SEQUENCE: 18

```
Ser Leu Leu Thr Glu Val Glu Thr Pro Thr Arg Asn Glu Trp Glu Cys
1               5                   10                  15

Arg Cys Ser Asp Ser Ser Asp Gly Ser Gly Gly Met Ala Pro Lys Arg
            20                  25                  30

Lys Ser Gly Val Ser Lys Cys Glu Thr Lys Cys Thr Lys Ala Cys Pro
        35                  40                  45

Arg Pro Ala Pro Val Pro Lys Leu Leu Ile Lys Gly Gly Met Glu Val
    50                  55                  60

Leu Asp Leu Val Thr Gly Pro Asp Ser Val Thr Glu Ile Glu Ala Phe
65                  70                  75                  80

Leu Asn Pro Arg Met Gly Gln Pro Pro Thr Pro Glu Ser Leu Thr Glu
                85                  90                  95

Gly Gly Gln Tyr Tyr Gly Trp Ser Arg Gly Ile Asn Leu Ala Thr Ser
            100                 105                 110

Ala Gly Asn Asp Ala Ala Glu Gln Thr Lys Leu Tyr Gln Asn Pro Thr
        115                 120                 125

Thr Tyr Gly Thr Glu Asp Ser Pro Gly Asn Asn Thr Leu Pro Thr Trp
    130                 135                 140

Ser Met Ala Lys Leu Gln Leu Pro Met Leu Asn Glu Asp Leu Thr Cys
145                 150                 155                 160

Asp Thr Leu Gln Met Trp Glu Ala Val Ser Val Lys Thr Glu Val Val
                165                 170                 175

Gly Ser Gly Ser Leu Leu Asp Val His Gly Phe Asn Lys Pro Thr Asp
            180                 185                 190

Thr Val Asn Thr Lys Gly Ile Ser Thr Pro Val Glu Gly Ser Gln Tyr
        195                 200                 205

His Val Phe Ala Val Gly Gly Glu Pro Leu Asp Leu Gln Gly Leu Val
    210                 215                 220

Thr Asp Ala Arg Thr Lys Tyr Lys Glu Glu Gly Val Val Thr Ile Lys
225                 230                 235                 240

Thr Ile Thr Lys Lys Asp Met Val Asn Lys Asp Gln Val Leu Asn Pro
                245                 250                 255

Ile Ser Lys Ala Lys Leu Asp Lys Asp Gly Met Tyr Pro Val Glu Ile
            260                 265                 270

Trp His Pro Asp Pro Ala Lys Asn Glu Asn Thr Arg Tyr Phe Gly Asn
        275                 280                 285

Tyr Thr Gly Gly Thr Thr Thr Pro Pro Val Leu Gln Phe Thr Asn Thr
    290                 295                 300

Leu Thr Thr Val Leu Leu Asp Glu Asn Gly Val Gly Pro Leu Cys Lys
305                 310                 315                 320

Gly Glu Gly Leu Tyr Leu Ser Cys Val Asp Ile Met Gly Trp Arg Val
                325                 330                 335

Thr Arg Ser Pro Tyr Asn Gly Lys Ser Ser Ala Tyr Asp Val His His
            340                 345                 350

Trp Arg Gly Leu Pro Arg Tyr Phe Lys Ile Thr Leu Arg Lys Arg Trp
        355                 360                 365

Val Lys Asn Pro Tyr Pro Met Ala Ser Leu Ile Ser Ser Leu Phe Asn
    370                 375                 380

Asn Met Leu Pro Gln Val Gln Gly Gln Pro Met Glu Gly Glu Asn Thr
385                 390                 395                 400

Gln Val Glu Glu Val Arg Val Tyr Asp Gly Thr Glu Pro Val Pro Gly
```

```
                405                 410                 415

Asp Pro Asp Met Thr Arg Tyr Val Asp Arg Phe Gly Lys Thr Lys Thr
            420                 425                 430

Val Phe Pro Gly Asn
        435


<210> SEQ ID NO 19
<211> LENGTH: 353
<212> TYPE: PRT
<213> ORGANISM: Artificial Sequence
<220> FEATURE:
<223> OTHER INFORMATION: VP1 dNdC 0000 with inserted peptides from HPV
      E7 antigenic sequences

<400> SEQUENCE: 19

His Gln Ala Glu Pro Asp Arg Ala His Tyr Asn Ile Val Thr Phe Cys
1               5                   10                  15

Cys Lys Cys Asp Val Leu Ile Lys Gly Gly Met Glu Val Leu Asp Leu
            20                  25                  30

Val Thr Gly Pro Asp Ser Val Thr Glu Ile Glu Ala Phe Leu Asn Pro
        35                  40                  45

Arg Met Gly Gln Pro Pro Thr Pro Glu Ser Leu Thr Glu Gly Gly Gln
    50                  55                  60

Tyr Tyr Gly Trp Ser Arg Gly Ile Asn Leu Ala Thr Ser Ala Gly Thr
65                  70                  75                  80

Glu Asp Ser Pro Gly Asn Asn Thr Leu Pro Thr Trp Ser Met Ala Lys
                85                  90                  95

Leu Gln Leu Pro Met Leu Asn Glu Asp Leu Thr Cys Asp Thr Leu Gln
            100                 105                 110

Met Trp Glu Ala Val Ser Val Lys Thr Glu Val Val Gly Ser Gly Ser
        115                 120                 125

Leu Leu Asp Val His Gly Phe Asn Lys Pro Thr Asp Thr Val Asn Thr
    130                 135                 140

Lys Gly Ile Ser Thr Pro Val Glu Gly Ser Gln Tyr His Val Phe Ala
145                 150                 155                 160

Val Gly Gly Glu Pro Leu Asp Leu Gln Gly Leu Val Thr Asp Ala Arg
                165                 170                 175

Thr Lys Tyr Lys Glu Glu Gly Val Val Thr Ile Lys Thr Ile Thr Lys
            180                 185                 190

Lys Asp Met Val Asn Lys Asp Gln Val Leu Asn Pro Ile Ser Lys Ala
        195                 200                 205

Lys Leu Asp Lys Asp Gly Met Tyr Pro Val Glu Ile Trp His Pro Asp
    210                 215                 220

Pro Ala Lys Asn Glu Asn Thr Arg Tyr Phe Gly Asn Tyr Thr Gly Gly
225                 230                 235                 240

Thr Thr Thr Pro Pro Val Leu Gln Phe Thr Asn Thr Leu Thr Thr Val
                245                 250                 255

Leu Leu Asp Glu Asn Gly Val Gly Pro Leu Cys Lys Gly Glu Gly Leu
            260                 265                 270

Tyr Leu Ser Cys Val Asp Ile Met Gly Trp Arg Val Thr Arg Ser Gln
        275                 280                 285

Ala Glu Pro Asp Arg Ala His Tyr Asn Ile Val Thr Phe Cys Cys Lys
    290                 295                 300

Cys Asp Ala Tyr Asp Val His His Trp Arg Gly Leu Pro Arg Tyr Phe
305                 310                 315                 320
```

```
Lys Ile Thr Leu Arg Lys Arg Trp Val Lys Asn Pro Tyr Gln Ala Glu
                325                 330                 335

Pro Asp Arg Ala His Tyr Asn Ile Val Thr Phe Cys Cys Lys Cys Asp
            340                 345                 350

Val


<210> SEQ ID NO 20
<211> LENGTH: 323
<212> TYPE: PRT
<213> ORGANISM: Artificial Sequence
<220> FEATURE:
<223> OTHER INFORMATION: VP1 dNdC 0000 with inserted peptides from HPV
      antigenic sequences

<400> SEQUENCE: 20

His Arg Ala His Tyr Asn Ile Val Thr Phe Val Leu Ile Lys Gly Gly
1               5                   10                  15

Met Glu Val Leu Asp Leu Val Thr Gly Pro Asp Ser Val Thr Glu Ile
            20                  25                  30

Glu Ala Phe Leu Asn Pro Arg Met Gly Gln Pro Pro Thr Pro Glu Ser
        35                  40                  45

Leu Thr Glu Gly Gly Gln Tyr Tyr Gly Trp Ser Arg Gly Ile Asn Leu
    50                  55                  60

Ala Thr Ser Ala Gly Thr Glu Asp Ser Pro Gly Asn Asn Thr Leu Pro
65                  70                  75                  80

Thr Trp Ser Met Ala Lys Leu Gln Leu Pro Met Leu Asn Glu Asp Leu
                85                  90                  95

Thr Cys Asp Thr Leu Gln Met Trp Glu Ala Val Ser Val Lys Thr Glu
            100                 105                 110

Val Val Gly Ser Gly Ser Leu Leu Asp Val His Gly Phe Asn Lys Pro
        115                 120                 125

Thr Asp Thr Val Asn Thr Lys Gly Ile Ser Thr Pro Val Glu Gly Ser
    130                 135                 140

Gln Tyr His Val Phe Ala Val Gly Gly Glu Pro Leu Asp Leu Gln Gly
145                 150                 155                 160

Leu Val Thr Asp Ala Arg Thr Lys Tyr Lys Glu Glu Gly Val Val Thr
                165                 170                 175

Ile Lys Thr Ile Thr Lys Lys Asp Met Val Asn Lys Asp Gln Val Leu
            180                 185                 190

Asn Pro Ile Ser Lys Ala Lys Leu Asp Lys Asp Gly Met Tyr Pro Val
        195                 200                 205

Glu Ile Trp His Pro Asp Pro Ala Lys Asn Glu Asn Thr Arg Tyr Phe
    210                 215                 220

Gly Asn Tyr Thr Gly Gly Thr Thr Thr Pro Pro Val Leu Gln Phe Thr
225                 230                 235                 240

Asn Thr Leu Thr Thr Val Leu Leu Asp Glu Asn Gly Val Gly Pro Leu
                245                 250                 255

Cys Lys Gly Glu Gly Leu Tyr Leu Ser Cys Val Asp Ile Met Gly Trp
            260                 265                 270

Arg Val Thr Arg Ser Arg Ala His Tyr Asn Ile Val Thr Phe Ala Tyr
        275                 280                 285

Asp Val His His Trp Arg Gly Leu Pro Arg Tyr Phe Lys Ile Thr Leu
    290                 295                 300

Arg Lys Arg Trp Val Lys Asn Pro Tyr Arg Ala His Tyr Asn Ile Val
305                 310                 315                 320
```

Thr Phe Val

<210> SEQ ID NO 21
<211> LENGTH: 709
<212> TYPE: PRT
<213> ORGANISM: Artificial Sequence
<220> FEATURE:
<223> OTHER INFORMATION: Amino acid sequence ADI-VP1 dNdC

<400> SEQUENCE: 21

```
Met Thr Ala Gln Thr Pro Ile His Val Tyr Ser Glu Ile Gly Lys Leu
1               5                   10                  15

Lys Lys Val Leu Leu His Arg Pro Gly Lys Glu Ile Glu Asn Leu Met
            20                  25                  30

Pro Asp Tyr Leu Glu Arg Leu Leu Phe Asp Asp Ile Pro Phe Leu Glu
        35                  40                  45

Asp Ala Gln Lys Glu His Asp Ala Phe Ala Gln Ala Leu Arg Asp Glu
    50                  55                  60

Gly Ile Glu Val Leu Tyr Leu Glu Thr Leu Ala Ala Glu Ser Leu Val
65                  70                  75                  80

Thr Pro Glu Ile Arg Glu Ala Phe Ile Asp Glu Tyr Leu Ser Glu Ala
                85                  90                  95

Asn Ile Arg Gly Arg Ala Thr Lys Lys Ala Ile Arg Glu Leu Leu Met
            100                 105                 110

Ala Ile Glu Asp Asn Gln Glu Leu Ile Glu Lys Thr Met Ala Gly Val
        115                 120                 125

Gln Lys Ser Glu Leu Pro Glu Ile Pro Ala Ser Glu Lys Gly Leu Thr
    130                 135                 140

Asp Leu Val Glu Ser Asn Tyr Pro Phe Ala Ile Asp Pro Met Pro Asn
145                 150                 155                 160

Leu Tyr Phe Thr Arg Asp Pro Phe Ala Thr Ile Gly Thr Gly Val Ser
                165                 170                 175

Leu Asn His Met Phe Ser Glu Thr Arg Asn Arg Glu Thr Leu Tyr Gly
            180                 185                 190

Lys Tyr Ile Phe Thr His His Pro Ile Tyr Gly Gly Gly Lys Val Pro
        195                 200                 205

Met Val Tyr Asp Arg Asn Glu Thr Thr Arg Ile Glu Gly Gly Asp Glu
    210                 215                 220

Leu Val Leu Ser Lys Asp Val Leu Ala Val Gly Ile Ser Gln Arg Thr
225                 230                 235                 240

Asp Ala Ala Ser Ile Glu Lys Leu Leu Val Asn Ile Phe Lys Gln Asn
                245                 250                 255

Leu Gly Phe Lys Lys Val Leu Ala Phe Glu Phe Ala Asn Asn Arg Lys
            260                 265                 270

Phe Met His Leu Asp Thr Val Phe Thr Met Val Asp Tyr Asp Lys Phe
        275                 280                 285

Thr Ile His Pro Glu Ile Glu Gly Asp Leu Arg Val Tyr Ser Val Thr
    290                 295                 300

Tyr Asp Asn Glu Glu Leu His Ile Val Glu Glu Lys Gly Asp Leu Ala
305                 310                 315                 320

Glu Leu Leu Ala Ala Asn Leu Gly Val Glu Lys Val Asp Leu Ile Arg
                325                 330                 335

Cys Gly Gly Asp Asn Leu Val Ala Ala Gly Arg Glu Gln Trp Asn Asp
            340                 345                 350

Gly Ser Asn Thr Leu Thr Ile Ala Pro Gly Val Val Val Val Tyr Asn
```

```
        355                 360                 365

Arg Asn Thr Ile Thr Asn Ala Ile Leu Glu Ser Lys Gly Leu Lys Leu
    370                 375                 380

Ile Lys Ile His Gly Ser Glu Leu Val Arg Gly Arg Gly Gly Pro Arg
385                 390                 395                 400

Cys Met Ser Met Pro Phe Glu Arg Glu Asp Ile Gly Ser Met Leu Leu
                405                 410                 415

Ile Lys Gly Gly Met Glu Val Leu Asp Leu Val Thr Gly Pro Asp Ser
            420                 425                 430

Val Thr Glu Ile Glu Ala Phe Leu Asn Pro Arg Met Gly Gln Pro Pro
        435                 440                 445

Thr Pro Glu Ser Leu Thr Glu Gly Gly Gln Tyr Tyr Gly Trp Ser Arg
    450                 455                 460

Gly Ile Asn Leu Ala Thr Ser Ala Gly Thr Glu Asp Ser Pro Gly Asn
465                 470                 475                 480

Asn Thr Leu Pro Thr Trp Ser Met Ala Lys Leu Gln Leu Pro Met Leu
                485                 490                 495

Asn Glu Asp Leu Thr Cys Asp Thr Leu Gln Met Trp Glu Ala Val Ser
            500                 505                 510

Val Lys Thr Glu Val Val Gly Ser Gly Ser Leu Leu Asp Val His Gly
        515                 520                 525

Phe Asn Lys Pro Thr Asp Thr Val Asn Thr Lys Gly Ile Ser Thr Pro
    530                 535                 540

Val Glu Gly Ser Gln Tyr His Val Phe Ala Val Gly Gly Glu Pro Leu
545                 550                 555                 560

Asp Leu Gln Gly Leu Val Thr Asp Ala Arg Thr Lys Tyr Lys Glu Glu
                565                 570                 575

Gly Val Val Thr Ile Lys Thr Ile Thr Lys Lys Asp Met Val Asn Lys
            580                 585                 590

Asp Gln Val Leu Asn Pro Ile Ser Lys Ala Lys Leu Asp Lys Asp Gly
        595                 600                 605

Met Tyr Pro Val Glu Ile Trp His Pro Asp Pro Ala Lys Asn Glu Asn
    610                 615                 620

Thr Arg Tyr Phe Gly Asn Tyr Thr Gly Gly Thr Thr Thr Pro Pro Val
625                 630                 635                 640

Leu Gln Phe Thr Asn Thr Leu Thr Thr Val Leu Leu Asp Glu Asn Gly
                645                 650                 655

Val Gly Pro Leu Cys Lys Gly Glu Gly Leu Tyr Leu Ser Cys Val Asp
            660                 665                 670

Ile Met Gly Trp Arg Val Thr Arg Ser Ala Tyr Asp Val His His Trp
        675                 680                 685

Arg Gly Leu Pro Arg Tyr Phe Lys Ile Thr Leu Arg Lys Arg Trp Val
    690                 695                 700

Lys Asn Pro Tyr Pro
705


<210> SEQ ID NO 22
<211> LENGTH: 725
<212> TYPE: PRT
<213> ORGANISM: Artificial Sequence
<220> FEATURE:
<223> OTHER INFORMATION: Amino acid sequence TF-VP1 dNdC

<400> SEQUENCE: 22

Met Ser Thr Ser Phe Glu Asn Lys Ala Thr Asn Arg Gly Val Ile Thr
```

-continued

```
1               5                   10                  15

Phe Thr Ile Ser Gln Asp Lys Ile Lys Pro Ala Leu Asp Lys Ala Phe
            20                  25                  30

Asn Lys Ile Lys Lys Asp Leu Asn Ala Pro Gly Phe Arg Lys Gly His
        35                  40                  45

Met Pro Arg Pro Val Phe Asn Gln Lys Phe Gly Glu Glu Val Leu Tyr
    50                  55                  60

Glu Asp Ala Leu Asn Ile Val Leu Pro Glu Ala Tyr Glu Ala Ala Val
65                  70                  75                  80

Thr Glu Leu Gly Leu Asp Val Val Ala Gln Pro Lys Ile Asp Val Val
                85                  90                  95

Ser Met Glu Lys Gly Lys Glu Trp Thr Leu Ser Ala Glu Val Val Thr
            100                 105                 110

Lys Pro Glu Val Lys Leu Gly Asp Tyr Lys Asn Leu Val Val Glu Val
        115                 120                 125

Asp Ala Ser Lys Glu Val Ser Asp Glu Asp Val Asp Ala Lys Ile Glu
    130                 135                 140

Arg Glu Arg Gln Asn Leu Ala Glu Leu Ile Ile Lys Asp Gly Glu Ala
145                 150                 155                 160

Ala Gln Gly Asp Thr Val Val Ile Asp Phe Val Gly Ser Val Asp Gly
                165                 170                 175

Val Glu Phe Asp Gly Gly Lys Gly Asp Asn Phe Ser Leu Glu Leu Gly
            180                 185                 190

Ser Gly Gln Phe Ile Pro Gly Phe Glu Asp Gln Leu Val Gly Ala Lys
        195                 200                 205

Ala Gly Asp Glu Val Glu Val Asn Val Thr Phe Pro Glu Ser Tyr Gln
    210                 215                 220

Ala Glu Asp Leu Ala Gly Lys Ala Ala Lys Phe Met Thr Thr Ile His
225                 230                 235                 240

Glu Val Lys Thr Lys Glu Val Pro Glu Leu Asp Asp Glu Leu Ala Lys
                245                 250                 255

Asp Ile Asp Glu Asp Val Asp Thr Leu Glu Asp Leu Lys Val Lys Tyr
            260                 265                 270

Arg Lys Glu Leu Glu Ala Ala Gln Glu Thr Ala Tyr Asp Asp Ala Val
        275                 280                 285

Glu Gly Ala Ala Ile Glu Leu Ala Val Ala Asn Ala Glu Ile Val Asp
    290                 295                 300

Leu Pro Glu Glu Met Ile His Glu Glu Val Asn Arg Ser Val Asn Glu
305                 310                 315                 320

Phe Met Gly Asn Met Gln Arg Gln Gly Ile Ser Pro Glu Met Tyr Phe
                325                 330                 335

Gln Leu Thr Gly Thr Thr Gln Glu Asp Leu His Asn Gln Tyr Ser Ala
            340                 345                 350

Glu Ala Asp Lys Arg Val Lys Thr Asn Leu Val Ile Glu Ala Ile Ala
        355                 360                 365

Lys Ala Glu Gly Phe Glu Ala Thr Asp Ser Glu Ile Glu Gln Glu Ile
    370                 375                 380

Asn Asp Leu Ala Thr Glu Tyr Asn Met Pro Ala Asp Gln Val Arg Ser
385                 390                 395                 400

Leu Leu Ser Ala Asp Met Leu Lys His Asp Ile Ala Met Lys Lys Ala
                405                 410                 415

Val Glu Val Ile Thr Ser Thr Ala Ser Val Lys Gly Ser Met Leu Leu
            420                 425                 430
```

-continued

```
Ile Lys Gly Gly Met Glu Val Leu Asp Leu Val Thr Gly Pro Asp Ser
        435                 440                 445

Val Thr Glu Ile Glu Ala Phe Leu Asn Pro Arg Met Gly Gln Pro Pro
    450                 455                 460

Thr Pro Glu Ser Leu Thr Glu Gly Gly Gln Tyr Tyr Gly Trp Ser Arg
465                 470                 475                 480

Gly Ile Asn Leu Ala Thr Ser Ala Gly Thr Glu Asp Ser Pro Gly Asn
                485                 490                 495

Asn Thr Leu Pro Thr Trp Ser Met Ala Lys Leu Gln Leu Pro Met Leu
            500                 505                 510

Asn Glu Asp Leu Thr Cys Asp Thr Leu Gln Met Trp Glu Ala Val Ser
        515                 520                 525

Val Lys Thr Glu Val Val Gly Ser Gly Ser Leu Leu Asp Val His Gly
    530                 535                 540

Phe Asn Lys Pro Thr Asp Thr Val Asn Thr Lys Gly Ile Ser Thr Pro
545                 550                 555                 560

Val Glu Gly Ser Gln Tyr His Val Phe Ala Val Gly Gly Glu Pro Leu
                565                 570                 575

Asp Leu Gln Gly Leu Val Thr Asp Ala Arg Thr Lys Tyr Lys Glu Glu
            580                 585                 590

Gly Val Val Thr Ile Lys Thr Ile Thr Lys Lys Asp Met Val Asn Lys
        595                 600                 605

Asp Gln Val Leu Asn Pro Ile Ser Lys Ala Lys Leu Asp Lys Asp Gly
    610                 615                 620

Met Tyr Pro Val Glu Ile Trp His Pro Asp Pro Ala Lys Asn Glu Asn
625                 630                 635                 640

Thr Arg Tyr Phe Gly Asn Tyr Thr Gly Gly Thr Thr Thr Pro Pro Val
                645                 650                 655

Leu Gln Phe Thr Asn Thr Leu Thr Thr Val Leu Leu Asp Glu Asn Gly
            660                 665                 670

Val Gly Pro Leu Cys Lys Gly Glu Gly Leu Tyr Leu Ser Cys Val Asp
        675                 680                 685

Ile Met Gly Trp Arg Val Thr Arg Ser Ala Tyr Asp Val His His Trp
    690                 695                 700

Arg Gly Leu Pro Arg Tyr Phe Lys Ile Thr Leu Arg Lys Arg Trp Val
705                 710                 715                 720

Lys Asn Pro Tyr Pro
                725


<210> SEQ ID NO 23
<211> LENGTH: 23
<212> TYPE: PRT
<213> ORGANISM: Influenza virus

<400> SEQUENCE: 23

Ser Leu Leu Thr Glu Val Glu Thr Pro Thr Arg Ser Glu Trp Glu Cys
1               5                   10                  15

Arg Cys Ser Asp Ser Ser Asp
            20


<210> SEQ ID NO 24
<211> LENGTH: 13
<212> TYPE: PRT
<213> ORGANISM: Hendra virus

<400> SEQUENCE: 24
```

Gly Leu Pro Asn Gln Ile Met Leu Gln Lys Thr Thr Ser
1 5 10

<210> SEQ ID NO 25
<211> LENGTH: 11
<212> TYPE: PRT
<213> ORGANISM: Hendra virus

<400> SEQUENCE: 25

Val Arg Pro Lys Ser Asp Ser Gly Asp Tyr Asn
1 5 10

<210> SEQ ID NO 26
<211> LENGTH: 11
<212> TYPE: PRT
<213> ORGANISM: Hendra virus

<400> SEQUENCE: 26

Pro Ile Ile His Ser Lys Tyr Ser Lys Ala Glu
1 5 10

<210> SEQ ID NO 27
<211> LENGTH: 15
<212> TYPE: PRT
<213> ORGANISM: Hendra virus

<400> SEQUENCE: 27

Val Glu Ile Tyr Asp Thr Gly Asp Ser Val Ile Arg Pro Lys Leu
1 5 10 15

<210> SEQ ID NO 28
<211> LENGTH: 14
<212> TYPE: PRT
<213> ORGANISM: Hendra virus

<400> SEQUENCE: 28

Leu Glu Lys Ile Gly Ser Cys Thr Arg Gly Ile Ala Lys Gln
1 5 10

<210> SEQ ID NO 29
<211> LENGTH: 28
<212> TYPE: PRT
<213> ORGANISM: group A streptococcus

<400> SEQUENCE: 29

Asn Ser Lys Thr Pro Ala Pro Ala Pro Ala Val Pro Val Lys Lys Glu
1 5 10 15

Ala Thr Lys Ser Lys Leu Ser Glu Ala Glu Leu His
20 25

<210> SEQ ID NO 30
<211> LENGTH: 19
<212> TYPE: PRT
<213> ORGANISM: group A streptococcus

<400> SEQUENCE: 30

Asn Ser Lys Asn Pro Val Pro Val Lys Lys Glu Ala Lys Leu Ser Glu
1 5 10 15

Ala Glu Leu

<210> SEQ ID NO 31
<211> LENGTH: 20
<212> TYPE: PRT

<213> ORGANISM: group A streptococcus

<400> SEQUENCE: 31

Leu Lys Met Leu Asn Arg Asp Leu Glu Gln Ala Tyr Asn Glu Leu Ser
1 5 10 15

Gly Glu Ala His
20

<210> SEQ ID NO 32
<211> LENGTH: 17
<212> TYPE: PRT
<213> ORGANISM: Influenza virus

<400> SEQUENCE: 32

Asp Ser Asn Lys Gly Val Thr Ala Ala Cys Pro His Ala Gly Ala Lys
1 5 10 15

Ser

<210> SEQ ID NO 33
<211> LENGTH: 7
<212> TYPE: PRT
<213> ORGANISM: Influenza virus

<400> SEQUENCE: 33

Pro Tyr Asn Gly Lys Ser Ser
1 5

<210> SEQ ID NO 34
<211> LENGTH: 17
<212> TYPE: PRT
<213> ORGANISM: Influenza virus

<400> SEQUENCE: 34

Gly Asn Asp Ala Ala Glu Gln Thr Lys Leu Tyr Gln Asn Pro Thr Thr
1 5 10 15

Tyr

<210> SEQ ID NO 35
<211> LENGTH: 19
<212> TYPE: PRT
<213> ORGANISM: Human Papilloma Virus

<400> SEQUENCE: 35

Gln Ala Glu Pro Asp Arg Ala His Tyr Asn Ile Val Thr Phe Cys Cys
1 5 10 15

Lys Cys Asp

<210> SEQ ID NO 36
<211> LENGTH: 9
<212> TYPE: PRT
<213> ORGANISM: Human Papilloma Virus

<400> SEQUENCE: 36

Arg Ala His Tyr Asn Ile Val Thr Phe
1 5

<210> SEQ ID NO 37
<211> LENGTH: 17
<212> TYPE: PRT
<213> ORGANISM: Influenza virus

<400> SEQUENCE: 37

```
Pro Asn Asp Ala Ala Glu Gln Thr Lys Leu Tyr Gln Asn Pro Thr Thr
1               5                   10                  15

Tyr


<210> SEQ ID NO 38
<211> LENGTH: 7
<212> TYPE: PRT
<213> ORGANISM: Influenza virus

<400> SEQUENCE: 38

Lys Arg Gly Pro Gly Ser Gly
1               5


<210> SEQ ID NO 39
<211> LENGTH: 17
<212> TYPE: PRT
<213> ORGANISM: Influenza virus

<400> SEQUENCE: 39

Pro Ser Thr Asn Gln Glu Gln Thr Ser Leu Tyr Val Gln Ala Ser Gly
1               5                   10                  15

Arg


<210> SEQ ID NO 40
<211> LENGTH: 7
<212> TYPE: PRT
<213> ORGANISM: Influenza virus

<400> SEQUENCE: 40

Ser His Lys Gly Lys Ser Ser
1               5


<210> SEQ ID NO 41
<211> LENGTH: 17
<212> TYPE: PRT
<213> ORGANISM: Influenza virus

<400> SEQUENCE: 41

Pro Ser Asn Ile Glu Asp Gln Lys Thr Ile Tyr Arg Lys Glu Asn Ala
1               5                   10                  15

Tyr


<210> SEQ ID NO 42
<211> LENGTH: 411
<212> TYPE: PRT
<213> ORGANISM: Streptococcus pyogenes

<400> SEQUENCE: 42

Met Thr Ala Gln Thr Pro Ile His Val Tyr Ser Glu Ile Gly Lys Leu
1               5                   10                  15

Lys Lys Val Leu Leu His Arg Pro Gly Lys Glu Ile Glu Asn Leu Met
            20                  25                  30

Pro Asp Tyr Leu Glu Arg Leu Leu Phe Asp Asp Ile Pro Phe Leu Glu
        35                  40                  45

Asp Ala Gln Lys Glu His Asp Ala Phe Ala Gln Ala Leu Arg Asp Glu
    50                  55                  60

Gly Ile Glu Val Leu Tyr Leu Glu Thr Leu Ala Ala Glu Ser Leu Val
65                  70                  75                  80

Thr Pro Glu Ile Arg Glu Ala Phe Ile Asp Glu Tyr Leu Ser Glu Ala
                85                  90                  95
```

```
Asn Ile Arg Gly Arg Ala Thr Lys Lys Ala Ile Arg Glu Leu Leu Met
            100                 105                 110

Ala Ile Glu Asp Asn Gln Glu Leu Ile Glu Lys Thr Met Ala Gly Val
        115                 120                 125

Gln Lys Ser Glu Leu Pro Glu Ile Pro Ala Ser Glu Lys Gly Leu Thr
    130                 135                 140

Asp Leu Val Glu Ser Ser Tyr Pro Phe Ala Ile Asp Pro Met Pro Asn
145                 150                 155                 160

Leu Tyr Phe Thr Arg Asp Pro Phe Ala Thr Ile Gly Thr Gly Val Ser
                165                 170                 175

Leu Asn His Met Phe Ser Glu Thr Arg Asn Arg Glu Thr Leu Tyr Gly
            180                 185                 190

Lys Tyr Ile Phe Thr His His Pro Ile Tyr Gly Gly Gly Lys Val Pro
        195                 200                 205

Met Val Tyr Asp Arg Asn Glu Thr Thr Arg Ile Glu Gly Gly Asp Glu
    210                 215                 220

Leu Val Leu Ser Lys Asp Val Leu Ala Val Gly Ile Ser Gln Arg Thr
225                 230                 235                 240

Asp Ala Ala Ser Ile Glu Lys Leu Leu Val Asn Ile Phe Lys Gln Asn
                245                 250                 255

Leu Gly Phe Lys Lys Val Leu Ala Phe Glu Phe Ala Asn Asn Arg Lys
            260                 265                 270

Phe Met His Leu Asp Thr Val Phe Thr Met Val Asp Tyr Asp Lys Phe
        275                 280                 285

Thr Ile His Pro Glu Ile Glu Gly Asp Leu Arg Val Tyr Ser Val Thr
    290                 295                 300

Tyr Asp Asn Glu Glu Leu His Ile Val Glu Glu Lys Gly Asp Leu Ala
305                 310                 315                 320

Glu Leu Leu Ala Ala Asn Leu Gly Val Glu Lys Val Asp Leu Ile Arg
                325                 330                 335

Cys Gly Gly Asp Asn Leu Val Ala Ala Gly Arg Glu Gln Trp Asn Asp
            340                 345                 350

Gly Ser Asn Thr Leu Thr Ile Ala Pro Gly Val Val Val Val Tyr Asn
        355                 360                 365

Arg Asn Thr Ile Thr Asn Ala Ile Leu Glu Ser Lys Gly Leu Lys Leu
    370                 375                 380

Ile Lys Ile His Gly Ser Glu Leu Val Arg Gly Arg Gly Gly Pro Arg
385                 390                 395                 400

Cys Met Ser Met Pro Phe Glu Arg Glu Asp Ile
                405                 410


<210> SEQ ID NO 43
<211> LENGTH: 427
<212> TYPE: PRT
<213> ORGANISM: Streptococcus pyogenes

<400> SEQUENCE: 43

Met Ser Thr Ser Phe Glu Asn Lys Ala Thr Asn Arg Gly Val Ile Thr
1               5                   10                  15

Phe Thr Ile Ser Gln Asp Lys Ile Lys Pro Ala Leu Asp Lys Ala Phe
            20                  25                  30

Asn Lys Ile Lys Lys Asp Leu Asn Ala Pro Gly Phe Arg Lys Gly His
        35                  40                  45

Met Pro Arg Pro Val Phe Asn Gln Lys Phe Gly Glu Glu Val Leu Tyr
    50                  55                  60
```

```
Glu Asp Ala Leu Asn Ile Val Leu Pro Glu Ala Tyr Glu Ala Ala Val
65                  70                  75                  80

Thr Glu Leu Gly Leu Asp Val Val Ala Gln Pro Lys Ile Asp Val Val
                85                  90                  95

Ser Met Glu Lys Gly Lys Glu Trp Thr Leu Ser Ala Glu Val Val Thr
            100                 105                 110

Lys Pro Glu Val Lys Leu Gly Asp Tyr Lys Asn Leu Val Val Glu Val
        115                 120                 125

Asp Ala Ser Lys Glu Val Ser Asp Glu Asp Val Asp Ala Lys Ile Glu
    130                 135                 140

Arg Glu Arg Gln Asn Leu Ala Glu Leu Ile Ile Lys Asp Gly Glu Ala
145                 150                 155                 160

Ala Gln Gly Asp Thr Val Val Ile Asp Phe Val Gly Ser Val Asp Gly
                165                 170                 175

Val Glu Phe Asp Gly Gly Lys Gly Asp Asn Phe Ser Leu Glu Leu Gly
            180                 185                 190

Ser Gly Gln Phe Ile Pro Gly Phe Glu Asp Gln Leu Val Gly Ala Lys
        195                 200                 205

Ala Gly Asp Glu Val Glu Val Asn Val Thr Phe Pro Glu Ser Tyr Gln
    210                 215                 220

Ala Glu Asp Leu Ala Gly Lys Ala Ala Lys Phe Met Thr Thr Ile His
225                 230                 235                 240

Glu Val Lys Thr Lys Glu Val Pro Glu Leu Asp Asp Glu Leu Ala Lys
                245                 250                 255

Asp Ile Asp Glu Asp Val Asp Thr Leu Glu Asp Leu Lys Val Lys Tyr
            260                 265                 270

Arg Lys Glu Leu Glu Ala Ala Gln Glu Thr Ala Tyr Asp Asp Ala Val
        275                 280                 285

Glu Gly Ala Ala Ile Glu Leu Ala Val Ala Asn Ala Glu Ile Val Asp
    290                 295                 300

Leu Pro Glu Glu Met Ile His Glu Glu Val Asn Arg Ser Val Asn Glu
305                 310                 315                 320

Phe Met Gly Asn Met Gln Arg Gln Gly Ile Ser Pro Glu Met Tyr Phe
                325                 330                 335

Gln Leu Thr Gly Thr Thr Gln Glu Asp Leu His Asn Gln Tyr Ser Ala
            340                 345                 350

Glu Ala Asp Lys Arg Val Lys Thr Asn Leu Val Ile Glu Ala Ile Ala
        355                 360                 365

Lys Ala Glu Gly Phe Glu Ala Thr Asp Ser Glu Ile Glu Gln Glu Ile
    370                 375                 380

Asn Asp Leu Ala Thr Glu Tyr Asn Met Pro Ala Asp Gln Val Arg Ser
385                 390                 395                 400

Leu Leu Ser Ala Asp Met Leu Lys His Asp Ile Ala Met Lys Lys Ala
                405                 410                 415

Val Glu Val Ile Thr Ser Thr Ala Ser Val Lys
            420                 425
```

<210> SEQ ID NO 44
<211> LENGTH: 8
<212> TYPE: PRT
<213> ORGANISM: Murine Polyomavirus

<400> SEQUENCE: 44

```
Leu Ala Thr Ser Asp Thr Glu Asp
```

1 5

<210> SEQ ID NO 45
<211> LENGTH: 9
<212> TYPE: PRT
<213> ORGANISM: Artificial Sequence
<220> FEATURE:
<223> OTHER INFORMATION: S1 of VP1 was mutated to include NaeI restriction site

<400> SEQUENCE: 45

Leu Ala Thr Ser Ala Gly Thr Glu Asp
1 5

<210> SEQ ID NO 46
<211> LENGTH: 6
<212> TYPE: PRT
<213> ORGANISM: Murine Polyomavirus

<400> SEQUENCE: 46

Thr Arg Asn Tyr Asp Val
1 5

<210> SEQ ID NO 47
<211> LENGTH: 7
<212> TYPE: PRT
<213> ORGANISM: Artificial Sequence
<220> FEATURE:
<223> OTHER INFORMATION: S4 of VP1 was mutated to include AfeI restriction site

<400> SEQUENCE: 47

Thr Arg Ser Ala Tyr Asp Val
1 5

<210> SEQ ID NO 48
<211> LENGTH: 21
<212> TYPE: PRT
<213> ORGANISM: Artificial Sequence
<220> FEATURE:
<223> OTHER INFORMATION: Amino acid sequence AM1 - peptide surfactant

<400> SEQUENCE: 48

Met Lys Gln Leu Ala Asp Ser Leu His Gln Leu Ala Arg Gln Val Ser
1 5 10 15

Arg Leu Glu His Ala
20

<210> SEQ ID NO 49
<211> LENGTH: 21
<212> TYPE: PRT
<213> ORGANISM: Artificial Sequence
<220> FEATURE:
<223> OTHER INFORMATION: Amino acid sequence Lac21 - peptide surfactant

<400> SEQUENCE: 49

Met Lys Gln Leu Ala Asp Ser Leu Met Gln Leu Ala Arg Gln Val Ser
1 5 10 15

Arg Leu Glu Ser Ala
20

IMMUNOGENIC COMPOSITIONS AND METHODS THEREFOR

CROSS-REFERENCE TO RELATED APPLICATIONS

This application is the U.S. National Stage of International Application PCT/AU2012/000952, filed Aug. 13, 2012, which designates the U.S. and was published by the International Bureau in English on Feb. 14, 2013, and which claims the benefit of Australian Application No. 2011903217, filed Aug. 11, 2011, both of which are hereby incorporated by reference in their entirety.

FIELD OF THE INVENTION

THIS invention relates to immunogenic compositions generally. In particular, this invention relates to viral capsomeres which comprise foreign immunogenic sequences for use in pharmaceutical compositions and more particularly, vaccine preparations. This invention also relates to use of novel adjuvants to augment immune responses.

BACKGROUND TO THE INVENTION

Subunit vaccines based on self-assembled major capsid proteins synthesised in heterologous cells, have proven effective in preventing infection by several pathogenic viruses, including hepatitis B virus and human papillomavirus. The use of viral capsomeres as subunit vaccines affords a number of advantages because they should result in highly homogeneous vaccine compositions. Moreover, capsomeres are considered to be a cost-effective alternative to VLP-based vaccines because they can be produced in relatively cost effective expression systems (such as bacterial expression systems) and because of their high degree of stability. In particular, if the capsomeres do not give rise to virus-like particles (VLPs) or other aggregates to any significant extent, compositions comprising such capsomeres should be substantially free of higher molecular weight forms of the capsid proteins. This is advantageous from a clinical standpoint wherein supplying a product of high consistency may be very important, indeed essential. That is, capsomeres may give rise to pharmaceutical compositions and in particular vaccines, of enhanced homogeneity. Also, since capsomeres are significantly smaller than VLPs, they may be easier to purify on conventional chromatographic media, thereby increasing the ease of manufacture.

Vaccine formulations comprising chimeric capsomeres can provide an advantage of increased antigenicity of both protein components of the fusion protein from which the capsomere is formed. For example, in a VLP, protein components of the underlying capsomere may be buried in the overall structure as a result of internalized positioning within the VLP itself. Similarly, epitopes of the protein components may be sterically obstructed as a result of capsomere-to-capsomere contact, and therefore unaccessible for eliciting an immune response. Capsomere vaccines potentially offer the additional advantage of increased antigenicity against any protein component.

The formulation of immunotherapeutic compositions and in particular vaccines with different adjuvants may affect the antibody response differently. Formulations that have been used to adjuvant capsomeres include cholera toxin, *Escherichia coli* enterotoxin, CpG, complete Freund's, and alum or alum in combination with monophosphoryl A. The most important issue in any adjuvant is its safety. Due to the toxicity, some adjuvants, such as complete Freund's adjuvant which causes strong local reaction, are only used in preclinical studies although they are very efficient in adjuvanting weak antigens.

Currently, only very few vaccine adjuvants are licensed for use in humans. Although both MF59 and aluminum salts have been approved in Europe, only aluminum salts have been used in licensed human vaccines in the United States. Billions of doses of vaccines containing aluminum salts have been shown to elicit early, high and long lasting antibody titers after a single immunization.

Aluminium salts have several disadvantages for use as adjuvants inclusive of a bias in the type of immune response elicited by aluminum salt adjuvants, instability to freezing and drying and inconsistencies in producing humoral immunity. Additionally, despite maintaining a good safety profile for more than seven decades, there have still been safety concerns regarding the use of aluminum salts. Symptoms such as erythema, allergic responses, hypersensitivity to contact, granulomatous inflammation and subcutaneous nodules as well as macrophagic myofascitis have been reported for patients who received an aluminum salt-containing vaccine. While aluminum salts offer an appropriate immune enhancement for some types of vaccines, they are clearly not adequate for all. This can also apply to MF59. MF59 consists of squalene, Tween 80, and Span 85 in sodium citrate buffer. There have been two reported cases of hypersensitivity reaction to the Tween 80.

SUMMARY OF THE INVENTION

The development of new and efficacious immunogen delivery vehicles and/or adjuvants is an ever evolving process in vaccinology.

In broad aspects, the invention relates to isolated proteins and capsomeres derived therefrom which comprise an addition at one or both termini of an immunogenic amino acid sequence of interest.

In a first aspect, the invention provides an isolated protein comprising a viral capsomere-forming amino acid sequence wherein the amino-terminus of said viral capsomere-forming amino acid sequence comprises an immunogenic amino acid sequence that is not a purification tag amino acid sequence and/or expression-enhancing tag amino acid sequence.

In a preferred embodiment, the viral capsomere-forming amino acid sequence further comprises at its carboxy-terminus an immunogenic amino acid sequence that is not a purification tag amino acid sequence and/or expression-enhancing tag amino acid sequence.

Suitably, the isolated protein of the first aspect further comprises an immunogenic amino acid sequence in one or more exposed loops of said viral capsomere-forming amino acid sequence.

In a particularly preferred embodiment of the first aspect, the isolated protein comprises a viral capsomere-forming amino acid sequence comprising at the amino-terminus and the carboxy-terminus of an immunogenic amino acid sequence that is not a purification tag amino acid sequence and/or expression-enhancing tag amino acid sequence; and an insertion of an immunogenic amino acid sequence in one or more exposed loops of said viral capsomere-forming amino acid sequence. More preferably, the immunogenic amino acid sequence is identical to or substantially identical to the immunogenic amino acid sequence that is not a purification tag amino acid sequence and/or expression-enhancing tag amino acid sequence.

Preferably, the viral capsomere forming sequence is derived from a polyomavirus and more preferably a murine polyomavirus. In preferred embodiments, the viral capsomere forming sequence derived from polyomavirus is VP1.

In a second aspect, the invention provides an isolated nucleic acid encoding an isolated protein of the first aspect.

In one embodiment of the second aspect, the invention provides an isolated nucleic acid encoding a viral capsomere-forming amino acid sequence, wherein the amino terminus of the viral capsomere-forming amino acid sequence has been adapted to receive at its amino terminus an isolated nucleic acid encoding an immunogenic amino acid sequence that is not a purification tag amino acid sequence and/or expression-enhancing tag sequence. In preferred embodiments, the carboxy terminus of the viral capsomere forming sequence is also adapted to receive an isolated nucleic acid encoding an immunogenic amino acid sequence that is not a purification tag amino acid sequence and/or expression-enhancing tag sequence.

In a third aspect, the invention provides a genetic construct comprising an isolated nucleic acid according to the second aspect.

Preferably, the genetic construct comprises an isolated nucleic acid according to the second aspect together with one or more other nucleotide sequences in a vector, and more preferably, operably-linked to one or more regulatory sequences in a vector.

Preferably, the genetic construct is an expression construct. According to these embodiments, the isolated nucleic acid is operably-linked to one or more regulatory sequences in an expression vector.

In a fourth aspect, the invention provides a host cell comprising the genetic construct of the third aspect.

Preferably, the host cell is selected from a prokaryotic cell and a eukaryotic cell.

More preferably, the host cell is a prokaryotic cell. Even more preferably, the prokaryotic cell is *E. coli.*

In a fifth aspect, the invention provides a capsomere comprising one or more isolated proteins of the first aspect.

Preferably, the capsomere is a chimeric capsomere.

In a sixth aspect, the invention provides a method of producing an isolated nucleic acid including the step of inserting at one or more nucleotide sequences adjacent or substantially adjacent the amino-terminus of a viral capsomere protein, a nucleotide sequence encoding an immunogenic amino acid sequence that is not a purification tag amino acid sequence and/or expression-enhancing tag sequence, or a fragment thereof.

Also included within the sixth aspect is an isolated nucleic acid produced by the method.

In a seventh aspect, the invention provides a method of producing a capsomere, including the steps of:

(a) introducing the isolated nucleic acid of the first aspect or the genetic construct of the third aspect into a host cell;

(b) culturing said host cell under conditions which facilitate production of the isolated protein of the first aspect;

(c) optionally purifying the isolated protein of the first aspect; and (d) assembling the isolated protein to thereby produce the capsomere.

Also included within the seventh aspect, is a capsomere produced by the method.

In an eighth aspect, the invention provides a pharmaceutical composition comprising one or more agents selected from the group consisting of an isolated protein, isolated nucleic acid and a capsomere according to any one of the aforementioned aspects, together with a pharmaceutically-acceptable carrier, diluent or excipient.

Preferably, the pharmaceutical composition is an immunotherapeutic composition.

More preferably, the pharmaceutical composition is a vaccine.

Compositions according to the eighth aspect may be used either prophylactically or therapeutically.

In a ninth aspect, the invention provides a method of treating an animal including the step of administering the pharmaceutical composition of the eighth aspect, or the capsomere of the fifth aspect, or a capsomere produced by the method of the seventh aspect to prophylactically or therapeutically treat a disease, disorder or condition.

It will be appreciated that the immunogenic amino acid sequence may be derived from, of, or corresponds to an immunogen from a pathogenic organism such as a virus, a bacteria, a fungi and a parasite, a cancer immunogen, an allergic reaction immunogen (i.e., an allergen), a transplantation immunogen and an autoantigen.

Preferably, the immunogenic amino acid sequence is derived from a virus, preferably influenza, Hendra virus or papillomavirus.

In a tenth aspect, the invention provides a method of immunising an animal including the step of administering the pharmaceutical composition of the eighth aspect, or the capsomere of the fifth aspect, or a capsomere produced by the method of the seventh aspect to said animal to thereby induce immunity in said animal.

In an eleventh aspect, the invention provides a pharmaceutical composition comprising an immunogen of interest and an adjuvant selected from the group consisting of a protein-surfactant stabilised emulsion, a solid particle substantially free of the immunogen of interest and a virus-like particle, together with a pharmaceutically-acceptable diluent, carrier or excipient.

Preferably, the pharmaceutical composition of the eleventh aspect is an immunotherapeutic composition.

More preferably, the pharmaceutical composition is a vaccine.

Compositions according to the eleventh aspect may be used either prophylactically or therapeutically.

In a twelfth aspect, the invention provides a method of augmenting an immune response in an animal, said method including the step of administering a pharmaceutical composition of the eleventh aspect or the capsomere of the fifth aspect, or a capsomere produced by the method of the seventh aspect to thereby augment an immune response in said animal.

In a thirteenth aspect, the invention provides a method of treating an animal including the step of administering the pharmaceutical composition of the eleventh aspect to prophylactically or therapeutically treat a disease, disorder or condition.

Preferably, the immunogen of interest and the adjuvant are mixed prior to administration to produce a formulation that does not subsequently undergo processing, purification or modification prior to administration.

Preferably, the protein-surfactant stabilised emulsion has a mean size of less than 200 nm and more preferably, a mean diameter size of less than 200 nm.

In preferred embodiments, the protein-surfactant stabilised emulsion is a peptide-surfactant stabilised emulsion.

Preferably, the protein-surfactant stabilised emulsion is an oil-in-water emulsion.

Suitably, the protein-surfactant stabilised emulsion further comprises a pharmaceutically-approved oil in mild buffer conditions.

Preferably, the solid particle is a silica particle.

Preferably, the immunogen of interest is a capsomere, more preferably the capsomere of the fifth aspect and even more preferably the chimeric capsomere of the fifth aspect.

The immune response of any one of the aforementioned aspects is a B cell and/or T cell response.

An animal of any of the aforementioned aspects can be selected from the group consisting of humans, domestic livestock, laboratory animals, performance animals, companion animals, poultry and other animals of commercial importance, although without limitation thereto.

Preferably, the animal is a mammal.

More preferably, the animal is a human.

In a fourteenth aspect, the invention provides a capsomere produced by the method of the seventh aspect.

In a fifteenth aspect, the invention provides an isolated nucleic acid produced by the method of the sixth aspect.

Throughout this specification, unless the context requires otherwise, the words "comprise", "comprises" and "comprising" will be understood to imply the inclusion of a stated integer or group of integers but not the exclusion of any other integer or group of integers.

BRIEF DESCRIPTION OF FIGURES

In order that the invention may be readily understood and put into practical effect, preferred embodiments will now be described by way of example with reference to the accompanying:

FIG. 1 Sequence alignment of generic vectors (SEQ ID NOs: 1, 2, 3, 4 and 5).

FIG. 2 Sequence alignment of vectors carrying HA epitope from loop A of H1N1 (SEQ ID NOs: 1, 4 and 6).

FIG. 6 Sequence alignment of VP1 constructs with M2e insert (SEQ ID NOs: 1, 4, 7 and 8).

FIG. 12 The amino acid sequences of VP1 dNdC 0000 with inserted peptides from Hendra Virus antigenic sequences (SEQ ID NOs: 1, 4, 9, 10, 11, 12 and 13).

FIG. 13 The amino acid sequences of VP1 dNdC 0000 with inserted peptides from GAS antigenic sequences (SEQ ID NOs: 1, 4, 14, 15 and 16).

FIG. 14 The amino acid sequences of chimeric VP1 with inserted peptides: M2e and HA epitopes A and B (SEQ ID NOs: 1, 17 and 18).

FIG. 20 The amino acid sequences of VP1 dNdC 0000 with inserted peptides from HPV E7 antigenic sequences (SEQ ID NOs: 1, 4, 19 and 20).

FIG. 27 Viral antigens: A. amino acid sequence of Arginine deiminase (ADI) from *Streptococcus pyogenes* (SEQ ID NO: 42; and B. amino acid sequence of trigger factor (TF) from *Streptococcus pyogenes* (SEQ ID NO: 43).

FIG. 29 Chimeric capsomere sequences: A. ADI-VP1 dNdC (SEQ ID NO: 21); and B. TF-VP1 dNdC (SEQ ID NO: 22).

BRIEF DESCRIPTION OF SEQUENCE LISTING

Figure 3A:
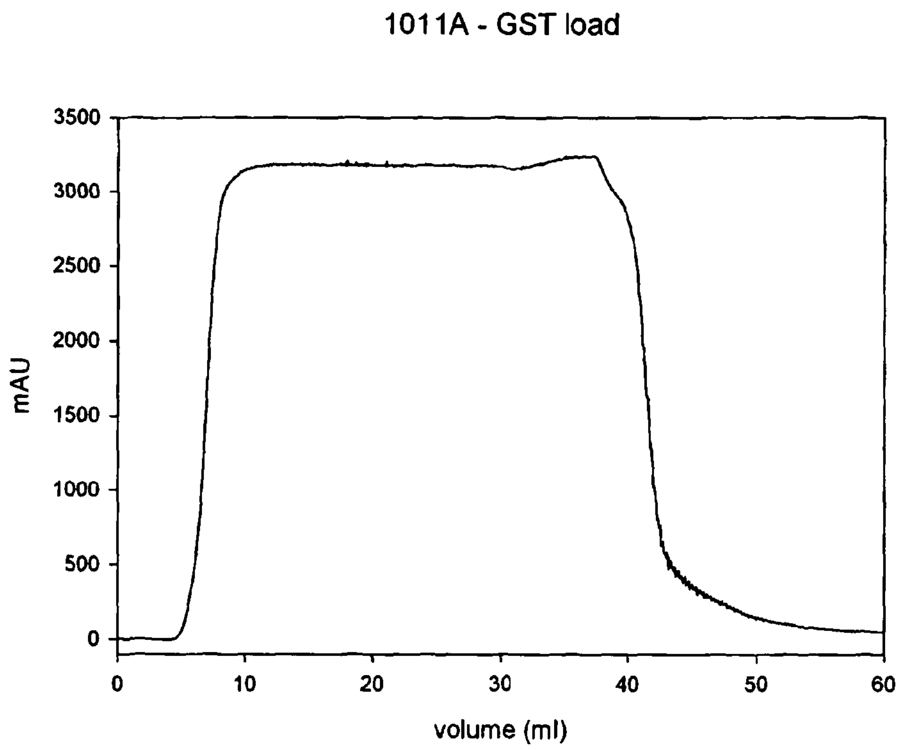
FIG. 3 Chromatogram of chimeric VP1 dNdC 1011A from GST purification.

Wild-Type and Chimeric Capsomere Sequences
SEQ ID NO: 1 Amino acid sequence VP1 wildtype
SEQ ID NO: 2 Amino acid sequence VP1 S1
SEQ ID NO: 3 Amino acid sequence VP1 S1 S4
SEQ ID NO: 4 Amino acid sequence VP1 dNdC 0000
SEQ ID NO: 5 Amino acid sequence VP1 dNdC S1 S4
SEQ ID NO: 6 Amino acid sequence VP1 dNdC 1011A
SEQ ID NO: 7 Amino acid sequence VP1dNdC 1011M2e
SEQ ID NO: 8 Amino acid sequence VP1dNdC 2022M2e
SEQ ID NO: 9 Amino acid sequence VP1dNdC 1011G1-2
SEQ ID NO: 10 Amino acid sequence VP1dNdC 1011G4
SEQ ID NO: 11 Amino acid sequence VP1dNdC 1011G5
SEQ ID NO: 12 Amino acid sequence VP1dNdC 1011G9
SEQ ID NO: 13 Amino acid sequence VP1dNdC 1011G10
SEQ ID NO: 14 Amino acid sequence 1011GAS1
SEQ ID NO: 15 Amino acid sequence 1011GAS2
SEQ ID NO: 16 Amino acid sequence 1011GAS3
SEQ ID NO: 17 Amino acid sequence M2e-VP1-S1A
SEQ ID NO: 18 Amino acid sequence M2e-VP1-S1B-S4A
SEQ ID NO: 19 Amino acid sequence VP1 dNdC 1011E7
SEQ ID NO: 20 Amino acid sequence VP1 dNdC 1011CTL
SEQ ID NO: 21 Amino acid sequence ADI-VP1 dNdC
SEQ ID NO: 22 Amino acid sequence TF-VP1 dNdC
Epitope sequences SEQ ID NO: 23 Amino acid sequence M2e peptide (SLLTEVETPTRSEWECRCSDSSD)
SEQ ID NO: 24 Amino acid sequence Hendra virus epitopes G1-2 (GLPNQIMLQKTTS)
SEQ ID NO: 25 Amino acid sequence Hendra virus epitope G4 (VRPKSDSGDYN)
SEQ ID NO: 26 Amino acid sequence Hendra virus epitope G5 (PIIHSKYSKAE)
SEQ ID NO: 27 Amino acid sequence Hendra virus epitope G9 (VEIYDTGDSVIRPKL)
SEQ ID NO: 28 Amino acid sequence Hendra virus epitope G10 (LEKIGSCTRGIAKQ)
SEQ ID NO: 29 Amino acid sequence GAS peptide $BSA10_{1-28}$ (NSKTPAPAPAVPVKKEATKSKLSEAELH)
SEQ ID NO: 30 Amino acid sequence GAS peptide $2032_{1-19}$ (NSKNPVPVKKEAKLSEAEL)
SEQ ID NO: 31 Amino acid sequence GAS peptide $2040_{50-69}$ (LKMLNRDLEQAYNELSGEAH)
SEQ ID NO: 32 Amino acid sequence HA epitope A of H1N1 (DSNKGVTAACPHAGAKS)
SEQ ID NO: 33 Amino acid sequence HA epitope A (PYNGKSS)
SEQ ID NO: 34 Amino acid sequence HA epitope B (GNDAAEQTKLYQNPTTY)
SEQ ID NO: 35 Amino acid sequence HPV E7 peptides (QAEPDRAHYNIVTFCCKCD)
SEQ ID NO: 36 Amino acid sequence HPV E7 peptide (RAHYNIVTF)
SEQ ID NO: 37 Amino acid sequence-antigenic epitope of loop B (PNDAAEQTKLYQNPTTY)
SEQ ID NO: 38 Amino acid sequence-antigenic epitope of loop A (KRGPGSG)
SEQ ID NO: 39 Amino acid sequence antigenic epitope of loop B (PSTNQEQTSLYVQASGR)
SEQ ID NO: 40 Amino acid sequence antigenic epitope of loop A (SHKGKSS)
SEQ ID NO: 41 Amino acid sequence-loop B (PSNIEDQKTIYRKENAY)
SEQ ID NO: 42 Amino acid sequence of the viral antigen Arginine deiminase (ADI) from *Streptococcus pyogenes* (FIG. 27-A)
SEQ ID NO: 43 Amino acid sequence of the viral antigen trigger factor (TF) from *Streptococcus pyogenes* (FIG. 27-B)

Other

SEQ ID NO: 44 Amino acid sequence LATSDTED (VP1 wildtype sequence, amino acids 82-89)
SEQ ID NO: 45 Amino acid sequence LATSAGTED (VP1 S1 sequence, amino acids 82-90)
SEQ ID NO: 46 Amino acid sequence TRNYDV (VP1 wildtype, amino acids 92-97)
SEQ ID NO: 47 Amino acid sequence TRSAYDV (VP1 S1S4 amino acids 92-98)
SEQ ID NO: 48 Amino acid sequence (common name AM1) MKQLADSLHQLARQVSRLEHA
SEQ ID NO: 49 Amino acid sequence (common name Lac21) MKQLADSLMQLARQVSRLESA

DETAILED DESCRIPTION OF THE INVENTION

The present invention is predicated, at least in part, on the finding that chimeric capsomeres with an N-terminal addition of an immunogenic protein are particularly advantageous for stimulating or eliciting a desired immune response and in particular, an effective immune response using a multiplicity of immunogenic protein sequences. Also particularly efficacious are capsomere with additions of immunogenic amino acid sequences at N and C termini and optional insertions of immunogenic amino acid sequences in one or more exposed loops of the capsomeres.

Therefore in broad aspects, the invention relates to isolated proteins, isolated nucleic acids and capsomeres derived therefrom which comprise an addition at one or both termini of an immunogenic amino acid sequence of interest. In particular, the addition is at the N-terminus and in preferred embodiments, at the N- and C-terminus. In particularly preferred embodiments, the isolated protein, isolated nucleic acids and capsomeres derived therefrom which comprise an addition at the N- and C-terminus also comprise an insertion of an immunogenic amino acid sequence at one or more exposed loops of the capsomere.

The present invention is also predicated on the notion that an immune response to immunogens of interest and more preferably, chimeric capsomeres may be augmented by certain classes of adjuvant.

Unless otherwise defined, all technical and scientific terms used herein have the same meaning as commonly understood by one of ordinary skill in the art to which this, invention belongs. The terminology used in the description of the invention herein is for the purpose of describing particular embodiments only and is not intended to be limiting of the invention.

The term "capsomere" is well-known in the art as a morphological unit of the capsid of a virus. A "capsomere" comprises monomeric or oligomeric viral structural proteins. In nature, capsomeres typically self-assemble into a virus-like particle. The capsomeres of the present invention are substantially incapable of assembly into VLPs due to the deletion of VLP assembly-related parts of the sequence and/or addition, of a foreign or heterologous sequence at the amino-terminus of the capsomere-forming amino acid sequence, and thus retain a capsomere morphology. By way of example for polyomavirus VP1 VLPs, five VP1 units self-associate to create a basic capsomeric unit. The VP1 VLP comprises 72 capsomeres associated into a capsid. In other examples, "capsomere" may refer to a papillomavirus capsomere, and preferably human papillomavirus, and in particular, refers to an oligomeric configuration of the L1 protein which is constituted of L1 pentamers. In other preferred embodiments, the capsomere is a hepatitis B virus capsomere, and more preferably, a hepatitis B virus surface antigen (HBsAg) capsomere.

A "viral capsomere-forming amino acid sequence" refers to an amino acid sequence which is capable of forming a capsomere. Such a sequence may correspond to, be derived from or related to a capsid-derived protein and more suitably, one or more viral structural proteins forming part of a viral capsid. It will be understood that by "capsid" is meant the structural portion of a virus which is comprised of capsomeres. The capsomere sequence is not limited to a virus of human origin but may be a sequence derived from any suitable virus. The capsomere forming sequence of the invention may be a chimera between two different viral structural or capsid proteins. The "viral capsomere-forming amino acid sequence" can be derived from or correspond to a suitable amino acid sequence from a virus such as, but not limited to, polyomavirus and papillomavirus, hepatitis B virus (HBV), hepatitis C virus (HCV), rotavirus, tobacco mosaic virus (TMV), cow pea mosaic virus (CPMV), bacteriophage MS2 and HIV.

In preferable embodiments, the viral capsomere-forming amino acid sequence is derived from or corresponds to a protein selected from the group consisting of polyomavirus VP1, papillomavirus L1, HBV surface antigen, HCV core, E1 or E2, VP1, 2, 3, 4, 5, 6 or 7 from rotavirus, TMV capsid protein, L and S protein of CPMV, MS2 coat protein and p24 protein of HIV.

Unless contraindicated or noted otherwise, in these descriptions and throughout this specification, the terms “a” and “an” mean one or more.

By “consisting of” is meant including, and limited to, whatever follows the phrase “consisting of.” Thus, the phrase “consisting of” indicates that the listed elements are required or mandatory, and that no other elements may be present.

By “consisting essentially of” is meant including any elements listed after the phrase, and limited to other elements that do not interfere with or contribute to the activity or action specified in the disclosure for the listed elements. Thus, the phrase “consisting essentially of” indicates that the listed elements are required or mandatory, but that other elements are optional and may or may not be present depending upon whether or not they affect the activity or action of the listed elements.

For the purposes of this invention, by “isolated” is meant material that has been removed from its natural state or otherwise been subjected to human manipulation. Isolated material may be substantially or essentially free from components that normally accompany it in its natural state, or may be manipulated so as to be in an artificial, state together with components that normally accompany it in its natural state. Isolated material may be in native, chemical synthetic or recombinant form.

By “protein” is meant an amino acid polymer. The amino acids may be natural or non-natural amino acids, D- or L-amino acids or chemically-derivatized amino acids as are well understood in the art.

A “peptide” is a protein having less than fifty (50) amino acids.

A “polypeptide” is a protein having fifty (50) or more amino acids.

Proteins, polypeptides and peptides may be useful in native, chemical synthetic or recombinant synthetic form.

The present invention is particularly amenable to generation of a chimera. A “chimera” or a “chimeric” gene, nucleic acid, protein, peptide or polypeptide is meant a gene, nucleic acid, protein, peptide or polypeptide that comprises two or more genes, nucleic acids, proteins, peptides or polypeptides not normally associated together. A “chimera” includes within its scope a fusion between fragments. Typically, although not exclusively, the chimera is a fusion between unrelated sequences however it is readily contemplated that the sequences may be homologues. Preferred embodiments of the present invention relate to a chimeric capsomere, isolated proteins encoding a chimeric capsomere and an isolated nucleic acid encoding said isolated proteins.

As used herein, by “synthetic” is meant not naturally occurring but made through human technical intervention. In the context of synthetic proteins and nucleic acids, this encompasses molecules produced by recombinant or chemical synthetic and combinatorial techniques as are well understood in the art.

The term “foreign” or “exogenous” or “heterologous” refers to any molecule (e. g., a polynucleotide or polypeptide) which is introduced into a host by experimental manipulations and may include gene/nucleic acid sequences found in that host so long as the introduced gene contains some modification (e.g., a point mutation, the presence of a selectable marker gene, the presence of a recombination site, etc.) relative to the naturally-occurring gene.

By “corresponds to” or “corresponding to” in the context of the present invention, is meant an amino acid sequence or nucleic acid sequence which shares primary sequence characteristics of another amino acid sequence or nucleic acid sequence but is not necessarily derived or obtained from the same source as said another amino acid sequence or said nucleic acid sequence.

By “an immunogenic amino acid sequence that is not a purification tag amino acid sequence and/or expression-enhancing tag amino acid sequence” is meant that said immunogenic sequence does not act as an amino acid sequence that is utilised for protein purification and/or does not act as an amino acid sequence that is utilised for enhancing expression of a recombinant protein. In preferred embodiments, the immunogenic amino acid sequence that is not a purification tag amino acid sequence.

A “purification tag amino acid sequence” is any amino acid sequence that is specifically fused to or associated with a second amino acid sequence to assist with purification, and in particular chromatographic purification (and more suitably, affinity chromatography) of a protein, peptides etc. The term may also be referred to as a “purification tag molecule”. Non-limiting examples of a purification tag include 6×HIS, glutathione S-transferase and c-myc. Inclusive of such sequences are sequences which specifically allow cleavage of the fusion partner from the capsomere-forming sequence, as normal protein engineering approaches would tend to incorporate a method for removal of the purification tag. An “expression enhancing sequence” is any amino acid sequence which aids with the recombinant expression of proteins and includes SUMO protein or fragments thereof.

The terms “immunogenic amino acid sequence”, “immunogenic sequence”, “immunogenic protein, “immunogenic amino acid sequence of interest”,” or “immunogen of interest” are used interchangeably herein with immunogen, antigen, epitope, antigenic sequence, polytope, immunogenic peptide, peptide, antigenic epitope etc as is known in the art to denote or refer to a sequence capable of eliciting an immune response, and more particularly a specific or desired immune response such as protective immune response or memory immune response. The term immunogen broadly includes any type of molecule which is recognized by a host immune system as being foreign. Immunogenic sequences of the invention may comprise B and/or T-cell epitopes. The immunogenic sequence may be fused with a purification tag sequence or expression enhancing tag to facilitate purification/expression but in itself, does not act as an purification tag molecule or expression enhancing tag; in these embodiments, the purification tag sequence may not be added to the amino-terminus of the viral capsomere forming sequence but is added to the amino-terminus of the immunogenic sequence e.g., tag molecule-immunogenic sequence-viral capsomere sequence. The immunogenic sequence can be an immunogen of an infectious agent, a cancer immunogen, an allergic reaction immunogen (i.e., an allergen), a transplantation immunogen, an autoantigen, and the like as are known in the art.

The term “native” nucleic acid or protein also refers to “wild-type” or “normal” nucleic acid or protein, which are normally obtainable from a selected organism or part thereof. These terms are used interchangeably.

The term “non-native” nucleic acid or protein refers to a nucleic acid or protein not normally obtainable from a selected organism or part thereof. For example, a non-native protein preferably comprises a chimeric protein that may comprise two peptides or proteins not normally associated with each other as a contiguous protein and accordingly comprise non-native proteins. Likewise, a chimeric nucleic acid may comprise two or more non-native nucleic acids.

Additions at termini contemplated by the invention may be directly adjacent to the terminus (ie. contiguous between the last nucleotide of the terminus sequence and the first nucleotide of the added sequence). Alternatively, there may be a spacer sequence between the capsomere sequence and the immunogenic sequence, such as a spacer sequence generated by a restriction enzyme site although without limitation thereto.

Therefore the capsomeres and isolated proteins thereof of the present invention may comprise a viral protein expressed as a fusion protein adjacent amino acid residues from a second protein, namely the desired immunogen of the present invention. Amino acids of the second protein can be derived from numerous sources as described herein as long as the addition of the second protein amino acid residues to the first protein permits formation of capsomeres. Amino acid residues of the second protein can be derived from numerous sources, including amino acid residues from the first protein.

The present invention also extends to use of fragments. In one embodiment, a "fragment" includes a protein comprising an amino acid sequence that constitutes less than 100% of an amino acid sequence of an entire protein. A fragment preferably comprises less than 99%, 98%, 97%, 96%, 95%, 94%, 93%, 92%, 91%, 90%, 85%, 80%, 75%, 70%, 60%, 50%, 40%, 30%, 20% or as little as even 10%, 5% or 3% of the entire protein.

In particular aspects, a protein fragment may comprise, for example, at least 5, 10, 20, 30, 40, 50 60, 70, 80, 90, 100, 120, 140, 150, 200, 250, 300, 350, 400, 450 or 500 contiguous amino acids of a protein.

In particular embodiments, the fragment may be a "biologically-active fragment" is a fragment, portion, region or segment of a protein, or a nucleic acid encoding the same, which displays at least 10%, preferably at least 25%, more preferably at least 50% and even more preferably at least 70%, 80% or 90% of the biological activity of the entire or full length protein from which it is derived. In preferred embodiments, a "biologically-active fragment" may be a fragment of a virus structural protein and/or virus capsid protein which retains the ability to self-assemble into capsomere, wherein the capsomere is substantially incapable of assembly into a VLP.

In other preferred embodiments, a "biologically-active fragment" is, a truncated protein including those having one or more amino acid residues deleted from the carboxy terminus of the protein, or one or more amino acid residues deleted from the amino terminus of the protein, or one or more amino acid residues deleted from an internal region (i.e., not from either terminus) of the protein. Preferred capsomeres are comprised of proteins truncated at the carboxy- and amino-terminus.

In preferred embodiments that relate to murine polyomavirus VP1, a suitable biologically-active fragment lacks the C-terminal 63 amino acids residues of wild-type VP1. Such a truncated VP1 is described in Garcea et al (1987), Nature 329: 86. In other preferred embodiments, a suitable biologically active fragment has the first 28 amino acids of wild-type VP1 are removed. In particularly preferred embodiments, a biologically active fragment is a murine polyomavirus VP1 sequence with the first 28 amino acids and the last 63 amino acids of wild-type VP1 missing. Such a sequence is exemplified in FIG. 1 and particularly an amino acid sequence as set forth in SEQ ID NO: 5. In other preferred embodiments, the suitable fragment is a fragment of the immunogenic protein of the invention. In particular suitable embodiments, such a fragment is an antigenic epitope.

Proteins, polypeptides, polytopes and peptides may be useful in native, chemical synthetic or recombinant synthetic form and may be produced by any means known in the art, including but not limited to, chemical synthesis, recombinant DNA technology and proteolytic cleavage to produce peptide fragments.

In one embodiment, proteins of the invention are produced by chemical synthesis. Chemical synthesis techniques are well known in the art, although the skilled person may refer to Chapter 18 of CURRENT PROTOCOLS IN PROTEIN SCIENCE Eds. Coligan et. al., John Wiley & Sons NY (1995-2009) for examples of suitable methodology.

In another preferred embodiment of the invention, isolated proteins of the invention may comprise intact viral or other proteins isolated from natural sources. Such proteins isolated from natural sources may be modified in vitro to include additional amino acid residues to provide a fusion protein of the invention using covalent modification techniques well known and routinely practiced in the art. Similarly, in formulations comprising truncated viral proteins, the proteins may be isolated from natural sources as intact proteins and hydrolyzed in vitro using chemical hydrolysis or enzymatic digestion with any of a number of site-specific or general proteases, the truncated protein subsequently modified to include additional amino acid resides as described above to provide a truncated fusion protein of the invention.

In another embodiment, proteins as described herein may be prepared as a recombinant protein.

A recombinant protein or peptide may be conveniently prepared by a person skilled in the art using standard protocols as for example described in Sambrook et al., MOLECULAR CLONING. A Laboratory Manual (Cold Spring Harbor Press, 1989), incorporated herein by reference, in particular Sections 16 and 17; CURRENT PROTOCOLS IN MOLECULAR BIOLOGY Eds. Ausubel et al., (John Wiley & Sons, Inc. 1995-2009), incorporated herein by reference, in particular Chapters 10 and 16; and CURRENT PROTOCOLS IN PROTEIN SCIENCE Eds. Coligan et al., (John Wiley & Sons, Inc. 1995-2009) which is incorporated by reference herein, in particular Chapters 1, 5 and 6. In producing capsomeres, recombinant molecular biology techniques can be utilized to produce DNA encoding either the desired intact protein, the truncated protein, or the truncated fusion protein. Recombinant methodologies required to produce a DNA encoding a desired protein are well known and routinely practiced in the art.

It is readily contemplated that any recombinant protein expression system may be used for the present invention such as bacterial, yeast, plant, insect cells, mammalian cell lines such as lymphoblastoid cell lines and splenocytes isolated from transformed host organisms such as humans and mice and insect-based expression systems but is not limited thereto. It will be appreciated that the recombinant protein expression system employed may be chosen on the basis of suitability for expression of soluble and stable protein.

In one preferred embodiment, recombinant protein expression occurs in cells of prokaryotic origin. Suitable host cells for recombinant protein expression are bacterial cells such as *Escherichia coli* (BL21 and various derivative strains thereof which have been optimised for certain applications, such as Rosetta and DE3, for example) and *Bacillus*

*subtilis*, although without limitation thereto. Preferably the host cell is *Escherichia coli* BL21 Rosetta (DE3).

In another preferred embodiment, recombinant expression occurs in insect cells which are suited to viral-based recombinant expression e.g. Sf9 cells.

The present invention contemplates recombinant expression of capsomeres in plant cells. By way of example, according to these embodiments a capsomere-forming sequence from a plant virus eg TMV or CPMV may be modified according to the methods of the present invention. Waheed et al (2011) *Transgenic Research* 20: 271-282 describes suitable methodology for capsomere expression in tobacco and is incorporated herein by reference.

To facilitate recombinant protein purification, a fusion partner sequence may be included with the protein of the present invention. That is, a genetic construct of the present invention may also include a fusion partner (typically provided by a vector or an expression vector) so that the recombinant protein of the invention is expressed as a fusion protein with said fusion partner. The main advantage of fusion partners is that they assist identification and/or purification of said fusion protein. However it will also be appreciated that the choice of fusion partner may also assist with protein properties such as stability, solubility and the like. Non-limiting examples of such proteins include Protein A, glutathione S-transferase (GST), green fluorescent protein (GFP) maltose-binding protein (MBP), hexahistidine ($HIS_6$) and epitope tags such as V5, FLAG, haemagglutinin and c-myc tags.

The fusion partner sequence facilitates fusion protein binding to an affinity matrix to enable protein purification and/or detection. For the purposes of fusion polypeptide purification by affinity chromatography, relevant matrices for affinity chromatography are antibody, protein A- or G-, glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system. In many cases, the fusion partner can be cleaved by an appropriate protease or chemical reagent to release the protein of interest from the fusion partner.

By "purify", "purified" and "purification", particularly in the context of recombinant protein purification, is meant enrichment of a recombinant protein so that the relative abundance and/or specific activity of said recombinant protein is increased compared to that before enrichment.

In those embodiments which contemplate peptides, said peptides may be in the form of peptides prepared by chemical synthesis, inclusive of solid phase and solution phase synthesis. Such methods are well known in the art, although reference is made to examples of chemical synthesis techniques as provided in Chapter 9 of SYNTHETIC VACCINES Ed. Nicholson (Blackwell Scientific Publications) and Chapter 15 of CURRENT PROTOCOLS IN PROTEIN SCIENCE Eds. Coligan et al., (John Wiley & Sons, Inc. NY USA 1995-2009). In this regard, reference is also made to International Publication WO 99/02550 and International Publication WO 97/45444.

By "chromatography" such as in the context of chromatographic steps of the invention, is meant any technique used for the separation of biomolecules (e.g., protein and/or nucleic acids) from complex mixtures that typically employs at least two phases: a stationary bed phase and a mobile phase that moves through the stationary bed. Molecules may be separated on the basis of a particular physicochemical property such as charge, size, affinity and hydrophobicity, or a combination thereof.

When recombinant proteins are used to provide capsomeres of the invention, the proteins may first be isolated from the host cell of its expression and incubated under conditions which permit self-assembly to provide capsomeres. Alternatively, the proteins may be expressed under conditions wherein capsomeres are formed in the host cell.

The present invention also contemplates the use of variants of any protein and/or nucleic acid encompassed by the invention. "Variants" include within their scope naturally-occurring variants such as allelic variants, orthologs and homologs and artificially created mutants, for example.

The terms "mutant", "mutation" and "mutated" are used herein generally to encompass conservative or non-conservative amino acid substitutions, deletions and/or insertions introduced into an isolated protein or fragment thereof.

It is well understood in the art that some amino acids may be changed to others with broadly similar properties without changing the nature of the activity of the protein or the structure of the protein (conservative substitutions).

Generally, non-conservative substitutions which are likely to produce the greatest changes in protein structure and function are those in which (a) a hydrophilic residue (e.g. Ser or Thr) is substituted for, or by, a hydrophobic residue (e.g. Ala, Leu, Ile, Phe or Val); (b) a cysteine or proline is substituted for, or by, any other residue; (c) a residue having an electropositive side chain (e.g. Arg, His or Lys) is substituted for, or by, an electronegative residue (e.g. Glu or Asp) or (d) a residue having a bulky hydrophobic or aromatic side chain (e.g. Val, Ile, Phe or Trp) is substituted for, or by, one having a smaller side chain (e.g. Ala, Ser) or no side chain (e.g. Gly).

With regard to protein variants and in particular those which are artificially-created mutants, these can be created by mutagenising a protein or by mutagenising an encoding nucleic acid, such as by random mutagenesis or site-directed mutagenesis. Examples of nucleic acid mutagenesis methods are provided in Chapter 9 of CURRENT PROTOCOLS IN MOLECULAR BIOLOGY, Ausubel et al., supra which is incorporated herein by reference.

It will be appreciated by the skilled person that site-directed mutagenesis is best performed where knowledge of the amino acid residues that contribute to biological activity is available. In many cases, this information is not available, or can only be inferred by molecular modelling approximations, for example.

In such cases, random mutagenesis is contemplated. Random mutagenesis methods include chemical modification of proteins by hydroxylamine (Ruan et al., 1997, Gene 188 35), incorporation of dNTP analogs into nucleic acids (Zaccolo et al., 1996, J. Mol. Biol. 255 589) and PCR-based random mutagenesis such as described in Stemmer, 1994, Proc. Natl. Acad. Sci. USA 91 10747 or Shafikhani et al., 1997, Biotechniques 23 304, each of which references is incorporated herein. It is also noted that PCR-based random mutagenesis kits are commercially available, such as the Diversify™ kit (Clontech).

The invention therefore also contemplates variants which share an appropriate level of sequence identity with isolated proteins and encoding nucleic acids as set forth herein. As generally used herein, a "homolog" shares a definable nucleotide or amino acid sequence relationship with a nucleic acid or protein of the invention as the case may be.

The term "sequence identity" is used herein in its broadest sense to include the number of exact nucleotide or amino acid matches having regard to an appropriate alignment using a standard algorithm, having regard to the extent that sequences are identical over a window of comparison. Thus, a "percentage of sequence identity" is calculated by comparing two optimally aligned sequences over the window of comparison, determining the number of positions at which the identical nucleic acid base (e.g., A, T, C, G, U) or amino acid residue occurs in both sequences to yield the number of matched positions, dividing the number of matched positions by the total number of positions in the window of comparison (i.e., the window size), and multiplying the result by 100 to yield the percentage of sequence identity. For example, "sequence identity" may be understood to mean the "match percentage" calculated by the DNASIS computer program (Version 2.5 for windows; available from Hitachi Software engineering Co., Ltd., South San Francisco, Calif., USA).

In particular embodiments, variants will share at least 30%, 40%, 50%, 55%, 60%, 65%, 70%, 75%, 80%, 85% or 90% and more preferably at least 95%, 96%, 97%, 98% or 99% sequence identity with the isolated proteins and/or isolated nucleic acids of the invention. It will be appreciated that a variant comprises all integer values less than 100%, for example the percent value as set forth above and others.

The invention also contemplates protein derivatives. By "derivative" is meant a polypeptide that has been derived from the basic sequence by modification, for example by conjugation or complexing with other chemical moieties or by post-translational modification techniques as would be understood in the art.

The term "derivative" also includes within its scope alterations that have been made to a parent sequence including additions or deletions that provide for functional equivalent molecules. The invention also contemplates chemical derivatives of the chimera of the present invention, such as produced using techniques described in CURRENT PROTOCOLS IN PROTEIN SCIENCE Chapter 15, for example. With regard to chemical modification of amino acids, this includes but is not limited to, modification by acylation, amidination, pyridoxylation of lysine, reductive alkylation, trinitrobenzylation of amino groups with 2,4,6-trinitrobenzene sulphonic acid (TNBS), amide modification of carboxyl groups and sulphydryl modification by performic acid oxidation of cysteine to cysteic acid, formation of mercurial derivatives, formation of mixed disulphides with other thiol compounds, reaction with maleimide, carboxymethylation with iodoacetic acid or iodoacetamide and carbamoylation with cyanate at alkaline pH, although without limitation thereto.

The invention further contemplates isolated proteins, isolated nucleic acids and capsomeres derived therefrom comprising an addition, and optionally an insertion, of the sequence of interest (and preferably the immunogenic sequence) at one or a plurality of the sites contemplated herein (a plurality being two, three or more). That is, encompassed in the invention is a single copy at one or a plurality of sites, multiple copies at one or a plurality of sites, or combinations thereof. Insertion or addition may be a single copy of a sequence of interest at one or a plurality of sites. Alternatively, multiple copies of a sequence of interest (preferably as tandem repeats) may be included at one or a plurality of sites. Also contemplated is a combination of a single copy inserts and a multiplicity of copies at different sites, in which a single isolated protein may comprise a single copy of the sequence of interest at one or more sites as well as multiple copies of an insert at one or more other sites. It will be appreciated that embodiments that contemplate a plurality, the sequence of interest may be the same sequence or different sequences. A particular advantage conferred by a multiplicity of inserts is the elicitation of an enhanced immune response.

In preferred embodiments, there is addition of a single copy or a plurality of copies of the sequence of interest at both the amino- and carboxy-terminus of the capsomere-forming sequence. In further particularly preferred embodiments, the invention contemplates an insertion of one or a plurality of copies of the sequence of interest at one or more exposed loops of the capsomere together with additions at either the amino-terminus or the amino- and carboxy-terminus as described hereinbefore. Non-limiting examples of such chimeric proteins are provided in Table 1.

In light of the foregoing, it will be appreciated that the present invention also contemplates isolated proteins, such as polypeptides or "polytope" proteins, comprising one or a plurality of isolated immunogenic fragments or sequences contemplated by the invention, and/or an isolated nucleic acid encoding the same. For example, said sequences or fragments may be present singly or as repeats, which also includes tandemly repeated fragments. "Spacer" amino acids may also be included between one or the plurality of the immunogenic sequences or fragments thereof present in said isolated protein. In one embodiment, an isolated polytope protein may comprise one or a plurality of isolated immunogenic fragments of the invention. In another embodiment, the isolated polytope protein may consist of one or a plurality of isolated immunogenic fragments of the invention. In yet another embodiment, an isolated protein may consist essentially of one or a plurality of isolated immunogenic fragments of the invention.

The isolated immunogenic proteins, fragments and/or polytopes of the present invention may be produced by any means known in the art, including but not limited to, chemical synthesis, recombinant DNA technology and proteolytic cleavage to produce peptide fragments.

The immunogenic sequences of the present invention possess the ability or potential to generate an immune response upon administration to an animal. It is envisaged that the immune response may be either mucosal, B-lymphocyte or T-lymphocyte mediated, or a combination thereof. The T-lymphocyte mediated response may be a specific cytotoxic T lymphocyte response. In preferred embodiments, the immunogenic sequences induce a neutralising antibody response. Preferably, the immune response is a protective immune response.

Suitably, the immunogenic proteins/sequences that are part of the isolated proteins and capsomeres of the present invention are derived from a pathogenic organism that causes or is related to an infectious disease of an animal, preferably a mammal and more preferably a human. Said pathogenic organisms include, but are not limited to, a virus, bacteria, a fungi, a mycobacterium and a parasite.

In the preferred embodiments that contemplate an immunogen from a virus and/or a viral capsomere sequence, the invention contemplates any member of the dsDNA Viruses group including (and without limitation thereto) any member of the family Adenoviridae inclusive of a mastadenovirus (eg, a human adenovirus) and an aviadenovirus (eg, a fowl adenovirus), although without limitation thereto; any member of the family Herpesviridae inclusive of an Alphaherpesvirinae such as, but not limited to, a simplexvirus (e.g., a human herpesvirus 1) and a varicellovirus (e.g. a human herpesvirus 3); a Betaherpesvirinae such as, but not limited to, a cytomegalovirus (e.g., human herpesvirus 5), a muromegalovirus (e.g., a mouse cytomegalovirus 1), a roseolovirus (e.g., a human herpesvirus 6); a Gammaherpesvirinae such as, but not limited to, a lymphocryptovirus (e.g., a human herpesvirus 4), a rhadinovirus (e.g., an ateline herpesvirus 2); any member of the family Papillomaviridae inclusive of a papillomavirus, preferably human papillomavirus, and preferably subtypes 16, 18, 31, 33, 35, 39, 45, 51, 52, 56, 58, and 59, although without limitation thereto; any member of the family Iridoviridae inclusive of a ranavirus and such as, epizootic haematopoietic necrosis virus, but not limited to; any member of the family Polyomaviridae inclusive of a polyomavirus and preferably murine polymavirus; any member of the family Poxviridae inclusive of an orthopoxvirus (e.g., a vaccinia virus), a parapoxvirus (e.g., a orf virus), an avipoxvirus (e.g., a fowlpox virus), an capripoxvirus (e.g., a sheep pox virus), a leporipoxvirus (e.g., a myxoma virus) and a suipoxvirus (e.g., a swinepox virus). A virus of the invention further contemplates any member of the ssDNA Viruses group including (and without limitation thereto) any member of the family Parvoviridae inclusive of a parvovirus (e.g., Rheumatoid arthritis virus, B19).

In the preferred embodiments that contemplate an immunogen from a virus and/or a viral capsomere sequence, the invention further contemplates any member of the dsRNA Viruses group including (and without limitation thereto) any member of the family Birnaviridae inclusive of an aquabirnavirus (e.g., an infectious pancreatic necrosis virus) and an avibirnavirus (e.g., infectious bursal disease virus); any member of the family Reoviridae inclusive of an orthoreovirus (e.g., a reovirus 3), a orbivirus (e.g., a bluetongue virus 1), a rotavirus, a coltivirus (e.g., a Colorado tick fever virus and an aquareovirus.

In the preferred embodiments that contemplate an immunogen from a virus and/or a viral capsomere sequence, the invention contemplates any member of the (+) sense RNA Virus group including (and without limitation thereto) any member of the family Astroviridae inclusive of an astrovirus (e.g., a human astrovirus) and an arterivirus (e.g., an equine arteritis virus); any member of the family Caliciviridae inclusive of a Norwalk virus, a Hepatitis E virus; any member of the family Coronaviridae inclusive of Corona Virus and SARS and a torovirus; any member of the family Flaviviridae inclusive of a flavivirus such as, but not limited to, yellow fever virus, dengue virus and West Nile virus; a pestivirus (e.g. bovine diarrhea virus) and hepatitis C-like viruses (e.g. a hepatitis C virus); any member of the family Picornaviridae inclusive of an enterovirus, a rhinovirus (e.g. a human rhinovirus 1A), a hepatovirus (e.g. a hepatitis A virus), a cardiovirus (e.g. a encephalomyocarditis virus) and an aphtovirus (e.g. foot-and-mouth disease virus); any member of the family Togaviridae inclusive of an alphavirus (e.g., a Sindbis virus) and a rubivirus (e.g. a *rubella* virus).

In the preferred embodiments that contemplate an immunogen from a virus and/or a viral capsomere sequence, the invention contemplates any member of the (−) negative sense RNAVirus group including (and without limitation thereto) any member of the family Filoviridae inclusive of a filovirus (e.g. Marburg virus, Ebola virus); any member of the family Paramyxoviridae inclusive of a paramyxovirus (e.g. a human parainfluenza virus 1), a morbillivirus (e.g. a measles virus), a rubulavirus (a mumps virus), a Hendra virus and a Nipah virus; any member of the family Pneumovirinae inclusive of a pneumovirus (eg. a human respiratory syncytial virus); any member of the family Rhabdoviridae inclusive of a vesiculovirus (e.g. a vesicular stomatitis virus, Indiana virus), a lyssavirus (e.g. a rabies virus) and an ephemerovirus (e.g. a bovine ephemeral fever virus); any member of the ambisense RNA Virus group inclusive of any member of the family Arenaviridae such as an arenavirus (e.g. lymphocytic choriomeningitis virus); any member of the family Bunyaviridae inclusive of a bunyavirus (e.g. Bunyamwera virus) and a hantavirus (e.g. a Hantaan virus); any member of the family Orthomyxoviridae inclusive of an influenzavirus A (such as an influenza A virus, an avian influenza A virus), an influenzavirus B (such as an influenza B virus), an influenzavirus C (such as an influenza C virus) and a "Thogoto-like viruses" (e.g. Thogoto virus).

In the preferred embodiments that contemplate an immunogen from a virus and/or a viral capsomere sequence, the invention contemplates any member of the RNA Reverse Transcribing Viruses group including any member of the family Retroviridae inclusive of a mammalian type B retrovirus (e.g. a mouse mammary tumor virus), a mammalian type C retrovirus (e.g. a murine leukemia virus), an avian type C retrovirus (e.g. a avian leukosis virus), a type D retrovirus (eg a Mason-Pfizer monkey virus), a BLV-HTLV retrovirus (e.g. a bovine leukemia virus), a lentivirus (e.g. a human immunodeficiency virus 1) and a spumavirus (e.g. a human spumavirus).

In relation to a virus, the invention contemplates any member of the DNA Reverse Transcribing Viruses group including any member of the family Hepadnaviridae inclusive of an orthohepadnavirus (e.g. a hepatitis B virus) and an avihepadnavirus (e.g. a duck hepatitis B virus), although without limitation thereto.

In the preferred embodiments that contemplate an immunogen from a virus and/or a viral capsomere sequence, the invention contemplates any member of the un-classified group of subviral agents such as satellites (e.g. tobacco necrosis virus), Viroids (hepatitis delta virus) and Agents of Spongiform Encephalopathies (e.g. prions, scrapie agent).

In a particularly preferred embodiment, the immunogen sequence corresponds to or is derived from a protein derived from an influenza virus. In preferable embodiments, the influenza virus protein is selected from the group consisting of hemagglutinin (HA), neuraminidase (NA), nuclear protein (NP), matrix protein M1 and matrix protein M2.

Preferably, the influenza virus protein is selected from the group consisting of HA and M2.

More preferably, the immunogenic protein or fragment thereof derived from an influenza virus is HA. Advantageously, the immunogenic protein derived from an influenza virus corresponds to a hypervariable region of HA. In another preferred embodiment, the immunogen is a domain of M2 and more preferably, M2e. Typically, although not exclusively, the domain of M2 is an ectodomain. In particularly preferred embodiments, the M2 immunogenic sequence comprises an amino acid sequence as set forth in SEQ ID NO: 23.

In particular preferred embodiments that relate to the HA protein, the immunogenic protein or fragment thereof corresponds to an exposed loop of HA selected from the group consisting of loop A, loop B, loop C, loop D and loop E, or a fragment thereof. Preferably, the exposed loop of HA is selected from the group consisting of loop A, loop B, loop C and loop E. More preferably, the exposed loop of HA is selected from the group consisting of loop A and loop B.

In more preferred embodiments, the fragment is an antigenic epitope of HA. In even more preferred embodiments, the fragment is an antigenic epitope of an exposed loop of HA selected from the group consisting of loop A, loop B, loop C and loop E.

A person skilled in the art will appreciate that viruses have evolved a number of mechanisms to evade the host cell immune response and, as a consequence, lead to generation of escape mutants. One such mechanism is the presence of a region within a virus protein/s with a high degree of variability, the so named hypervariable region. It will further be appreciated that the variability within an antigenic epitope between virus subtypes, and in particular influenza virus subtypes, can be substantial. Advantageously, although not exclusively, loop A and loop B comprise a minimal region which display a high degree of variability across virus subtypes.

Therefore in general embodiments where HA is derived from a H5 subtype of influenza virus, at least one consensus amino acid sequence for an antigenic epitope of loop A is PYqGKSS (SEQ ID NO: 33) (there is common q<-->N and K<-->R variability) whereas at least one consensus sequence for an antigenic epitope of loop B is PNDAAEQT-KLYQNPTTY (SEQ ID NO: 37) (there is common K<-->R variability), although without limitation thereto.

In other general embodiments where HA derived from a H3 subtype of influenza virus, at least one consensus amino acid sequence for an antigenic epitope of loop A is KRG-PgSG (SEQ ID NO: 38) (there is common PgS<-->PaS variability) whereas at least one consensus amino acid sequence for an antigenic epitope of loop B is PSTNQEQT-sLYVQASGR (SEQ ID NO: 39) (there is common TsL<-->TNL variability), although without limitation thereto.

In yet other general embodiments where HA is derived from a H1 subtype of influenza virus, at least one consensus amino acid sequence for an antigenic epitope of loop A is SHKGKSS (SEQ ID NO: 40), whereas at least one consensus amino acid sequence of loop B is PSNIEDQKTIYRKE-NAY (SEQ ID NO: 41), although without limitation thereto.

In preferred embodiments, the HA immunogenic sequence comprises or has an amino acid sequence selected from the group consisting of SEQ ID NO: 32, SEQ ID NO: 33, SEQ ID NO: 34, SEQ ID NO: 37, SEQ ID NO: 38, SEQ ID NO: 39, SEQ ID NO: 40 and SEQ ID NO: 41.

Other particularly preferred embodiments relate to an immunogenic protein derived from or corresponding to a protein from Hendra virus or Nipah virus. According to these preferred embodiments, the immunogenic protein or fragment thereof from Hendra virus or Nipah virus is derived from or corresponds to attachment-envelope glycoprotein G. More preferably, the G protein fragment comprises or has an amino sequence selected from the group consisting of SEQ ID NO: 24, SEQ ID NO: 25, SEQ ID NO: 26, SEQ. ID NO: 27 and SEQ ID NO: 28.

Other preferred embodiments relate to use of immunogens that elicit an immune response against human papillomavirus (HPV) and more preferably, a HPV type selected from the group consisting of HPV16, 18, 31, 33, 35, 39, 45, 51, 52, 56, 58, 66 and 68. In preferable embodiments, the HPV type is HPV16. It is also contemplated that HPV types, especially high risk HPV types, that have yet to be identified are encompassed by the invention. According to particularly preferred embodiments, HPV immunogenic sequence is derived from or corresponds to the E7 protein of HPV or a fragment thereof. Preferably, E7 protein fragment comprises or has an amino acid sequence selected from SEQ ID NO: 35 and SEQ ID NO: 36.

Examples of infectious fungi include: *Cryptococcus neoformans, Histoplasma capsulatum, Coccidioides immitis, Blastomyces dermatitidis, Chlamydia trachomatis, Candida albicans*, although without limitation thereto.

The invention also contemplates immunogenic proteins from a parasite inclusive of a protozoan, a roundworm, a fluke and a tapeworm. Protozoans are inclusive of an *Amebiasis* sp, a *Babesia* sp, a *Cryptosporidium* sp, a *Cyclosporia* sp, a *Giardia* sp, a *Leishmania* sp, a *Microsporidia* sp, a *Toxoplasma* sp and a *Plasmodium* sp, although without limitation thereto. In embodiments that relate to the genus *Plasmodium*, contemplated are any *Plasmodium* species that is the causative agent of or is related to malaria such as *Plasmodium falciparum, Plasmodium vivax, Plasmodium ovale* and *Plasmodium malaria*. Preferred embodiments relate to *Plasmodium falciparum*. A roundworm is inclusive of a filarial sp, a *strongyloidial* sp, a *trichinellosis* sp and a *toxocariasis* sp. A fluke is inclusive of a *Paragonimus* sp and a *Schistosoma* sp, although without limitation thereto. A tapeworm is inclusive of a *Cysticercosis* sp and an Echinococcosis sp although without limitation thereto.

The invention also encompasses use of immunogenic proteins from bacteria and in particular, Gram-positive and Gram-negative bacteria inclusive of a *Salmonella* sp (eg. *Salmonella typhi*), a *Neisseria* sp (eg. *Neisseria gonorrhoeae, N. meningitidis*), a *Legionella* sp, a *Mycobacterium* (*Mycobacterium tuberculosis*), eg *Chlamydia* sp, and *Chlamydophila* spp, (eg. *Chlamydia trachomatis, Chlamydophila pneumoniae, C. psittaci*), a *Listeria* spp, a *Brucella* sp, a *Streptococcus* sp (eg. *Streptococcus pneumoniae, Streptococcus pyogenes* (group A *Streptococcus*; GAS), *S. agalactiae* (group B *Streptococcus*; GBS, and *S. mutans*), a *Haemopholia* sp (eg. *Haemophilus influenzae*), *Pasteurella* species, a *Vibrio* sp (eg. *Vibrio cholera*), *Escherichia coli*, a *Coxiellaceae* sp (eg. *Coxiella bumetii*) pathogenic *Campylobacter* sp., *Enterococcus* sp., a *Bacillus* sp (eg *Bacillus antracis*; anthrax toxin), a *Helicobacter* sp and in particular *Helicobacter pyloris, Clostridium* sp (eg *Clostridium perfringers, Clostridium tetani*), a *Borelia* sp (eg. *Borelia burgdorferi*), and a *Rickettsiales* sp, although without limitation thereto.

In preferred embodiments that relate to *Streptococcus pyogenes*, the immunogenic protein is derived from or corresponds to a *Streptococcus pyogenes* protein selected from the group consisting of M protein, C5a peptidase, SpeB, group A carbohydrate, the fibronectin binding proteins Sfb1, SOF and FBP54, trigger factor (TF), ketopantoate reductase (KPR), arginine deiminase (ADI), ornithine carbamoyltransferase (OCTase), phosphotransacetylase (PTA), ribosome recycling factor (RRF), branched-chain-amino-acid aminotransferase (BCAT), carbamate kinase (CK), adenylate kinase (AK), elongation factor P (EF-P), high temperature requirement A serine protease (HtrA), phosphoglycerate kinase (PGK), 6-phosphofructokinase (PFK), NADP dependent glyceraldehyde 3 phosphate dehydrogenase (NADP-GAPDH) and Spy1262.

Preferably, the immunogenic protein or fragment corresponds to or is derived from M protein and more preferably, the amino terminal region of M protein which corresponds to any one or more amino acid residues up to and inclusive of about residue number 100 of wild-type M protein. In particularly preferred embodiments that relate to M protein, the immunogen comprises an amino acid sequence selected from the group consisting of SEQ ID NO: 29, SEQ ID NO: 30 and SEQ ID NO: 31. Other suitable immunogenic peptides from M protein are provided in Brandt et al, Infect Immun. 2000 December; 68(12): 6587-6594, which is incorporated herein by reference.

Other medically relevant microorganisms have been described extensively in the literature, e.g., see C. G. A Thomas, *Medical Microbiology*, Bailliere Tindall, Great Britain 1983, the entire contents of which is hereby incorporated by reference.

The invention also contemplates use of immunogenic proteins derived from a protein associated with or causative of a cancer, a neurological disease, (and more preferably a degenerative neurological disease), an allergy and an autoimmune disease. Such proteins may be self-antigens.

Therefore the invention contemplates tumour antigens and tumour associated antigens (may collectively be referred to as 'cancer antigens') found in or associated with a germ cell tumour, a bowel cancer, a breast cancer, an ovarian cancer, a genitourinary cancer such as a prostate cancer and a testicular cancer, a brain cancer, a liver cancer, a pancreatic cancer, an oesophageal cancer, B cell lymphoma, T cell lymphoma, myeloma, leukemia, hematopoietic neoplasias, thymoma, lymphoma, sarcoma, lung cancer, non-Hodgkins lymphoma, Hodgkins lymphoma, uterine cancer, adenocarcinoma, pancreatic cancer, colon cancer, lung cancer, renal cancer, bladder cancer, a primary or metastatic melanoma, squamous cell carcinoma, basal cell carcinoma, angiosarcoma, hemangiosarcoma, head and neck carcinoma, thyroid carcinoma, soft tissue sarcoma, bone sarcoma, uterine cancer, cervical cancer, gastrointestinal cancer, biliary tract cancer, choriocarcinoma, colon cancer, endometrial cancer, esophageal cancer, gastric cancer, intraepithelial neoplasms, lymphomas, lung cancer (e.g. small cell and non-small cell), neuroblastomas, oral cancer, rectal cancer; skin cancer, as well as other carcinomas and sarcomas, although without limitation thereto and any other cancer now known or later identified (see, e.g., Rosenberg (1996) *Ann. Rev. Med.* 47:481-491, the entire contents of which are incorporated by reference herein). It will be appreciated that the cancer may be a malignant or nonmalignant cancer.

Non-limiting examples of tumour and/or tumour-associated antigens are alphafetoprotein, carcinoembryonic antigen (CEA), CA-125, MUC-1, ras, p53, epithelial tumor antigen (ETA), tyrosinase, HER2/neu and BRCA1 antigens for breast cancer, MART-1/MelanA, gp100, TRP-1, TRP-2, NY-ESO-1, CDK-4, |3-catenin, MUM-1, Caspase-8, KIAA0205, HPVE7, SART-1, PRAME, and p 15 antigens, members of the Melanoma-associated antigen (MAGE) family, the BAGE family (such as BAGE-1), the DAGE/PRAME family (such as DAGE-1), the GAGE family, the RAGE family (such as RAGE-1), the SMAGE family, NAG, TAG-72, CA125, mutated proto-oncogenes such as p21 ras, mutated tumor suppressor genes such as p53, tumor associated viral antigens (e.g., HPV16 E7), the SSX family, HOM-MEL-55, NY-COL-2, HOM-HD-397, HOM-RCC1.14, HOM-HD-21, HOM-NSCLC-11, HOM-MEL-2.4, HOM-TES-11, RCC-3.1.3, NY-ESO-1, and the SCP family. Members of the MAGE family include, but are not limited to, MAGE-1, MAGE-2, MAGE-3, MAGE4 and MAGE-11. Members of the GAGE family include, but are not limited to, GAGE-1, GAGE-6. See, e.g., review by Van den Eynde and van der Bruggen (1997) in *Curr. Opin. Immunol.* 9: 684-693, Sahin et al. (1997) in *Curr. Opin. Immunol.* 9: 709-716, and Shawler et al. (1997), the entire contents of which are incorporated by reference herein for their teachings of cancer antigens.

The cancer antigen can also be, but is not limited to, human epithelial cell mucin (Muc-1; a 20 amino acid core repeat for Muc-1 glycoprotein, present on breast cancer cells and pancreatic cancer cells), MUC-2, MUC-3, MUC-18, the Ha-ras oncogene product, carcino-embryonic antigen (CEA), the raf oncogene product, CA-125, GD2, GD3, GM2, TF, sTn, gp75, EBV-LMP 1 & 2, HPV-F4, 6, 7, prostatic serum antigen (PSA), prostate-specific membrane antigen (PSMA), C017-1A, GA733, gp72, p53, the ras oncogene product, 13-HCG, gp43, HSP-70, pi 7 mel, HSP70, gp43, HMW, HOJ-1, melanoma gangliosides, TAG-72, mutated proto-oncogenes such as p21 ras, mutated tumor suppressor genes such as p53, estrogen receptor, milk fat globulin, telomerases, nuclear matrix proteins, prostatic acid phosphatase, protein MZ2-E, polymorphic epithelial mucin (PEM), folate-binding-protein LK26, truncated epidermal growth factor receptor (EGFR), Thomsen-Friedenreich (T) antigen, GM-2 and GD-2 gangliosides, polymorphic epithelial mucin, folate-binding protein LK26, human chorionic gonadotropin (HCG), pancreatic oncofetal antigen, cancer antigens 15-3, 19-9, 549, 195, squamous cell carcinoma antigen (SCCA), ovarian cancer antigen (OCA), pancreas cancer associated antigen (PaA), mutant K-ras proteins, mutant p53, and chimeric protein p210BCR_ABL and tumor associated viral antigens (e.g., HPV16 E7).

The cancer antigen can also be an antibody produced by a B cell tumor (e.g., B cell lymphoma; B cell leukemia; myeloma; hairy cell leukemia), a fragment of such an antibody, which contains an epitope of the idiotype of the antibody, a malignant B cell antigen receptor, a malignant B cell immunoglobulin idiotype, a variable region of an immunoglobulin, a hypervariable region or complementarity determining region (CDR) of a variable region of an immunoglobulin, a malignant T cell receptor (TCR), a variable region of a TCR and/or a hypervariable region of a TCR. In one embodiment, the cancer antigen of this invention can be a single chain antibody (scFv), comprising linked VH, and VL domains, which retains the conformation and specific binding activity of the native idiotype of the antibody.

The cancer antigens that can be used in accordance with the present invention are in no way limited to the cancer antigens listed herein. Other cancer antigens can be identified, isolated and cloned by methods known in the art such as those disclosed in U.S. Pat. No. 4,514,506, the entire contents of which are incorporated by reference herein.

In relation to degenerative neurological diseases associated with dementia, the invention contemplates Alzheimer's disease and Lewy body dementia, although without limitation thereto. An immunogenic protein for Alzheimer's disease includes (and without limitation thereto) Amyloid beta (Aβ or Abeta), which is a peptide of 36-43 amino acids that appears to be the main constituent of amyloid plaques, which are deposits found in the brains of patients with Alzheimer's disease).

Immunogenic proteins that are associated with or causative of autoimmune diseases such as rheumatoid arthritis and diabetes are particularly amenable for use in the present invention. In suitable embodiments that relate to rheumatoid arthritis, the immunogenic protein may be derived from arthritogenic auto-antigen.

The immunogen can further be an autoantigen (for example, to enhance self-tolerance to an autoantigen in a subject, e.g., a subject in whom self-tolerance is impaired). Exemplary autoantigens include, but are not limited to, myelin basic protein, islet cell antigens, insulin, collagen and human collagen glycoprotein, muscle acetylcholine receptor and its separate polypeptide chains and peptide epitopes, glutamic acid decarboxylase and muscle-specific receptor tyrosine kinase.

The present invention also relates to use of immunogenic sequences in chimeric capsomeres that are allergens. An "allergen" refers to a substance (antigen) that tan induce an allergic or asthmatic response in a susceptible subject. An "allergy" refers to acquired hypersensitivity to a substance (allergen). Allergic conditions include but are not limited to eczema, allergic rhinitis or coryza, conjunctivitis, hay fever, bronchial asthma, urticaria (hives) and food allergies, and other atopic conditions. Allergies are generally caused by IgE antibody generation against harmless allergens.

"Asthma" refers to a disorder of the respiratory system characterized by inflammation, narrowing of the airways and increased reactivity of the airways to inhaled agents. Asthma is frequently, although not exclusively associated with atopic or allergic symptoms.

The list of allergens is enormous and can include pollens, insect venoms, plant proteins, animal dander dust, fungal spores and drugs (e.g. penicillin). Examples of natural, animal and plant allergens include but are not limited to proteins specific to the following genuses: *Canine* (*Canis familiaris*); *Dermatophagoides* (e.g. *Dermatophagoides farinae*); *Felis* (*Felis domesticus*); *Ambrosia* ((*Ambrosia artemiisfolia*); *Lolium* (e.g. *Lolium perenne* OK *Lolium multiflorum*); *Cryptomeria* (*Cryptomeria japonica*); *Altemaria* (*Altemaria altemata*); *Alder; Alnus* (*Alnus gultinoasa*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poapratensis* or *Poa compressa*); *Avena* (e.g. *Avena sativa*); *Holcus* (e.g. *Holcus lanatus*); *Anthoxanthum* (e.g. *Anthoxanthum odoratum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); *Ricinus* (eg. *Ricinus communis* and more preferably, ricin protein) and *Bromus* (e.g. *Bromus inermis*).

The invention also contemplates chimeric capsomeres comprising designed bioweapons or other toxic proteins.

Although many of the pathogenic or toxic antigens or sequences described above relate to human disorders, the invention is also useful for treating other nonhuman vertebrates. Nonhuman vertebrates are also capable of developing infections which can be prevented or treated with proteins, nucleic acid and capsomeres of the present invention. For instance, in addition to the treatment of infectious human diseases, the methods of the invention are useful for treating infections of animals.

As hereinbefore described the invention contemplates capsomeres with insertion of an immunogenic sequence into one or more surface exposed loops of a viral capsomere sequence in conjunction with addition/s of immunogenic sequences at the terminus. A particular advantage conferred by chimeric capsomeres with insertion into exposed loops is enhanced and/or more efficient surface presentation of the immunogen to the immune system. Reference is made to International Publication No. WO2008/040060 in the name of the University of Queensland which provides non-limiting examples of insertion into exposed loops and is incorporated herein by reference.

In those embodiments which relate to a viral capsomere forming sequence that is derived from VP1, it is understood that VP1 comprises four surface exposed loops which span around about residues 82-89, 221-224, 247-249 and 292-297 and are referred to as site 1, site 2, site 3 and site 4 respectively. In the context of the present invention, typically, although not exclusively, at least one exposed loop site has an insertion. It can be appreciated that to facilitate generation of a more potent or, alternatively a broad-spectrum capsomere vaccine, one, two, three or four sites may comprise an insertion. This equally applies to capsomeres other than VP1 capsomeres.

Preferably, one, two or three exposed loops comprise an insertion. More preferably, the one or more exposed loops comprising an insertion are selected from the group consisting of site 1, site 3 and site 4. In more preferred embodiments, the one or more exposed loops comprising an insertion are selected from the group consisting of site 1 and site 4: Preferable examples of suitable VP1 chimeras of the present invention are provided in the Examples section and in particular, FIGS. 2, 6, 12, 13, 14 and 20.

In light of the foregoing it would be readily appreciated that the present invention contemplates isolated nucleic acids encoding isolated proteins, or fragments thereof, of the present invention.

The term "nucleic acid" as used herein designates single- or double-stranded mRNA, RNA, cRNA and DNA inclusive of cDNA, genomic DNA and DNA-RNA hybrids. Nucleic acids may also be conjugated with fluorochromes, enzymes and peptides as are well known in the art.

The term "gene" is used herein to describe a discrete nucleic acid locus, unit or region within a genome that may comprise one or more of introns, exons, splice sites, open reading frames and 5' and/or 3' non-coding regulatory sequences such as a polyadenylation sequence.

The present invention also contemplates nucleic acids that have been modified such as by taking advantage of codon sequence redundancy. In a more particular example, codon usage may be modified to optimize expression of a nucleic acid in a particular organism or cell type. The invention also contemplates use of modified purines (for example, inosine, methylinosine and methyladenosine) and modified pyrimidines (for example, thiouridine and methylcytosine) in nucleic acids of the invention.

It will be well appreciated by a person of skill in the art that the isolated nucleic acids of the invention can be conveniently prepared by a person of skill in the art using standard protocols such as those described in Chapter 2 and Chapter 3 of CURRENT PROTOCOLS IN MOLECULAR BIOLOGY (Eds. Ausubel et al. John Wiley & Sons NY, 1995-2008).

In one particular embodiment, an isolated nucleic acid of the present invention is operably-linked to one or more regulatory nucleotide sequences in a genetic construct. A person skilled in the art will appreciate that a genetic construct is a nucleic acid comprising any one of a number of nucleotide sequence elements, the function of which depends upon the desired use of the construct. Uses range from vectors for the general manipulation and propagation of recombinant DNA to more complicated applications such as prokaryotic or eukaryotic expression of the isolated nucleic acid. Typically, although not exclusively, genetic constructs are designed for more than one application. By way of example only, a genetic construct whose intended end use is recombinant protein expression in a eukaryotic system may have incorporated nucleotide sequences for such functions as cloning and propagation in prokaryotes in addition to sequences required for expression. An important consideration when designing and preparing such genetic constructs are the required nucleotide sequences for the intended application.

In view of the foregoing, it is evident to a person of skill in the art that genetic constructs are versatile tools that can be adapted for any one of a number of purposes. Methods for the generation of said genetic constructs are well known to those of skill in the art.

In a preferred embodiment, the genetic construct is an expression construct which is suitable for recombinant expression. Preferably, the expression construct comprises at least a promoter and in addition, one or more other regulatory nucleotide sequences which are required for manipulation, propagation and expression of recombinant DNA.

In particular aspects, the invention contemplates an expression construct comprising an isolated nucleic acid, operably-linked to one or more regulatory nucleotide sequences in an expression vector. A person skilled in the art will appreciate that the isolated nucleic acid may be inserted into the expression vector by a variety of recombinant techniques using standard protocols as for example described in Sambrook et al., MOLECULAR CLONING, A Laboratory Manual (Cold Spring Harbor Press, 1989), which is incorporated herein by reference.

An "expression vector" may be either a self-replicating extra-chromosomal vector such as a plasmid, or a vector that integrates into a host genome, inclusive of vectors of viral origin such as adenovirus, lentivirus, poxvirus and flavivirus vectors as are well known in the art.

By "operably linked" is meant that said regulatory nucleotide sequence(s) is/are positioned relative to the recombinant nucleic acid of the invention to initiate, control, regulate or otherwise direct transcription and/or other processes associated with expression of said nucleic acid.

Regulatory nucleotide sequences will generally be appropriate for the host cell used for expression. Numerous types of appropriate expression vectors and suitable regulatory sequences are known in the art for a variety of host cells.

Preferable vectors include any of the well known prokaryotic expression vectors, recombinant baculoviruses, COS cell specific vectors, vaccinia recombinants, or yeast-specific expression constructs. Among expression vectors preferred for use in cells of prokaryotic origin include pQE60 available from Qiagen, pGEX series of vectors available from GE Life Sciences and pET vector system available from Novagen.

Typically, said one or more regulatory nucleotide sequences may include, but are not limited to, promoter sequences, leader or signal sequences for secretion of a translated protein, ribosomal binding sites, transcriptional start and termination sequences, translational start and termination sequences, splice donor/acceptor sequences, enhancer or activator sequences and nucleic acid packaging signals.

Preferably, said promoter is operable in a bacterial cell. Non-limiting examples include T7 promoter, tac promoter and T5 promoter.

Inducible/repressible promoters (such as tet-repressible promoters and IPTG-, alcohol-, metallothionine- or ecdysone-inducible promoters) are well known in the art and are contemplated by the invention, as are tissue-specific promoters such as α-crystallin promoters. It will also be appreciated that promoters may be hybrid promoters that combine elements of more than one promoter (such as SRα promoter).

The expression construct may also include a fusion partner (typically provided by the expression vector) so that the protein (or fragment thereof) of the invention is expressed as a fusion protein with said fusion partner, as hereinafter described.

Expression constructs may also include a selection marker nucleic acid that confers transformed host cell resistance to a selection agent. Selection markers useful for the purposes of selection of transformed bacteria include bla, kanR and tetR while transformed eukaryotic cells may be selected by markers such as hygromycin, G418 and puromycin, although without limitation thereto.

Expression constructs may be introduced into cells or tissues, inclusive of cells capable of recombinant protein production, by any of a number of well known methods typically referred to as "transfection" "transduction", "transformation" and the like. Non-limiting examples of such methods include transformation by heat shock, electroporation, DEAE-Dextran transfection, microinjection, liposome-mediated transfection (e.g. lipofectamine, lipofectin), calcium phosphate precipitated transfection, viral transformation, protoplast fusion, microparticle bombardment and the like.

It is readily contemplated that any recombinant protein expression system may be used for the present invention such as bacterial, yeast, plant, mammalian and insect-based expression systems but is not limited thereto.

In one preferred embodiment, recombinant protein expression occurs in cells of prokaryotic origin. Suitable host cells for recombinant protein expression are bacterial cells such as *Escherichia coli* (BL21 and various derivative strains thereof which have been optimised for certain applications, such as Rosetta and DE3, for example) and *Bacillus subtilis*, although without limitation thereto.

In another preferred embodiment, recombinant expression occurs in insect cells which are suited to viral-based recombinant expression e.g. Sf9 cells.

Formation of capsomeres can be monitored by electron microscopy or other techniques including size-exclusion chromatography optimally hyphenated with light scattering and, in instances wherein capsomeres are comprised of fusion proteins, the presence of various protein components in the assembled capsomere can be confirmed by Western blot analysis using specific antisera.

Pharmaceutical Compositions and Methods Thereof

In broad aspects, the invention relates to pharmaceutical compositions and therapeutic/prophylactic methods comprising the capsomeres as hereinbefore described.

In other general aspects, the invention relates to pharmaceutical compositions and methods of augmenting an immune response, comprising an immunogenic protein of interest and an adjuvant selected from the group consisting of a protein-stabilised surfactant emulsion adjuvant, a solid particle substantially-free of an immunogen of interest and a virus-like particle.

In preferred embodiments, the methods include inducing or augmenting an antigen specific immune response in a subject. Methods of the present invention may be prophylactic or therapeutic.

In a preferred embodiment, the pharmaceutical composition of the present invention is an immunogenic composition.

More preferably, the immunogenic composition is an immunotherapeutic composition.

In a particular preferred embodiment, the immunotherapeutic composition is a vaccine. Any suitable procedure is contemplated for producing vaccine compositions. Exemplary procedures include, for example, those described in New Generation Vaccines (1997, Levine et al., Marcel Dekker, Inc. New York, Basel, Hong Kong), which is incorporated herein by reference. Alternatively, a vaccine may be in the form of a nucleic acid vaccine and in particular, a DNA vaccine. A useful reference describing DNA vaccinology is DNA Vaccines, Methods and Protocols, Second Edition (Volume 127 of Methods in Molecular Medicine series, Humana Press, 2006) and is incorporated herein by reference.

According to the methods using a protein-stabilised surfactant emulsion adjuvant, a solid particle substantially-free of an immunogen of interest and a virus-like particle as an adjuvant to immunogens of interest, and preferably capsomeres, the immunogen is mixed with the adjuvant and suitably this co-formulation is administered to the subject without further purification and/or processing prior to administration and without covalent attachment.

Adjuvants

As well as the use of conventional adjuvants, the invention particularly contemplates in other general aspects of the present invention relate to methods and compositions for augmenting an immune response against an immunogen of interest, and preferably a capsomere carrying one or more immunogens of interest and in particular, a chimeric capsomere as hereinbefore described by administration of the immunogen of interest with an adjuvant selected from the group a protein-surfactant stabilised emulsion, a solid particle substantially-free of the immunogen of interest and a virus-like particle. According to preferred forms, once combined the immunogen of interest and the adjuvant does not undergo further processing, modification and/or purification prior to administration. According to particularly preferred forms, after combining the immunogen of interest and adjuvant, we do not expect the immunogen of interest and adjuvant do not become substantially associated thus most of the immunogen remains in solution and not be attached to the surface of the adjuvant.

By “augment” or “augmenting” is meant to enhance, stimulate, boost, potentiate or otherwise improve an immune response against an immunogen. By “augment” is not meant to initiate an immune response but rather, increase or potentiate an immune response. The response is a immunogen-specific immune response and may be a neutralising, B-cell and/or T-cell response. Preferably, it is an IgG response.

As used herein, the term “adjuvant” has its ordinary meaning as understood by those in the art. For example, an adjuvant can be defined as a substance that increases the ability of an immunogen to stimulate an immune response against the immunogen in the subject. In particular embodiments, the adjuvant increases the immune response against the immunogen by at least about 2, 3, 4, 5, 10, 15, 20, 30, 40, 50, 60, 75, 100, 150, 500, 1000-fold or more. In other embodiments, the adjuvant reduces the amount of immunogen required to achieve a particular level of immune response (cellular and/or humoral and/or mucosal), e.g., a reduction of at least about 15%, 25%, 35%, 50%, 65%, 75%, 80%, 85%, 90%, 95%, 98% or more. An adjuvant can further be a substance that prolongs the time over which an immune response, optionally protective immune response, is sustained (e.g., by at least about a 2-fold, 3-fold, 5-fold, 10-fold, 20-fold longer time period or more).

Protein-Surfactant Stabilised Emulsion Adjuvant

As used herein, the term “emulsion” refers to a suspension or dispersion of a first liquid suspended or dispersed in a second liquid in which the first liquid is poorly soluble or non-miscible. The first liquid is referred to as the dispersed phase and the second liquid is referred to as the continuous phase. The dispersed phase may form droplets which are dispersed throughout the continuous phase in a heterogenous or homogeneous manner. Illustrative examples of emulsions include oil-in-water emulsions in which the oil forms the dispersed phase and the water forms the continuous phase, and water-in-oil emulsions in which the water forms the dispersed phase and the oil forms the continuous phase. In addition, “multiple emulsions” may be formed in which droplets of a first discontinuous phase contain smaller droplets of a second discontinuous phase, which may or may not be similar in composition to the continuous phase containing the first discontinuous phase. Illustrative examples of multiple emulsions include water-in-oil-in-water emulsions in which the oil forms the first discontinuous phase and water forms the second discontinuous phase, and oil-in-water-in-oil emulsions in which the water forms the first discontinuous phase and oil forms the second discontinuous phase. Suitably, the emulsion of the present invention may be a water-in-oil (W/O) emulsion or an oil-in-water (O/W) emulsion.

The protein-surfactant stabilised emulsions of the present invention are formed from a protein-surfactant that, when emulsified to form the adjuvant, will substantially prevent the breakdown of the capsomere structure. The protein-surfactants are emulsified in an oil phase and suitably, with an appropriate buffer. In preferred embodiments, the protein-stabilised surfactant emulsion of the present invention is an oil-in-water emulsion (O/W).

It will be appreciated that the protein component of the protein-surfactant stabilised emulsion may be a peptide, a polypeptide or a mixture of the two.

Particularly excluded from these embodiments of the invention are emulsion adjuvants (and more preferably emulsion adjuvants with a mean size of less than 200 nm) which comprise non-proteinaceous surfactants and in particular, one or more of a chemical surfactants, a lipid or synthetic chemical polymer and/or are specifically formulated to destroy and inactivate virus structure. Preferably, the emulsion adjuvant is not a squalene-based adjuvant and more preferably, is not MF59 and its equivalents or alternatives. In other particular embodiments, the emulsion is not an emulsion adjuvant which kills or inactivates viruses (such as by membrane structure destabilisation) such as $W_{80}$5EC (supplied by NanoBio Corporation (Ann Arbor, Mich.)). $W_{80}$5EC is an oil-in-water emulsion manufactured by high speed emulsification and typically, although not exclusively, contains Tween 80, ethanol, soybean oil, cetylpyridinium chloride and water.

The emulsion of the present invention can be prepared by conventional techniques as is known in the art.

Particular advantages conferred by the protein-surfactant stabilised emulsion employed in the present invention include that it is a “structure-friendly” adjuvant meaning that it substantially retains the structure of the capsomere. This advantage stems from inclusion of a peptide or protein surfactant molecule in an appropriate buffer and an oil phase that will not break down capsomere structure. This is unlike other adjuvants such as $W_{80}$5EC which destroys and inactivates virus structure. The protein stabilised surfactant emulsion ensures efficient antigen presenting cells (APCs) uptake due to, at least in part, an average emulsion size of less than 200 nm, which is similar to some viruses. Furthermore, the emulsion is manufactured from biodegradable compounds, and is thus less toxic and less reactogenic than some other emulsion adjuvants.

Protein surfactants of the present invention may be designed (or otherwise engineered) or alternatively, may be naturally-derived. Designed peptide surfactants (may be commonly referred to as ‘pepfactants’) are facially amphipathic molecules that self-assemble at fluid interfaces to give cohesive films stabilizing foams and emulsions. A change in the bulk solution conditions can switch off the interfacial film, leading to rapid foam or emulsion collapse. Designed peptide surfactants can be genetically engineered and produced using standard methods. Reference is made to International Publication No. 2006/089364 (in the name of the University of Queensland), Dexter et al (2006) *Nature Materials* 5: 502-506 and Dexter and Middelberg (2008) *Industrial & Engineering Chemistry Research,* 4717: 6391-6398 for non-limiting examples of designed peptide surfactants that suitable for use in the present invention and methods of production thereof. International Publication No. 2006/089364, Dexter et al (2006) and Dexter and Middelberg (2008) are incorporated herein by reference.

Preferably, the peptide surfactant comprises a peptide sequence selected from MKQLADSLHQLARQVSRLEHA (SEQ ID NO: 48; common name AM1) and MKQLADSLMQLARQVSRLESA (SEQ ID NO: 49; common name Lac21). More preferably, the peptide sequence is MKQLADSLHQLARQVSRLEHA (SEQ ID NO: 48).

Other preferred embodiments contemplate a peptide-surfactant comprising a plurality of peptides wherein either the same peptide or different peptides associate to create a peptide-surfactant. By way of example, Middelberg and Dimitrijev-Dwyer (2011) *Chem Phys Chem* 12:1426-1429 (incorporated herein by reference) describes a peptide-surfactant (referred to as DAMP4) which is composed of four AM1 peptide surfactant units joined together to create a suitable peptide-surfactant for use in the present invention.

Protein hydrolysates are an example of a naturally-derived peptide surfactant involves digesting native proteins to obtain short peptide sequences that may have useful surface activity. In this approach, intact proteins are subjected to chemical or enzymatic hydrolysis; often with a reagent that has selectivity for particular sequence sites within the protein. After peptide bond cleavage has proceeded to a given level, usually involving cleavage of 1-10% of all monomer links, the reaction is terminated. The partial digest, a highly complex mixture, is subjected to tests to determine its surfactant properties and may undergo fractionation to obtain peptides with improved functionality relative to the native protein or the initial mixture. In rare cases, it may be possible to attribute the improved surfactant properties to a particular peptide or peptides in the hydrolysate. Proteins used for the preparation of surfactant peptide mixtures are generally low-cost food proteins, including casein, whey, soy, seed residues, and fishery by products.

It is commonly, although not universally, observed that the surfactant properties of native proteins are improved by partial hydrolysis. Because different proteolytic enzymes have different cleavage site specificities, the products of partial digestion with each enzyme will be different for the same starting protein, even at the same degree of hydrolysis. For a given protein/protease combination, there appears to exist an optimal degree of hydrolysis beyond which surfactant functionality decreases, as amphipathic peptides are degraded to single amino acids. In some cases, the surfactant properties of short peptides can be improved by chemical acylation. Fractionation of peptide products may be achieved by ultrafiltration, selective precipitation or chromatography, based on differences in size, hydrophobicity, charge, or solubility. Analysis of the products of digestion has identified peptide structural features important to improved surfactant properties. However, for good surface activity, peptides may contain distinct clusters of hydrophobic and hydrophilic residues. It appears to be particularly favorable if they possess distinct hydrophobic and hydrophilic faces in an α-helical or β-sheet conformation. Sequence patterns suitable to this outcome are well-known.

Digest peptides may be smaller than 2 kDa or as high as 7 kDa or more, as can be deemed suitable by a person of skill in the art.

The protein-surfactant stabilised emulsion is preferably formulated with a pharmaceutically-acceptable oil. Non-limiting examples of suitable pharmaceutically-acceptable oils include oils derived from plant fatty acids and more suitably, triglycerides of the fractionated plant fatty acids C8 and C10 and more particularly, saturated coconut and palm-kernel oil-derived caprylic and capric fatty acids and glycerin or propylene glycol. Such oils are sold under trade name of MIGLYOL® 810, 812, 818, 829, 840 by Sasol (Germany).

The protein-surfactant stabilised emulsion of the present invention preferably has a mean size (particle size) that is equivalent to the size of a virus particle. Preferably, protein-surfactant stabilised emulsion has a mean size of less than about 300 nm, 200 nm or less. In particularly preferred embodiments, the protein-surfactant stabilised emulsion has a mean size of less than 200 nm.

A Solid Particle Substantially-Free of an Immunogen of Interest as an Adjuvant

According to these embodiments, the invention is predicated, at least in part, on the finding that it is not necessary to covalently attach an immunogen either in or on the surface of a solid particle (sometimes referred to colloquially herein as "nanoparticles"), and in particular a solid silica particle, to act as an effective adjuvant for the immunogen. The invention is also predicated on the finding that it is not necessary to achieve a high level of saturation of the surface of the solid particle with immunogen for there to be an effective adjuvanting effect the surface of the solid particle can be substantially free of the immunogen of interest, with most of the immunogen present in the administered sample being in an unconjugated state and thus free in solution. As described in the Examples section herein, the inventors have demonstrated that the co-administration of capsomeres in presence of solid silica particles (in which there is no substantial association between the solid silica particle and the capsomere) gives a better immune response than administration of capsomeres alone. This is a surprising and unexpected result and directly challenges the dogma that an immunogen must be attached to a particle to give a positive benefit. Moreover, the immunogen is not covalently attached to the solid particle and any association that occurs is through non-covalent linkage. In preferred embodiments, after combining the immunogen and solid particle, a substantial fraction of the immunogen remains in solution and not attached to the surface of the solid particle. It is contemplated that a small fraction of the immunogen may non-specifically bind through, for example, non-covalent bonds, to the solid particle.

By "solid particle substantially-free of an immunogen of interest" is meant a particulate structure not found in nature, and is preferably pre-fabricated, formed from one or more solid carrier materials and is either free or substantially-free of an immunogen of interest associated with its surface. The present invention avoids specific conjugation or attachment of the immunogen of interest to the solid particle for use as an adjuvant. It may be that the solid particle is substantially-free of covalently associated immunogen of interest either at its surface, encapsulated therein or a combination thereof. That is, the solid particles of the invention are not used for delivery of the substantial amount of immunogen since the immunogen of interest is not covalently attached to the solid particle since the immunogen of interest is not conjugated to the particle and any association that occurs is through non-covalent linkage. Accordingly to those embodiments that contemplate capsomeres, the immunogen carrier or interest is the capsomere and preferably the chimeric capsomere as herein described.

By "substantially-free of an immunogen of interest", is where about 15%, preferably about 10%, and more preferably about 5%, 4%, 3%, 2%, 1% or lower of the available immunogen of interest is bound to the solid particle. It is contemplated that in certain embodiments, the immunogen of interest may constitute no more than about 50%, preferably no more than about 40% and even more preferably no more than about 30%, about 25%, 20%, 15%, 10%, 5% or lower of the surface coverage that would correspond to a closely packed saturated monolayer of the immunogen on the surface of the solid particle. Surface coverage may be defined an a mg/$m^2$ basis and according to these embodiments, reference is made to Daly et al, *Langmuir* (2003), 19, 3848-3857, which provides useful methodology for measuring protein adsorption to a solid surface and is incorporated herein by reference.

In particular embodiments, the pharmaceutical composition comprises a solid particle substantially-free of an immunogen of interest and substantially unbound antigen. By "substantially unbound immunogen", in relation to this invention, is where the majority of the immunogen remains in solution when the solid particle as an adjuvant and immunogen are combined, such that less than 20% of the immunogen capable of associating with the solid particle binds to the surface and preferably not more than 10% and more preferably not more than 9%, 8%, 7%, 6%, 5% or lower.

Routine assays, apparent to the person of skill in the art, could be used to determine whether and at what level the immunogen of interest is associated with solid particles, including but not limited to separation into distinct fractions by free flow of the formulation within an electric field, isotherm adsorption, or techniques such as sedimentation rate analysis which are particularly suited to non-particulate antigens, followed by assaying for immunogen of interest in the fractions.

The term solid in the context of the present invention is meant a material that is characterized by structural rigidity and resistance to changes of shape or volume. The "solid particle" of the present invention preferably has a solid surface/core and may be porous or non-porous. The solid particles may be a variety of different shapes including but not limited to, spheroidal, cubic, pyramidal, oblong, cylindrical, toroidal and the like.

Included within the scope of a solid particle for use of as an adjuvant are particles differentiated by size such as a nanoparticle whose mean particle size falls within the nanoscale and a microparticle whose mean particle size falls within the micron-scale. Suitably, the particles are no larger than the upper limit of the micron scale. In particular embodiments, the solid particle has a mean particle size of less than 1 micron. In some preferred embodiments, the solid particles used as an adjuvant of the invention have a mean particle diameter size of less than 200 nm. In other preferred embodiments, the mean particle diameter size is between about 5 nm and about 100 μm, more preferably between about 50 nm and 50 μm, even more preferably about 100 nm and 20 μm, yet even more preferably between 150 nm and 10 μm and even more preferably, about 200 nm. It is contemplated that the mean particle diameter size of the unconjugated solid particle is less than about 50 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 μm, 1.5 μm, 2 μm, 2.5 μm, 3 μm, 4 μm, 5 μm, 10 μm, 15 μm, 20 μm, 25 μm, 30 μm, 40 μm, 50 μm, 60 μm, 70 μm, 80 μm, 90 μm and 100 μm.

In particular preferred embodiments, the solid particle of the invention has a mean diameter size of between about 40 nm and 60 nm.

In particular embodiments, the solid particle used as an adjuvant is a non-polymeric with a mean particle size of less than 1 micron.

The solid particles of the invention may be made from degradable and non-degradable carrier materials. Degradable materials include synthetic polymers such as polycyanoacrylate, poly(D, L-lactide), poly(lactide-co-glycolide) (PLGA) and poly(lactic acid); natural polymers such as polysaccharides inclusive of chitosan, gelatine, and sodium alginate, although without limitation thereto. Non-degradable carrier materials include latex, silica, polystyrene and metal such as gold and silver. Particles can be prepared by different techniques, such as spray drying, freeze drying or solvent evaporation as will be known to a person of skill in the art.

The invention contemplates solid particles as adjuvants that have been surface-modified. For example, a solid particle can be polymer-coated silica where the surface has been designed or engineered using techniques known in the art to modify the surface in such a way that protein adsorption is resisted. This same approach could be used for polymer particles.

In particularly preferred embodiments, the solid particles of the invention are manufactured from silica. Such solid silica particles are available commercially from Polysciences, Inc. In particularly, preferred embodiments, the invention contemplates a solid particle substantially-free of an immunogen of interest being a silica particle of a mean diameter size of less than about 250 nm, more preferably less than about 100 nm and even more preferably having a mean diameter size of less between about 40 nm and 60 nm.

According to preferred methods of use, the immunogen of interest is not substantially absorbed to or encapsulated within the solid particle. Preferably, once combined the immunogen of interest and the adjuvant does not undergo further processing, modification and/or purification prior to administration to a subject.

The state of the particle may be ascertained by methods such as isotherm calorimetry, dynamic light, x-ray scattering, zeta potential measurement or indirectly by HPLC analysis of formulated supernatant as are known in the art.

According to particularly preferred embodiments that relate to utilising a solid particle substantially-free of an immunogen of interest as an adjuvant, the solid particle and the immunogen of interest is combined as a pharmaceutical composition without further processing prior to administration, such that the bound and unbound immunogen of interest are not separated. Therefore when administered, the pharmaceutical composition comprises a substantial proportion of unbound immunogen of interest (and thereby present free in the solution) and a proportion of the immunogen of interest is bound to the solid particle. In particularly preferred embodiments, the pharmaceutical composition is formulated by combining a solid particle and an immunogen of interest without further processing prior to administration and comprises a solid particle in which the immunogen of interest is less than 50% of surface saturation of the particle.

Virus-Like Particles (VLPs) as Adjuvants

The present inventors assert that virus-like particles can act as potent adjuvants to enhance an immune response, which effect is unrelated to their ability to act as vaccine vectors. The VLP adjuvants of the invention can stimulate and enhance an immune response against an immunogen that is independent of the VLP adjuvant, i.e., is not presented by the VLP adjuvant or expressed by the VLP adjuvant. That is according to the present invention, VLPs are not used as an immunogen against the parental virus or as an antigen carrier against the targeted virus. In the context of the present invention, the VLP is used as an immunisation partner to capsomere, i.e. as an adjuvant instead of as an immunogen or antigen carrier. Suitably, the VLP is an unconjugated VLP. In particularly preferred embodiments, the VLP adjuvant is a wild-type VP1 VLP. The conjugation state of the particle may be ascertained by methods such as calorimetry, size-exclusion chromatography or HPLC as are known in the art.

In particular embodiment, by "pharmaceutically-acceptable carrier, diluent or excipient" is meant a solid or liquid filler, diluent or encapsulating substance that may be safely used in systemic administration. Depending upon the particular route of administration, a variety of carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions, emulsifiers, isotonic saline and salts such as mineral acid salts including hydrochlorides, bromides and sulfates, organic acids such as acetates, propionates and malonates and pyrogen-free water.

A useful reference describing pharmaceutically acceptable carriers, diluents and excipients is Remington's Pharmaceutical Sciences (Mack Publishing Co. N.J. USA, 1991) which is incorporated herein by reference.

Any safe route of administration may be employed for providing a patient with the composition of the invention. For example, enteral, oral, rectal, parenteral, sublingual, buccal, intravenous, intra-articular, intra-muscular, intradermal, subcutaneous, inhalational, intraocular, intraperitoneal, intracerebroventricular, transdermal and the like may be employed.

Dosage forms include tablets, dispersions, suspensions, injections, solutions, oils, syrups, troches, capsules, suppositories, aerosols, transdermal patches and the like. These dosage forms may also include injecting or implanting controlled releasing devices designed specifically for this purpose or other forms of implants modified to act additionally in this fashion. Controlled release of the therapeutic agent may be effected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be effected by using other polymer matrices, liposomes and/or microspheres.

Compositions of the present invention suitable for enteral, oral or parenteral administration may be presented as discrete units such as capsules, sachets or tablets each containing a pre-determined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more agents as described above with the carrier which constitutes one or more necessary ingredients. In general, the compositions are prepared by uniformly and intimately admixing the agents of the invention with liquid carriers or finely divided solid carriers or both, and then, if necessary, shaping the product into the desired presentation.

The above compositions may be administered in a manner compatible with the dosage formulation, and in such amount as is pharmaceutically-effective. The dose administered to a patient, in the context of the present invention, should be sufficient to effect a beneficial response in a patient over an appropriate period of time. The quantity of agent(s) to be administered may depend on the subject to be treated inclusive of the age, sex, weight and general health condition thereof, factors that will depend on the judgement of the practitioner.

It will also be appreciated that treatment methods and pharmaceutical compositions may be applicable to prophylactic or therapeutic treatment of mammals, inclusive of humans and non-human mammals such as livestock (e.g. horses, cattle and sheep), companion animals (e.g. dogs and cats), laboratory animals (e.g. mice, rats and guinea pigs) and performance animals (eg racehorses, greyhounds and camels), although without limitation thereto.

So that the invention may be readily understood and put into practical effect, the following non-limiting Examples are provided.

EXAMPLES

Example 1

Construction of Generic Vectors Carrying VP1 Sequences Able to Accept Antigenic Peptide Sequences on the N-Terminal and/or C-Terminal and/or the Surface Loops Murine polyomavirus VP1 sequence (GenBank accession number: M34958) was cloned between the BamHI and XhoI sites within the multiple cloning site of the commercial vector pGEX-4T-1 (GE healthcare). Generic vectors carrying VP1 sequences able to accept antigenic sequences on the surface-exposed loops of polyomavirus VP1 were previously constructed and documented in International Publication No. WO/2008/040060.

The amino acid sequence of VP1 present in the generic vectors is depicted in FIG. 1. S1 of VP1 was mutated to include NaeI restriction site (LATSDTED (SEQ ID NO: 44) mutated to LATSAGTED (SEQ ID NO: 45)). S4 of VP1 was mutated to include AfeI restriction site (TRNYDV (SEQ ID NO: 46) mutated to TRSAYDV (SEQ ID NO: 47)). A delta N28 and delta C63 VP1 along with mutated S1 and S4 sites is generated by recloning the truncated VP1 S1/S4. The first 28 amino acid residues of VP1 and the last 63 amino acids of VP1 are removed to generate the truncated VP1 S1/S4. Restriction site PmlI is introduced at the N-terminus of truncated VP1 S1/S4 and restriction site SnaBI is introduced at the C-terminus during the recloning.

Resulting generic vectors with modified VP1 sequences to enable the insertion of one or multiple foreign peptides are: pGEX4T1-VP1 S1, pGEX4T1-VP1 S4, pGEX4T1-VP1 S1/S4 and pGEX4T1-VP1 dNdC 0000.

Example 2

Production of Chimeric VP1 Capsomeres with Antigenic Peptide Sequences on the N-Terminal, C-Terminal and the Surface Loops Construction and Sequencing of Vector Carrying HA Epitope from Loop A of H1N1:

*E. coli* codon optimised oligonucleotides were designed for epitope A (17 amino acids, DSNKGVTAACPHAGAKS (SEQ ID NO: 32)) for insertion into generic vector pGEX4T1-VP1 dNdC 0000. The sequence of epitope A is of H1N1 (A/California/07/2009).

Resulting constructs carrying HA epitope A is pGEX4T1-VP1 dNdC 1011A (FIG. 2).

Expression of Chimeric VP1 dNdC 1011A:

VP1 dNdC 1011A protein were expressed in Rosetta (DE3) pLysS (Novagen) as a glutathione-s-transferase-VP1-dNdC 1011A (GST-VP1-dNdC 1011A) fusion protein using the pGEX-4T-1-VP1 dNdC 1011A expression vector. For solid agar medium, 15 g/L of agar was added to Luria-Bertani (LB) medium (10 g/L tryptone, 5 g/L yeast extract, 10 g/L NaCl, pH 7.0). Liquid medium used for cell cultures was Terrific Broth (TB) containing 12 g/L peptone, 24 g/L yeast extract, 0.4% (v/v) glycerol, 2.31 g/L $KH_2PO_4$ and 12.54 g/L $K_2HPO_4$. All media used were supplemented with 50 μg/mL of ampicillin and 34 μg/mL of chloramphenicol. Overnight cultures were set up by inoculating single colonies of the transformed, cells into 5 mL of TB medium and cultivated at 30° C. on a rotary shaker at 180 rpm. After incubation of 16 hours, the overnight cultures were diluted 1000 times into 400 mL cultures in 2 L baffled flasks. These cultures were cultivated to an $OD_{600}$ of 0.5 at 37° C. and then cooled to 26° C. under running tap water and subsequently induced with IPTG at final concentration of 0.2 mM. The induced cultures were then cultivated at 26° C. for a further 16 hours and harvested by centrifugation at 8000 g, 4° C. for 30 mins.

Purification of Chimeric VP1 dNdC 1011A:

Two pellets from 2×400 mL cultures were re-suspended in 40 mL of buffer L (200 mM NaCl, 40 mM Tris, 5 mM dithiothreitol, 1 mM EDTA, 5% v/v glycerol, pH 8 with HCl). The cell suspension was sonicated at output 30 using a Branson Sonifier 450 (Sonifier, USA) for 4×40 seconds. The resulting cell lysate was centrifuged at 27000 g, 4° C. for 30 mins and the supernatant which contained soluble chimeric proteins was filtered through an 0.45 μm syringe filters (Millipore) giving a recovery of ~35 mL.

Figure 3B:
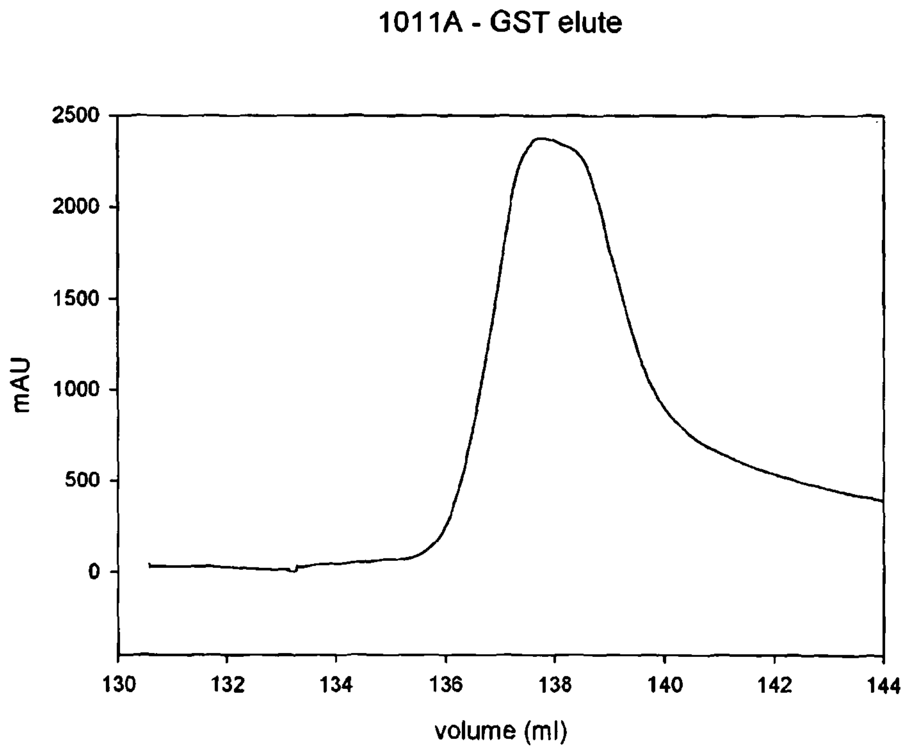

Protein purification was performed with an Äkta Explorer system from GE Healthcare. GST-VP1 dNdC 1011A in the clarified lysate was captured using a GSTrap™ HP 5 mL column from GE Healthcare pre-equilibrated with buffer L (illustrated in FIG. 3A). The bound GST fusion proteins was eluted with elution buffer (Buffer L with 10 mM reduced glutathione) as illustrated in FIG. 3B. Eluted samples were stored at −80° C. until required.

Figure 4:
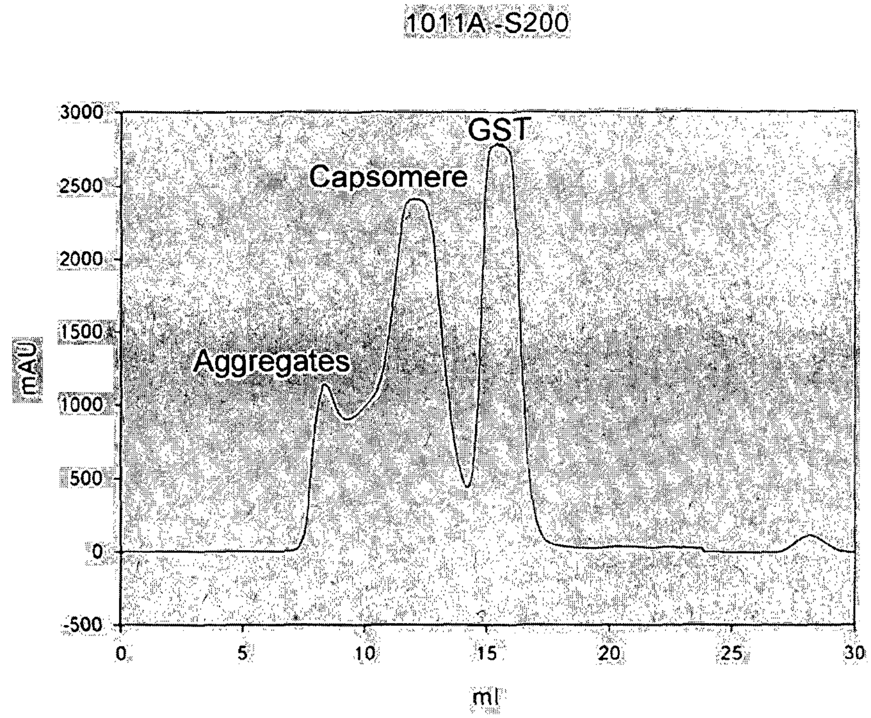
FIG. 4 S200 purification of chimeric VP1 dNdC 1011A.

40 μL of Thrombin was added to 1 mL of purified GST fusion proteins followed by 2 hours incubation at room temperature. 1 mL of thrombin treated capsomere was injected onto a Superdex S200 10/300 GL size exclusion column (GE Healthcare) equilibrated in buffer L, to separate capsomeres from aggregates, GST and thrombin (FIG. 4). Capsomere fractions eluting at a volume of 11-13 mL were pooled, aliquoted and frozen at −80° C. for subsequent use. The capsomere sample was analysed by TEM (data not shown) which showed that the sample comprised distinct non-aggregated and non-assembled capsomeres suitable for use.

Animal Testing of Chimeric VP1 dNdC 1011A Capsomeres: Adjuvant Formulation

Adjuvanted samples were prepared by mixing protein sample with alum adjuvant in 1:1 volume ratio, followed by incubation for one hour at room temperature on a roller mixer prior to immunisation.

Mice Immunisation

Mice were immunised with vaccine sample containing 50 μg of protein (<2 EU/ml) and 250 μg of alum adjuvant in a total of 50 μl volume through subcutaneous injections into the tail bases using 25-gauge needles. After the first immunisation on day 0, two other immunisations were given to the mice on days 21 and 42. Blood samples were taken by tail snip before the first immunisation (day 0), as well as on days 14, 35 and 56.

| | |
|---|---|
| Groups | 1. PBS + alum<br>2. VP1dC63<br>3. VP1dC63 + alum<br>4. VP1dNdC 1011A + alum |
| Dose | 50 μg of capsomeres |
| Volume | Total 50 μL |
| Adjuvant | Alum (250 μg) |
| Immunisation and bleeds | Inject days: 0, 21, 42<br>Bleed days: 0, 14, 35, 56 |

ELISA

Figure 5:
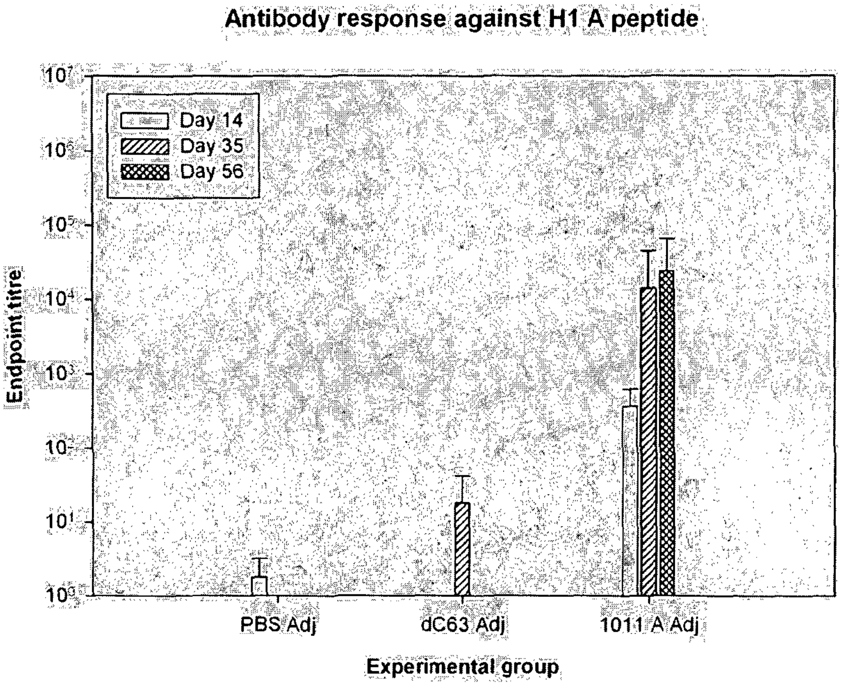
FIG. 5 Antibody response against H1 A peptide.

H1 A peptide at 10 μg/mL in carbonate coating buffer (50 mM $Na_2CO_3NaHCO_3$, pH 9.6) was adsorbed to 96-well NUNC immunoplates (Thermo Fisher Scientific, MA, USA), 1004 per well overnight at 4° C. Plates were blocked with PBST (137 mM NaCl, 2.7 mM KCl, 10.15 mM $Na_2HPO_4$, 1.76 mM $KH_2PO_4$, pH 7.4, 0.05% (v/v) Tween 20) containing 5% skim milk (37° C., 90 min) and washed twice with PBST. Plates were incubated with mouse sera at 100-fold dilution followed by 2-fold serial dilutions (90 min, 37° C.). After washing 4 times with PBST, HRP-conjugated goat anti-mouse antibody (Sigma-Aldrich, USA) was added at 10000-fold dilution (90 min, 37° C.). Plates were washed 4 times with PBST and developed (0.4 mg/ml o-Phenylenediamine dihydrochloride (Sigma-Aldrich, USA), 50 mM Phosphate citrate buffer, 0.03% sodium perborate) prior to absorbance measurement at 450 nm. End point titers were determined as the highest dilution of serum for which the OD was 3SD above the mean OD of blank wells. The end point titers of each group are shown in FIG. 5. Specific immune response against H1 A peptide is observed.

Construction of Vectors Carrying M2e:

*E. coli* codon optimised oligonucleotides were designed to insert M2e peptide (SLLTEVETPTRSEWECRCSDSSD (SEQ ID NO: 23)) into the generic vectors.

Resulting constructs carrying M2e are designated pGEX4T1-VP1 dNdC 1011M2e and pGEX4T1-VP1 dNdC 2022M2e. The sequence of M2e is of H1N1 (A/California/07/2009).

The amino acid sequences of VP1 dNdC 0000 with inserted peptides are exemplified in FIG. 6.

Figure 7A:
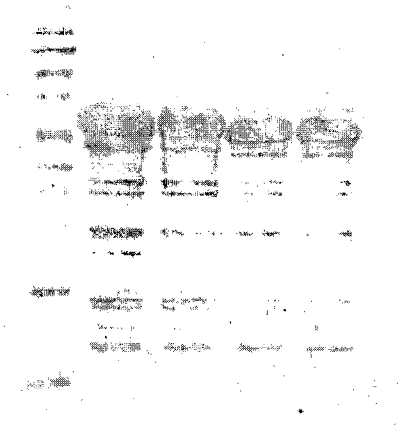
FIG. 7A SDS-gel electrophoresis analysis of expression. Lane designations from left to right: Lane 1: Protein molecular weight marker; Lane 2: Wildtype VP1 total expression; Lane 3: Wildtype VP1 soluble expression; Lane 4: 1011M2e total expression; Lane 5: 1011M2e soluble expression.
Figure 7B:
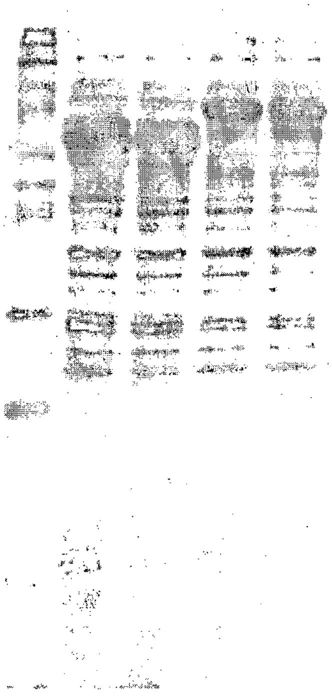
FIG. 7B Left to right: Lane 1: Protein molecular weight marker; Lane 2: Wildtype VP1 total expression; Lane 3: Wildtype VP1 soluble expression; Lane 4: 2022M2e total expression; Lane 5: 2022M2e soluble expression.

Expression of Chimeric VP1 dNdC 1011M2e and VP1 dNdC 2022M2e:

VP1 dNdC 1011M2e and VP1 dNdC 2022M2e proteins were expressed in Rosetta (DE3) pLysS (Novagen) as a glutathione-s-transferase-VP1-dNdC 1011M2e (GST-VP1-dNdC 1011M2e) and glutathione-s-transferase-VP1-dNdC63 1011M2e (GST-VP1-dNdC 2022M2e) fusion protein using the pGEX-4T-1-VP1 dNdC 1011M2e and pGEX-4T-1-VP1 dNdC 2022M2e expression vectors. For solid agar medium, 15 g/L of agar was added to Luria-Bertani (LB) medium (10 g/L tryptone, 5 g/L yeast extract, 10 g/L NaCl, pH 7.0). Liquid medium used for cell cultures was Terrific Broth (TB) containing 12 g/L peptone, 24 g/L yeast extract, 0.4% (v/v) glycerol, 2.31 g/L $KH_2PO_4$ and 12.54 g/L $K_2HPO_4$. All media used were supplemented with 50 μg/mL of ampicillin and 34 μg/mL of chloramphenicol. Overnight cultures were set up by inoculating single colonies of the transformed cells into 5 mL of TB medium and cultivated at 30° C. on a rotary shaker at 180 rpm. After incubation of 16 hours, the overnight cultures were diluted 1000 times into 400 mL cultures in 2 L baffled flasks. These cultures were cultivated to an $OD_{600}$ of 0.5 at 37° C. and then cooled to 26° C. under running tap water and subsequently induced with IPTG at final concentration of 0.2 mM. The induced cultures were then cultivated at 26° C. for a further 16 hours and harvested by centrifugation at 8000 g, 4° C. for 30 mins. The expression was analysed on SDS-PAGE (FIGS. 7A and 7B).

Purification of Chimeric VP1 dNdC 1011M2e and VP1 dNdC 2022M2e:

Two pellets from 2×400 mL cultures were re-suspended in 40 mL of buffer L (200 mM NaCl, 40 mM Tris, 5 mM dithiothreitol, 1 mM EDTA, 5% v/v glycerol, pH 8 with HCl). The cell suspension was sonicated at output 30 using a Branson Sonifier 450 (Sonifier, USA) for 4×40 seconds. The resulting cell lysate was centrifuged at 27000 g, 4° C. for 30 mins and the supernatant which contained soluble chimeric proteins was filtered through a 0.45 μm syringe filters (Millipore) giving a recovery of ~35 mL.

Figure 8A:
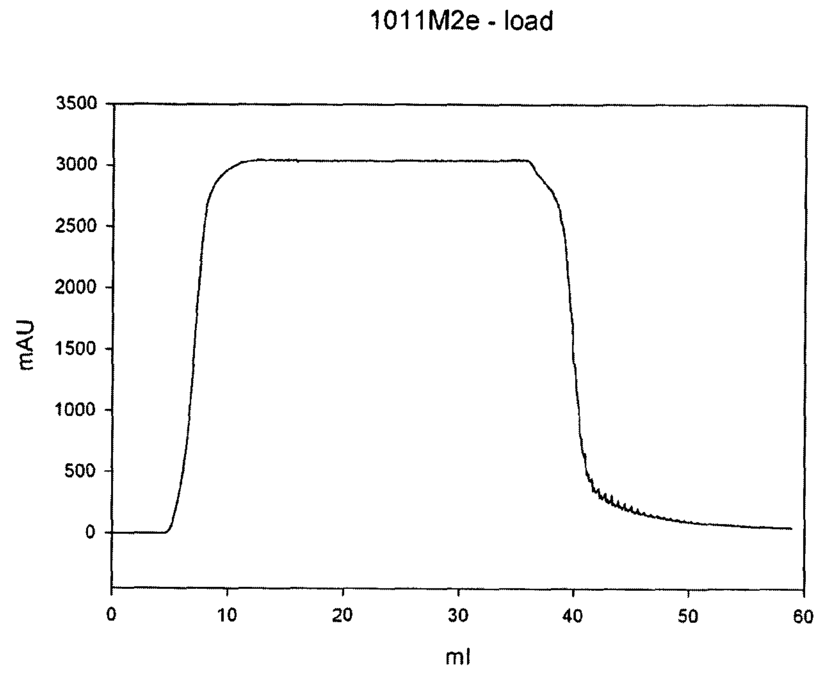
FIG. 8 Load profile of bound GST fusions of 1011M2e (FIG. 8A) and 2022M2e (FIG. 8B).
Figure 8B:
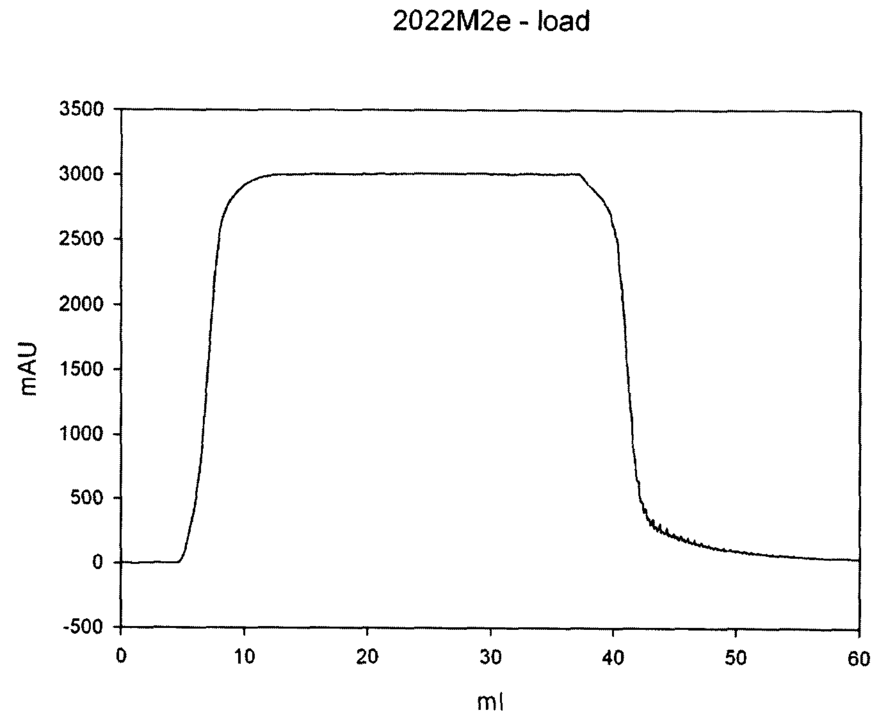
Figure 9A:
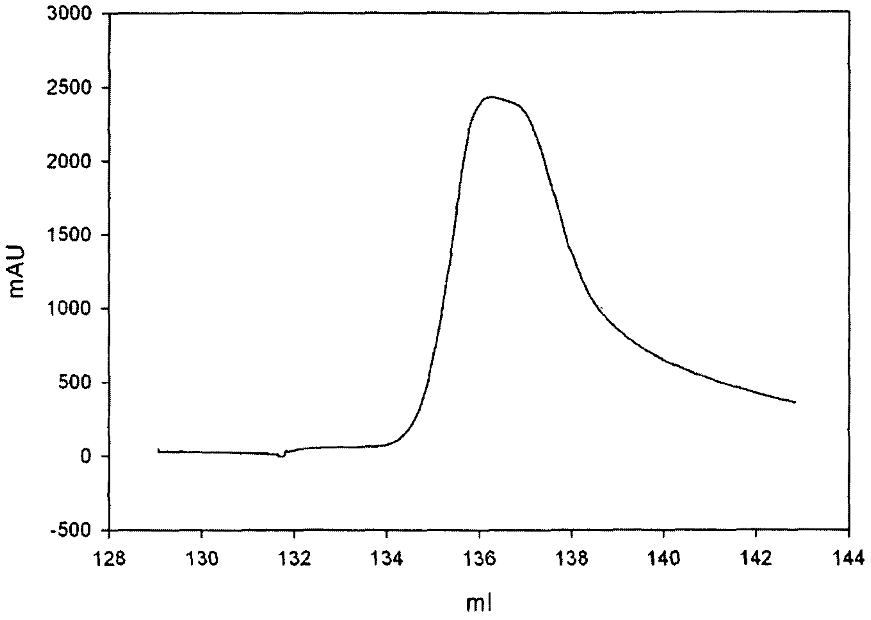
FIG. 9 Elution profile of bound GST fusions of 1011M2e (FIG. 9A) and 2022M2e (FIG. 9B).
Figure 9B:
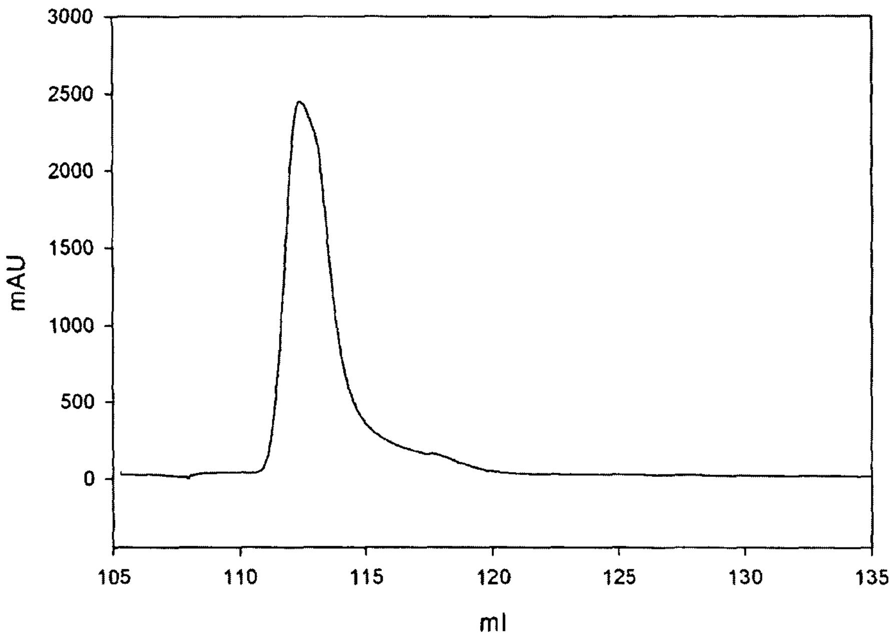
Figure 10A:
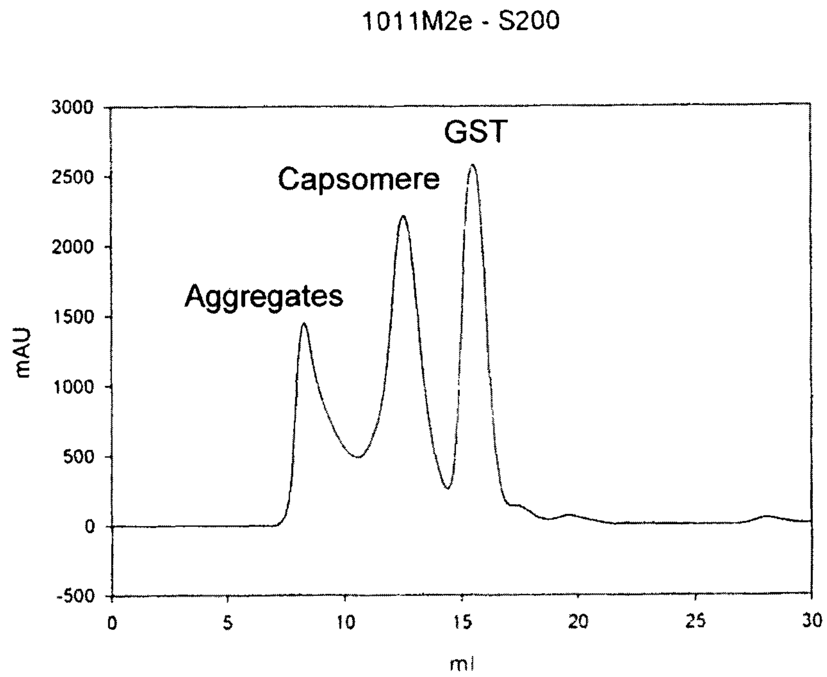
FIG. 10 S200 purification of chimeric VP1 dNdC 1011M2e and VP1 dNdC 2022M2e.
Figure 10B:
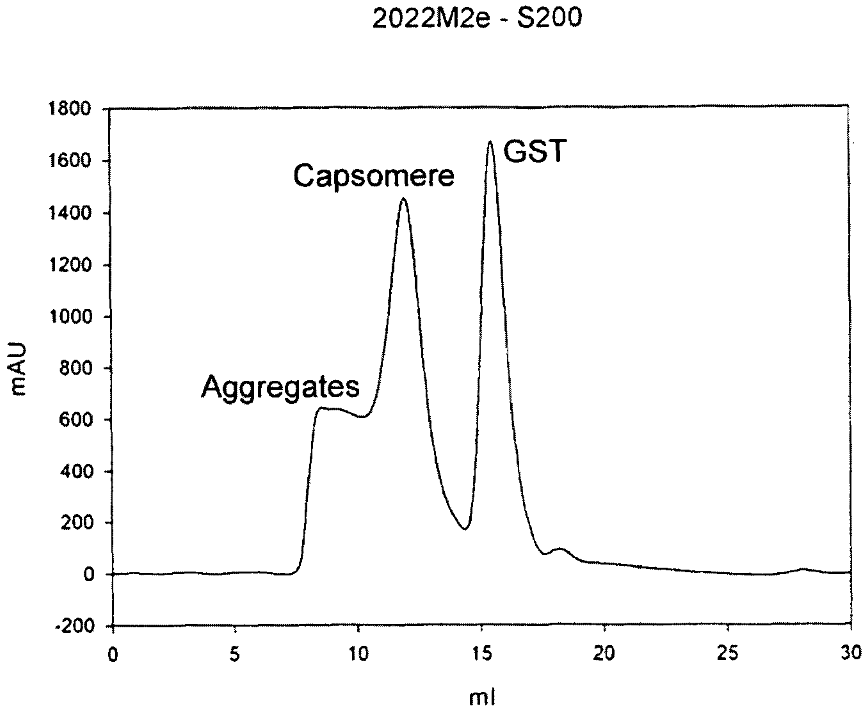

Protein purification was performed with an Äkta Explorer system from GE Healthcare. GST fusion proteins in the clarified homogenate were captured using a GSTrap™ HP 5 mL column from GE Healthcare pre-equilibrated with buffer L. The bound GST fusion proteins were eluted with elution buffer (Buffer L with 10 mM reduced glutathione) (FIGS. 8 and 9). Eluted samples were stored at −80° C. until required. 40 μL of Thrombin was added to 1 mL of purified GST fusion proteins followed by 2 hours incubation at room temperature. 1 mL of thrombin treated capsomere was injected onto a Superdex S200 10/300 GL size exclusion column (GE Healthcare) equilibrated in buffer L, to separate capsomeres from aggregates, GST and thrombin (FIG. 10). Capsomere fractions eluting at a volume of 11-13 mL were pooled, aliquoted and frozen at −80° C. for subsequent use. Capsomere sample was analysed by TEM (results not shown) and comprised distinct non-aggregated and non-assembled capsomeres suitable for use.

Animal Testing of VP1 dNdC 1011M2e and VP1 dNdC 2022M2e Capsomeres:

Adjuvant Formulation

Adjuvanted samples were prepared by mixing protein sample with alum adjuvant in 1:1 volume ratio, followed by incubation for one hour at room temperature on a roller mixer prior to immunisation.

Mice Immunisation

Mice were immunised with vaccine sample containing 50 μg of protein (<2 EU/ml) and 250 μg of alum adjuvant in a total of 50 μl volume through subcutaneous injections into the tail bases using 25-gauge needles. After the first immunisation on day 0, two other immunisations were given to the mice on days 21 and 42. Blood samples were taken by tail snip before the first immunisation (day 0), as well as on days 14, 35 and 56.

| | |
|---|---|
| Groups | 1. PBS + alum<br>2. VP1dC63<br>3. VP1dC63 + alum<br>4. VP1dNdC 1011M2e + alum<br>5. VP1dNdC 2022M2e<br>6. VP1 dNdC 2022M2e + alum |
| Dose | 50 μg of capsomeres |
| Volume | Total 50 μL |
| Adjuvant | Alum (250 μg) |
| Immunisation and bleeds | Inject days: 0, 21, 42<br>Bleed days: 0, 14, 35, 56 |

ELISA

Figure 11:
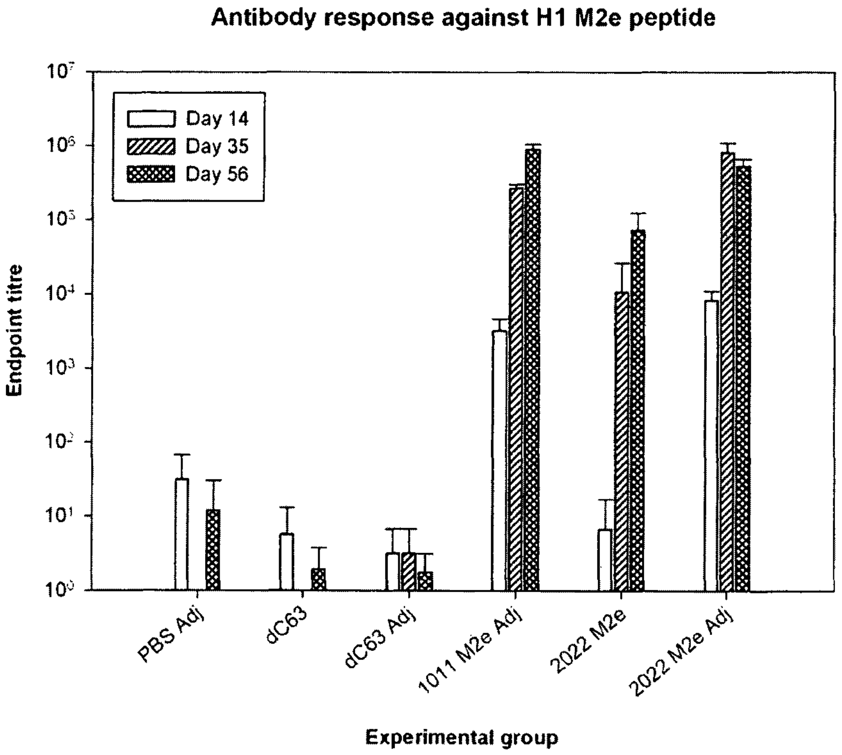
FIG. 11 Antibody response against H1 M2e peptide.

H1 M2e peptide at 10 μg/mL in carbonate coating buffer (50 mM $Na_2CO_3NaHCO_3$, pH 9.6) was adsorbed to 96-well NUNC immunoplates (Thermo Fisher Scientific, MA, USA), 100 μl per well overnight at 4° C. Plates were blocked with PBST (137 mM NaCl, 2.7 mM KCl, 10.15 mM $Na_2HPO_4$, 1.76 mM $KH_2PO_4$, pH 7.4, 0.05% (v/v) Tween 20) containing 5% skim milk (37° C., 90 min) and washed twice with PBST. Plates were incubated with mouse sera at 100-fold dilution followed by 2-fold serial dilutions (90 min, 37° C.). After washing 4 times with PBST, HRP-conjugated goat anti-mouse antibody (Sigma-Aldrich, USA) was added at 10000-fold dilution (90 min, 37° C.). Plates were washed 4 times with PBST and developed (0.4 mg/ml o-Phenylenediamine dihydrochioride (Sigma-Aldrich, USA), 50 mM Phosphate citrate buffer, 0.03% sodium perborate) prior to absorbance measurement at 450 nm. End point titers were determined as the highest dilution of serum for which the OD was 3SD above the mean OD of blank wells. The end point titers of each group are shown in FIG. 11. Antibodies specific to H1 M2e peptide are detected in mice immunised with 1011M2e and 2022M2e capsomeres. Higher end point titres were obtained from mice immunised with adjuvanted 1011M2e capsomeres than with unadjvanted 2022M2e capsomeres.

Example 3

Construction and Sequencing of Vectors Expressing Epitopes from Hendra Virus

*E. coli* codon optimised oligonucleotides were designed to insert epitopes G1-2 (GLPNQIMLQKTTS) SEQ ID NO: 24, G4 (VRPKSDSGDYN) SEQ ID NO: 25, G5 (PIIHSKYSKAE) SEQ ID NO: 26, G9 (VEIYDTGDSVIRPKL) SEQ ID NO: 27 and G10 (LEKIGSCTRGIAKQ) SEQ ID NO: 28 into the generic vector pGEX4T1-VP1 dNdC 0000.

Resulting constructs carrying Hendra Virus peptides are designated pGEX4T1-VP1 dNdC 1011G1-2, pGEX4T1-VP1 dNdC 1011G4, pGEX4T1-VP1 dNdC 1011G5, pGEX4T1-VP1 dNdC 1011G9 and pGEX4T1-VP1 dNdC 0.1011G10.

The amino acid sequences of VP1 dNdC 0000 with inserted peptides from Hendra Virus antigenic sequences are exemplified in FIG. 12.

Example 4

Construction and Sequencing of Vectors Expressing Antigenic Peptides from Group A *Streptococcus* (GAS)

*E. coli* codon optimised oligonucleotides were designed to insert GAS peptides $BSA10_{1-28}$ (NSKTPAPAPAVPVKKEATKSKLSEAELH) SEQ ID NO: 29, $2032_{1-19}$ (NSKNPVPVKKEAKLSEAEL) SEQ ID NO: 30 and $2040_{80-69}$ (LKMLNRDLEQAYNELSGEAH) SEQ ID NO: 31 into the generic vector pGEX4T1-VP1 dNdC 0000. These peptides are from the paper by Brandt et al (Infection and Immunity, December 2000, p 6587-6594, 68(12)). Resulting constructs carrying GAS peptides are designated pGEX4T1-VP1 dNdC 1011GAS1, pGEX4T1-VP1 dNdC 1011GAS2, pGEX4T1-VP1 dNdC 1011GAS3. The amino acid sequences of VP1 dNdC 0000 with inserted peptides from GAS antigenic sequences are exemplified in FIG. 13.

Example 5

Production of Chimeric VP1 Capsomere with M2e Inserted on N-Terminus and HA Epitopes on Surface Loops S1 and S4

Construction of Vectors Carrying M2e and HA Epitopes a and B:

*E. coli* codon optimised oligonucleotides were designed to insert M2e peptide (SLLTEVETPTRNEWECRCSDSSD) SEQ ID NO: 23, HA epitopes A (PYNGKSS) SEQ ID NO: 33 and B (GNDAAEQTKLYQNPTTY) SEQ ID NO: 34 into the generic vectors. M2e oligo was inserted on the N-terminal of VP1 using the BamHI restriction site upstream of VP1 gene. Oligo for HA epitope A is inserted into the surface loop S1 for construct pGEX4T1-M2e-VP1-S1A. Oligos for HA epitopes B and A are inserted into the surface loops S1 and S4, respectively, to generate construct pGEX4T1-M2e-VP1-S1B-S4A.

Resulting constructs carrying M2e and HA epitopes A and B are designated pGEX4T1-M2e-VP1-S1A and pGEX4T1-M2e-VP1-S1B-S4A. The sequence of M2e and HA epitopes A and B are of H5N1 (A/Vietnam/3028/2004). The amino acid sequences of chimeric VP1 with inserted peptides are exemplified in FIG. 14.

Figure 15:
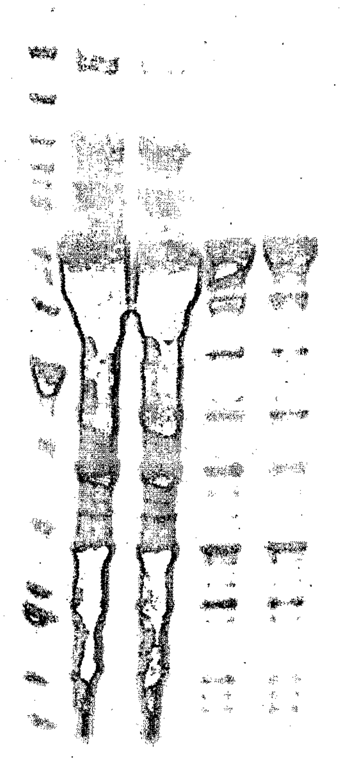
FIG. 15 SDS-PAGE analysis of expression. Left to right: Lane 1: Protein molecular weight marker; Lane 2: M2e-VP1-S1A total expression; Lane 3: M2e-VP1-S1A soluble expression; Lane 4: M2e-VP1-S1B-S4A total expression; Lane 5: M2e-VP1-S1B-S4A soluble expression.

Expression of M2e-VP1-S1A and M2e-VP1-S1B-S4A:

Expression was conducted as outlined in Example 2. The cell pellets were analysed on SDS-PAGE for total and soluble expression (FIG. 15).

Figure 16:
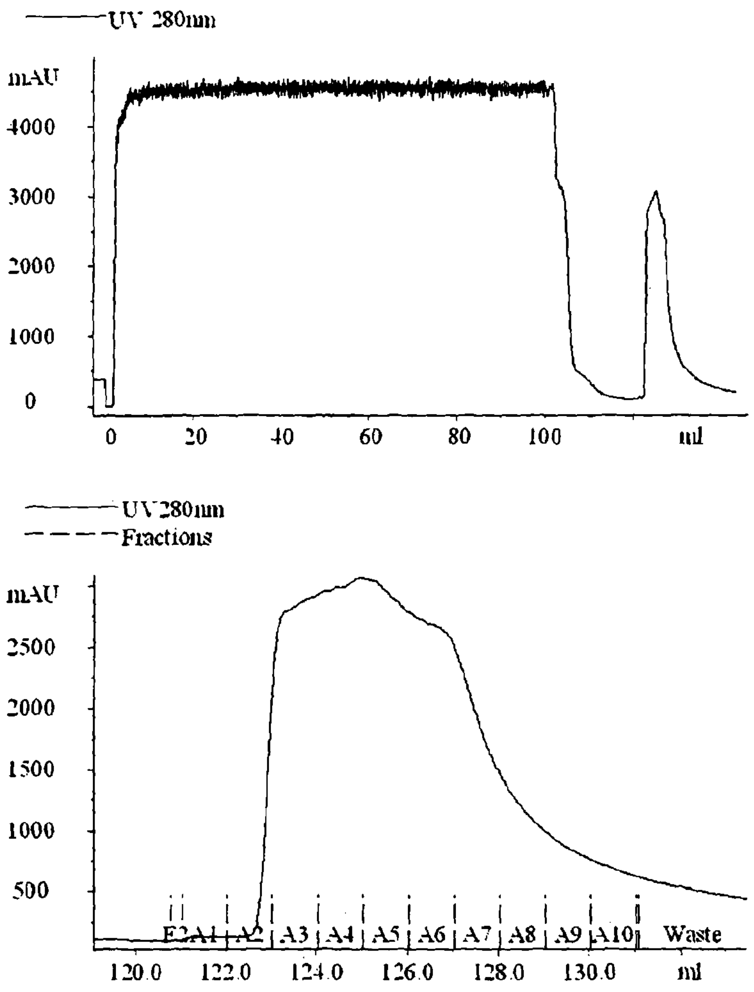
FIG. 16 GST affinity purification for M2e-VP1-S1A.
Figure 17:
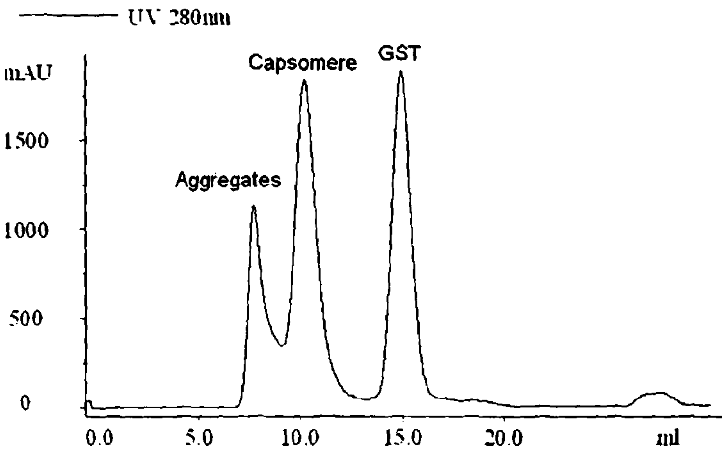
FIG. 17 S200 purification for M2e-VP1-S1A.
Figure 18:
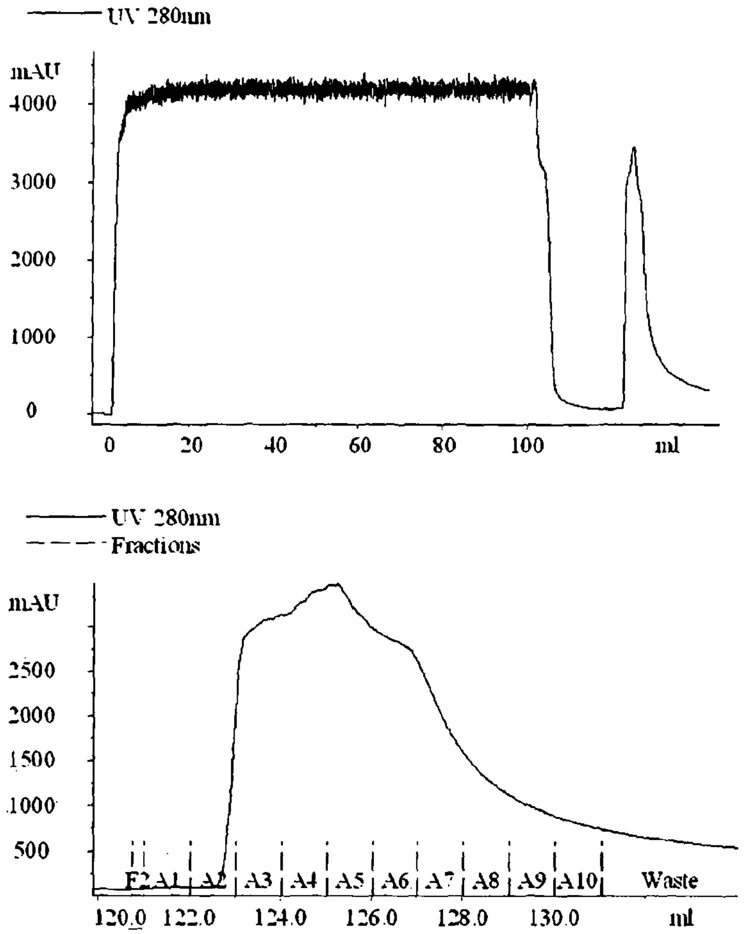
FIG. 18 GST affinity purification for M2e-VP1-S1B-S4A.
Figure 19:
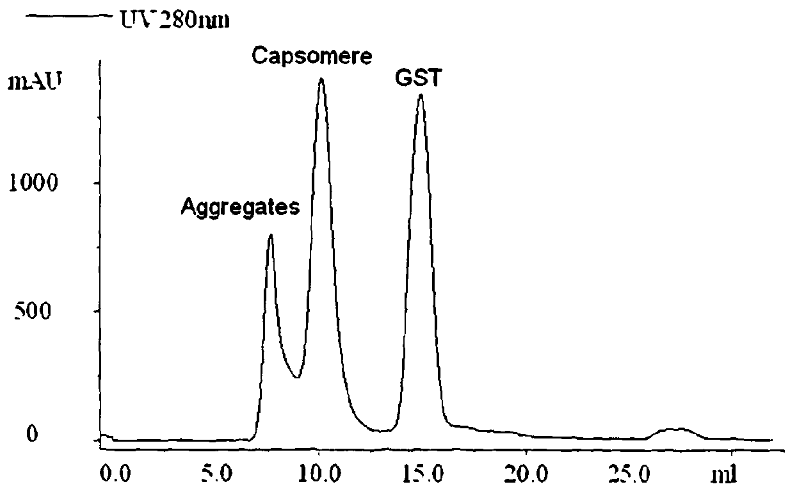
FIG. 19 S200 purification for M2e-VP1-S1B-S4A.

Purification of M2e-VP1-S1A and M2e-VP1-S1B-S4A Capsomeres:

Chimeric capsomeres were purified as in protocol outlined in Example 2. The GST affinity purification profiles are shown in FIGS. 16 and 18. Chimeric capsomeres were obtained after S200 purification (FIGS. 17 and 19).

Example 6

Construction and Sequencing of Vectors Expressing Antigenic Peptides from HPV E7

*E. coli* codon optimised oligonucleotides were designed to insert E7 peptides (QAEPDRAHYNIVTFCCKCD—SEQ ID NO: 35 and RAHYNIVTF SEQ ID NO: 36) into the generic vector pGEX4T1-VP1 dNdC 0000. Resulting constructs carrying E7 peptides are designated pGEX4T1-VP1 dNdC 1011E7 and pGEX4T1-VP1 dNdC 1011CTL. The amino acid sequences of VP1 dNdC 0000 with inserted peptides from HPV E7 antigenic sequences are exemplified in FIG. 20.

Example 7

Expression of Chimeric VP1 Capsomeres with M2e Peptide Inserted into N and/or C Termini and/or Surface Loops S1 and S4

Figure 21:
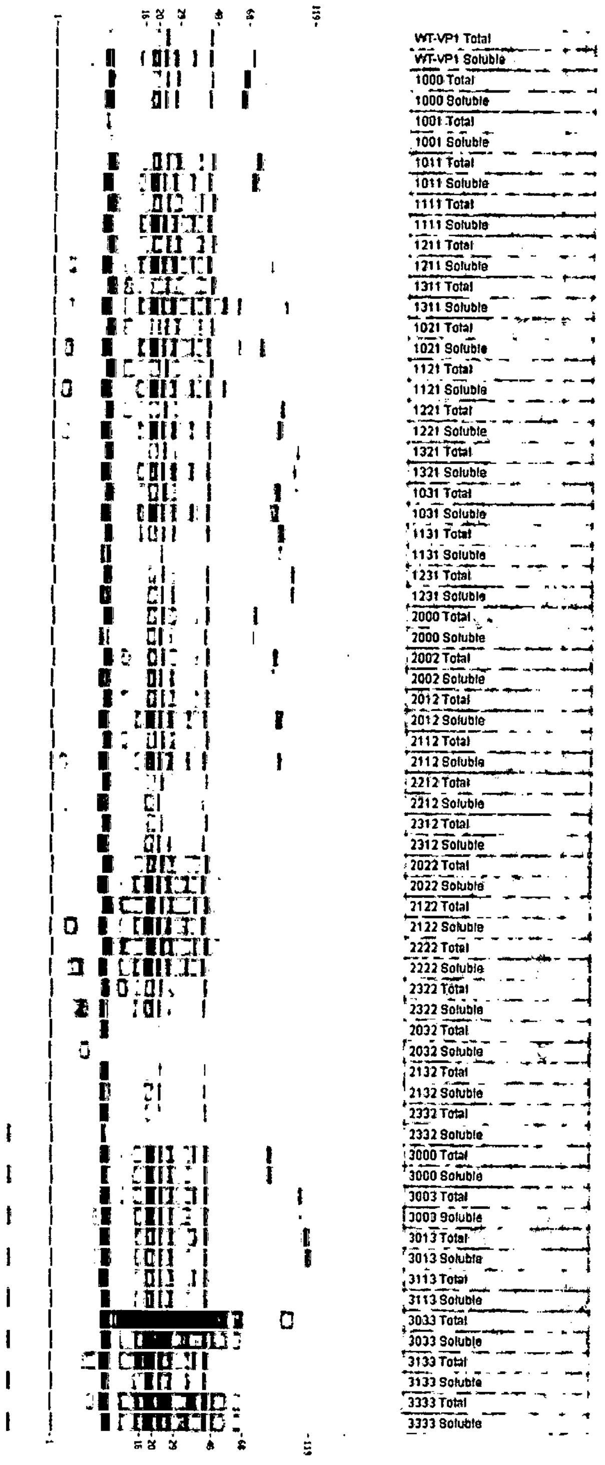
FIG. 21 Expression of chimeric VP1 capsomeres with M2e peptide inserted into N and/or C termini and/or surface loops S1 and S4 analysed using Calliper LabChip GXII.
Figure 22:
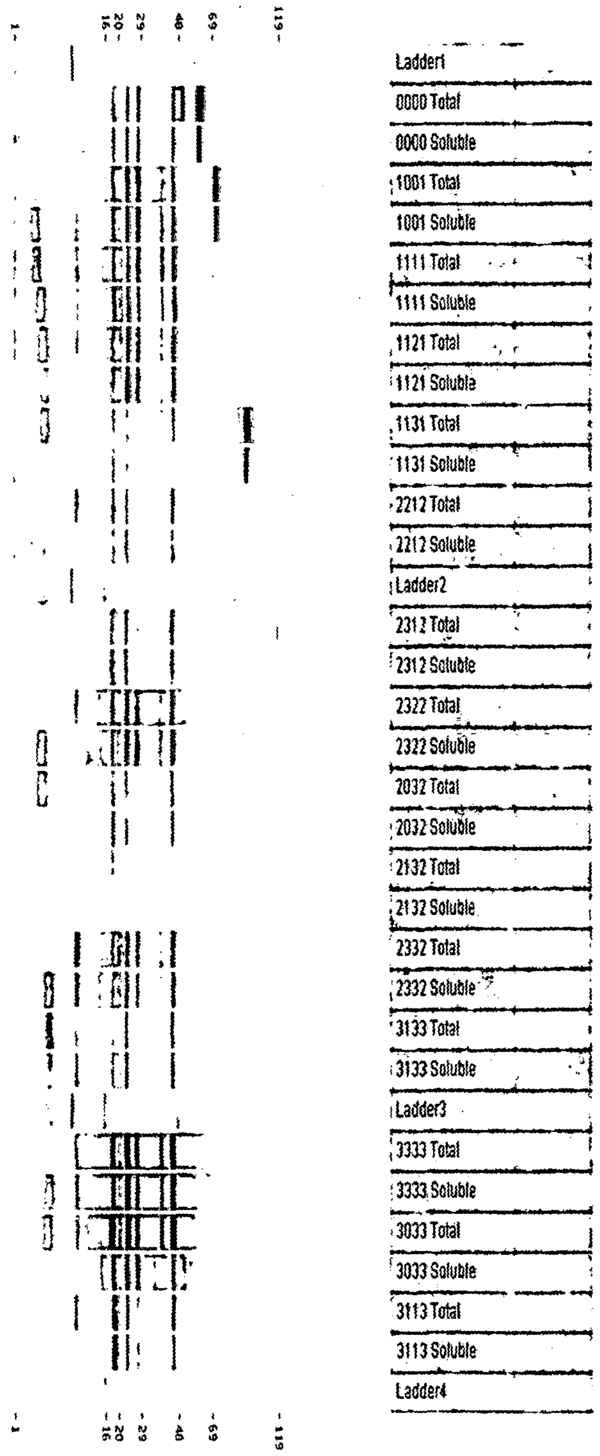
FIG. 22 Expression of chimeric VP1 capsomeres with M2e peptide inserted into N and/or C termini and/or surface loops S1 and S4 analysed using Calliper LabChip GXII.

Chimeric VP1 with M2e peptide inserted into N and/or C termini and/or surface loops were constructed as described in Example 2. All constructs were expressed according to the protocol outlined in Example 2. Table 1 below illustrates the insertions on various constructs and the final OD during expression. The total and soluble expression of all constructs were analysed using Calliper LabChip GXII as shown in FIGS. 21 and 22.

Example 8

Capsomere Vaccines Adjuvanted with VLPs, Nanoparticles, Alum and Nanoemulsion Adjuvant Preparation VLPs:

Wild-type capsomeres were prepared as described hereinbefore. Endotoxin in capsomere samples was removed through Vivapure® Q spin column (Sartorius, Germany). Capsomeres were then dialysed against GL1 assembly buffer at room temperature for 15 hours to promote VLP assembly, and then dialysed against PBS at 4° C. for 24 hours. VLP concentration was adjusted to a protein VP1 concentration of 2 mg/ml.

Nanoparticles:

Commercial silica nanoparticles of nominal diameter 50 nm and 1 μm (Cat.#24040 and 24326, Polysciences, Inc., US) were dialysed against PBS at 4° C. for 24 hours. Both solutions were adjusted to a nominal silica concentration of 2 mg/ml.

Alum:

Commercial alum hydroxide Alhydrogel® adjuvant (Brenntag, Germany) was used. Alum was prepared at concentration of 10 mg/ml (as received) and 2 mg/ml (by dilution with PBS).

Nanoemulsion.

A mixture containing 400 μM of peptide surfactant AM1 and 800 μM $ZnCl_2$ in 25 mM HEPES pH 7.0 was prepared. 20 μl of Miglyol 812 (Sasol, Germany) was added into 980 μl of the mixture and then sonicated using Branson Sonifier 450 (Sonifier, US) for 2×45 seconds at output 15. The resulting nanoemulsion was then added drop by drop into 80 mg/ml BSA in 1:1 volume. The size of emulsion (~200 nm) was confirmed with Dynamic Light Scattering (Malvern Instruments Ltd, UK). All protocols were prepared using endotoxin free reagents and apparatus.

Vaccine Preparation

1011 H1 M2e vaccine sample, prepared as described hereinbefore, was processed to give a sample in PBS having a VP1 protein concentration of 2 mg/ml and an endotoxin level of 0.980 EU/ml, measured using Endosafe® (Charles-River Laboratories, US). Samples were stored at 80° C.

Immunisations

Vaccine samples were thawed gently on ice few hours before injection. Thawed samples were mixed with each adjuvant preparation at 1:1 volume. Samples adjuvanted with nanoparticles, nanoemulsion and alum were incubated at room temperature for 1 h prior to use, Mice were immunised with 50 μl of vaccine sample through subcutaneous tail base injection on days 0, 21 and 42. Blood samples (504 each) were taken by tail snip before the first immunisation (day 0), and on days 14, 35 and 56.

Figure 23:
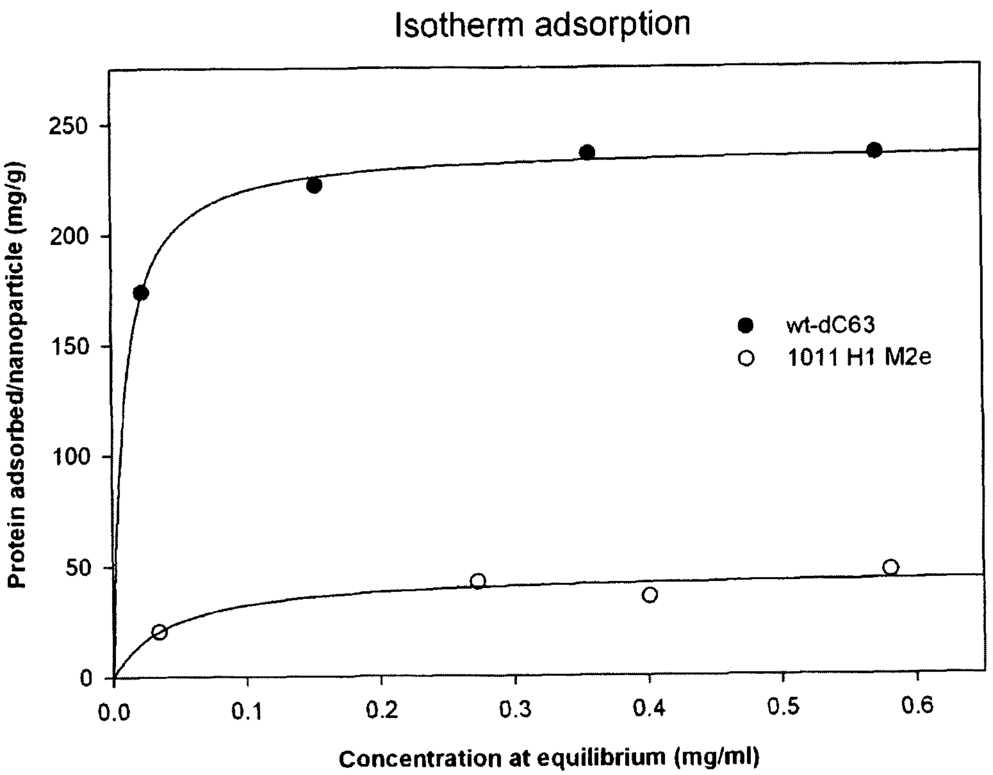
FIG. 23 Isotherm adsorption of both VP1 delta C63 capsomeres and chimeric 1011M2e capsomeres.

Isotherm adsorption of both VP1 dC63 capsomeres and chimeric. 1011M2e capsomeres were measured. FIG. 23 indicates that chimeric 1011M2e capsomeres did not attach substantially to the nanoparticles (silica 50 nm).

Figure 24:
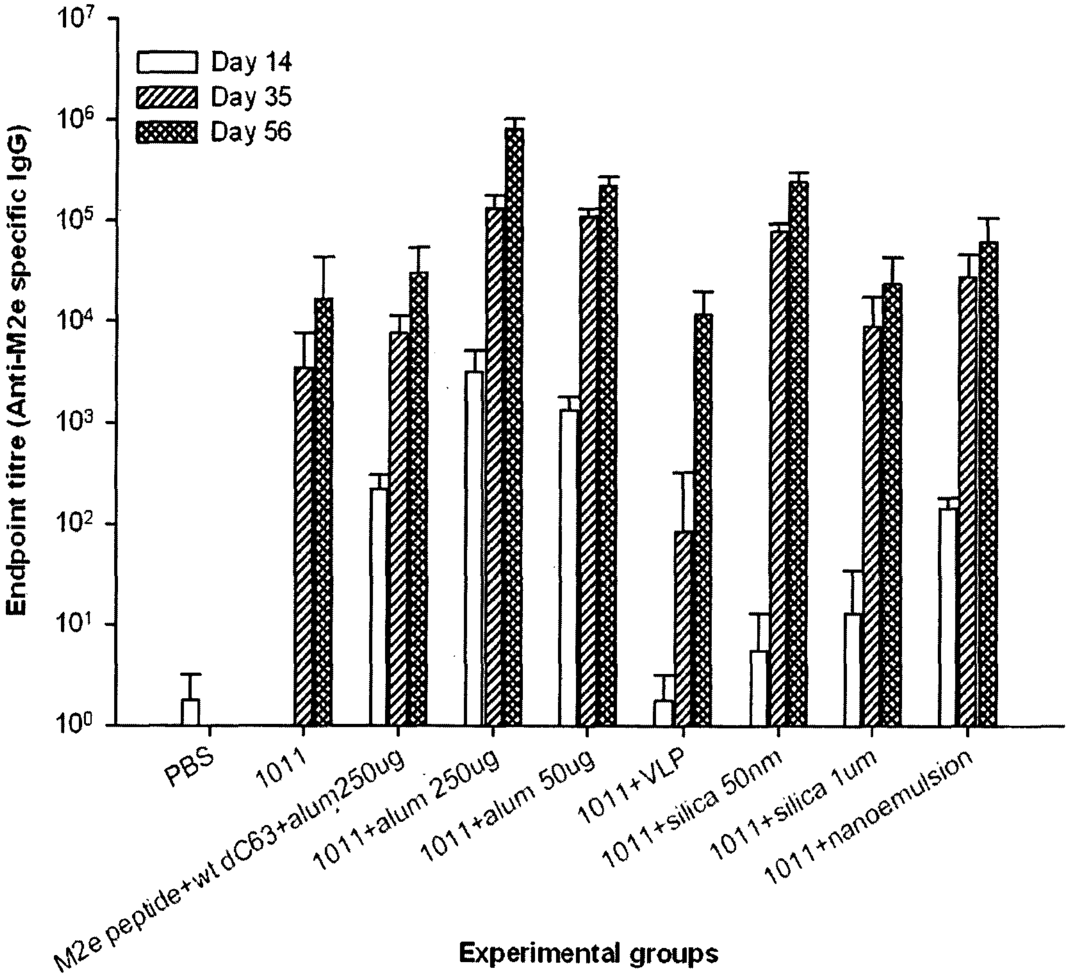
FIG. 24 Antibody response to H1 M2e peptide.
Figure 25:
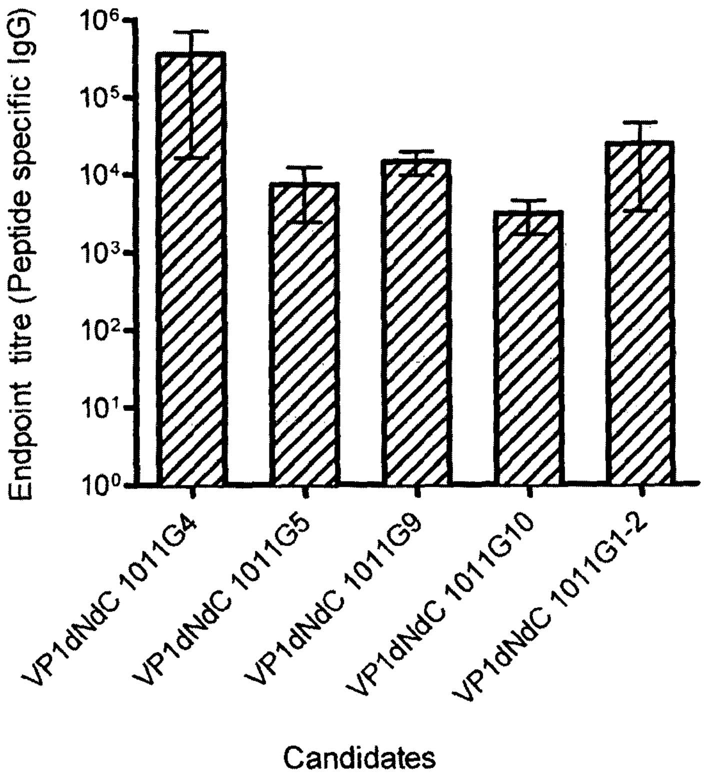
FIG. 25 Antibody response to peptide epitopes from Hendra virus.
Figure 26:
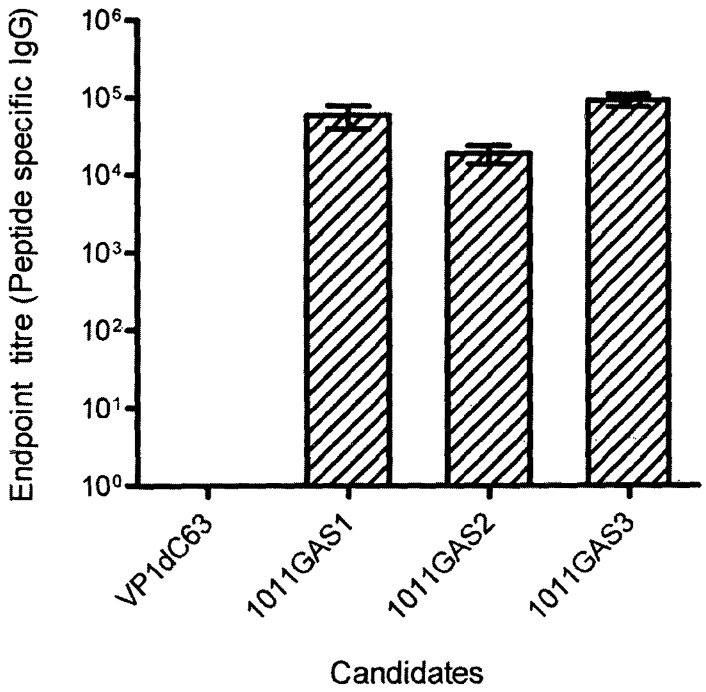
FIG. 26 Antibody response to peptide epitopes from Group A *Streptococcus* (GAS).

Animal testing results are shown in FIGS. 24, 25 and 26. FIG. 24 shows the end point titers of each group. Antibodies specific to H1 M2e peptide are detected in all groups except for negative control (PBS). Higher antibody titres are detected after second injection. Also demonstrated in FIG. 24 is that the presence of 50 nm nanoparticles gives a better response than the free capsomeres. Based on data in FIG. 23, it is expected that less than 5% of the antigen is attached to the 50 nm nanoparticles. Thus there is no substantial association. This is a very unexpected result and directly challenges the dogma of conjugation or adsorption. It also is unexpected in the context of the conventional thinking which believes that there is a positive benefit of adsorption. What is also noted from FIG. 24 is the following:

- the silica formulation is beneficial versus the free capsomeres.
- the immunogenicity of the 50 nm silica formulation does not differ substantially from the alum preparation, even though Ag is not substantially associated with the silica, yet we expect the Ag to be fully associated with the 250 μg alum.
- a comparison of the peptide+dC63+alum 250 μg vs alum 250 μg data shows a clear benefit of functionally linking the antigen to the N-, C- and loop of VP1. The former is a formulation of free peptide (9.7 μg), non-chimeric VP1 dC63 (40.3 μg) and alum (250 μg). The latter is chimeric VP1 dNdC 1011 (50 μg, comprising 9.7 μg of M2e peptide equivalent within a chimeric 1011 capsomere). The chimeric capsomere is clearly superior (surprisingly so) versus the peptide antigen.

FIG. 25 shows capsomere vaccines expressing epitopes from Hendra virus, adjuvanted with 50 nm nanoparticles. VP1dNdC 1011G4 (SEQ ID NO: 10), VP1dNdC 1011G5 (SEQ ID NO: 11), VP1dNdC 1011G9 (SEQ ID NO: 12), VP1dNdC 1011G10 (SEQ ID NO: 13), and VP1dNdC 1011G1-2 (SEQ ID NO: 9) vaccine samples and 50 nm silica nanoparticles adjuvant were prepared as described hereinbefore (see Example 8). Immunisations of mice were also as described hereinbefore (see Example 8). FIG. 25 shows the endpoint titers of peptide-specific antibody of each group at the last bleed. FIG. 26 shows capsomere vaccines expressing epitopes from Group A *Streptococcus* (GAS), adjuvanted with 50 nm nanoparticles. 1011GAS1 (SEQ ID NO: 14), 1011GAS2 (SEQ ID NO: 15), and 1011GAS3 (SEQ ID NO: 16) vaccine samples were prepared as described hereinbefore (Example 8). 50 nm silica nanoparticles, prepared as described hereinbefore (Example 8), were adjusted to nominal silica concentration of 10 mg/ml. Immunisations of mice were as described hereinbefore as well (Example 8). FIG. 26 shows the endpoint titers of peptide-specific antibody of each group at the last bleed.

Figure 28:
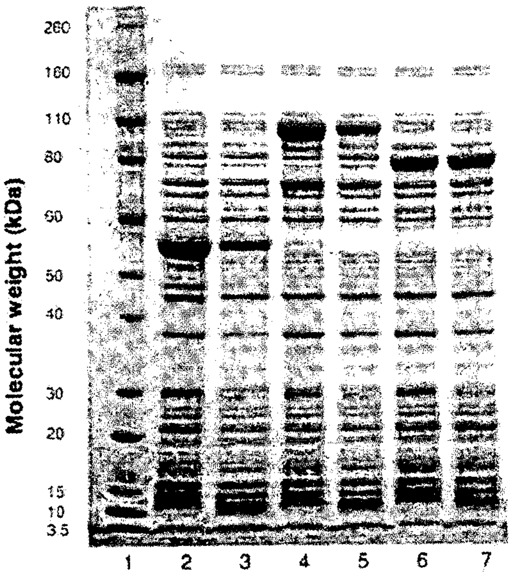
FIG. 28 Expression of chimeric VP1 capsomeres with large antigen inserted on the N-terminal (Left to right: Lane 1. Molecular weight marker; Lane 2. VP1 dNdC 0000 total protein; Lane 3. VP1 dNdC 0000 soluble protein; Lane 4. ADI-VP1 dNdC total protein; Lane 5. ADI-VP1 dNdC soluble protein; Lane 6. TF-VP1 dNdC total protein; and Lane 7. TF-VP1 dNdC soluble protein).

Arginine deimonase (ADI) and trigger factor (TF) from *Streptococcus pyogenes* (FIGS. 27 A and B—SEQ ID NOs: 42 and 43) were cloned into the N-terminus of VP1 dNdC S1 S4 (SEQ ID NO: 5), separately. The resulting constructs were ADI-VP1 dNdC (SEQ ID NO: 21) and TF-VP1 dNdC (SEQ ID NO: 22) as detailed in FIG. 29. The expression of both constructs was investigated as described hereinbefore (Example 2). The cell pellets were analysed on SDS-PAGE for total and soluble expression (FIG. 28). High levels of soluble expression were detected for both constructs as shown in FIG. 28.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

TABLES

TABLE 1

Insertions on various constructs and the final OD during expression. 1-3 copies of M2e are inserted into N and/or C and/or surface loops S1 and S4 of VP1 dNdC 0000 vector. For example, a construct designated as 1000 has 1 copy of M2e inserted into the N terminus of truncated VP1, and a construct designated as 1111 has 1 copy of M2e insert into N and C termini, as well as into surface loop sites 1 and 4.

| Constructs | N-term | S1 | S4 | C-term | M2e copy | $OD_{600}$ Induction | $OD_{600}$ Harvest |
|---|---|---|---|---|---|---|---|
| WT-VP1 | | | | | | 0.54 | 9.89 |
| 0000 | 0 | 0 | 0 | 0 | 0 | 0.73 | 9.81 |
| 1000 | 1 | 0 | 0 | 0 | 1 | 0.67 | 8.34 |
| 1001 | 1 | 0 | 0 | 1 | 2 | 0.80 | 10.54 |
| 1011 | 1 | 0 | 1 | 1 | 3 | 0.61 | 6.82 |
| 1111 | 1 | 1 | 1 | 1 | 4 | 0.49 | 9.54 |
| 1211 | 1 | 2 | 1 | 1 | 5 | 0.50 | 8.41 |
| 1311 | 1 | 3 | 1 | 1 | 6 | 0.51 | 10.05 |
| 1021 | 1 | 0 | 2 | 1 | 4 | 0.49 | 8.90 |
| 1121 | 1 | 1 | 2 | 1 | 5 | 0.52 | 9.12 |
| 1221 | 1 | 2 | 2 | 1 | 6 | 0.67 | 6.20 |
| 1321 | 1 | 3 | 2 | 1 | 7 | 0.54 | 5.74 |
| 1031 | 1 | 0 | 3 | 1 | 5 | 0.67 | 9.62 |
| 1131 | 1 | 1 | 3 | 1 | 6 | 0.69 | 6.84 |
| 1231 | 1 | 2 | 3 | 1 | 7 | 0.57 | 4.77 |
| 2000 | 2 | 0 | 0 | 0 | 2 | 0.52 | 7.69 |
| 2002 | 2 | 0 | 0 | 2 | 4 | 0.49 | 6.06 |
| 2012 | 2 | 0 | 1 | 2 | 5 | 0.59 | 6.30 |
| 2112 | 2 | 1 | 1 | 2 | 6 | 0.53 | 5.31 |
| 2212 | 2 | 2 | 1 | 2 | 7 | 0.60 | 5.70 |
| 2312 | 2 | 3 | 1 | 2 | 8 | 0.69 | 4.46 |
| 2022 | 2 | 0 | 2 | 2 | 6 | 0.53 | 8.01 |
| 2122 | 2 | 1 | 2 | 2 | 7 | 0.50 | 10.12 |
| 2222 | 2 | 2 | 2 | 2 | 8 | 0.51 | 10.86 |
| 2322 | 2 | 3 | 2 | 2 | 9 | 0.62 | 9.55 |
| 2032 | 2 | 0 | 3 | 2 | 7 | 0.68 | 6.16 |
| 2132 | 2 | 1 | 3 | 2 | 8 | 0.51 | 3.79 |
| 2332 | 2 | 3 | 3 | 2 | 10 | 0.78 | 6.41 |
| 3000 | 3 | 0 | 0 | 0 | 3 | 0.49 | 9.93 |
| 3003 | 3 | 0 | 0 | 3 | 6 | 0.49 | 7.93 |
| 3013 | 3 | 0 | 1 | 3 | 7 | 0.76 | 6.60 |
| 3113 | 3 | 1 | 1 | 3 | 8 | 0.62 | 6.71 |
| 3033 | 3 | 0 | 3 | 3 | 9 | 0.48 | 11.01 |
| 3133 | 3 | 1 | 3 | 3 | 10 | 0.66 | 4.89 |
| 3333 | 3 | 3 | 3 | 3 | 12 | 0.65 | 11.20 |

The invention claimed is:

1. An isolated protein comprising:

a viral capsomere-forming amino acid sequence, wherein said viral capsomere-forming amino acid sequence comprises an amino acid sequence of a polyomavirus capsomere lacking at least part of the amino-terminus and/or the carboxy-terminus that is normally present in the amino acid sequence of the polyomavirus capsomere; and a heterologous immunogenic amino acid sequence at the amino-terminus of the polyomavirus capsomere amino acid sequence that is not a purification tag amino acid sequence and/or expression-enhancing tag amino acid sequence, wherein said isolated protein is essentially incapable of assembly into virus-like particles (VLPs) as a result of lacking VLP assembly-related parts of the viral capsomere-forming amino acid sequence and/or the addition of said immunogenic amino acid sequence at the amino-terminus of said viral capsomere-forming amino acid sequence, and thereby retains a capsomere morphology.

2. The isolated protein of claim 1, wherein the virus is a murine polyomavirus.

3. The isolated protein of claim 1, wherein the protein is polyomavirus VP1.

4. The isolated protein of claim 3, wherein the protein is a murine polyomavirus VP1.

5. The isolated protein of claim 1, wherein the viral capsomere-forming amino acid sequence comprises an amino acid sequence as set forth in any one of SEQ ID NOs: 4 to 22.

6. The isolated protein of claim 1, wherein the viral capsomere-forming amino acid sequence further comprises a heterologous immunogenic amino acid sequence that is not a purification tag amino acid sequence and/or expression-enhancing tag amino acid sequence at the carboxy-terminus of the viral capsomere amino acid sequence, wherein said immunogenic amino acid sequence is the same as or different to the heterologous immunogenic amino acid sequence at the amino-terminus of the viral capsomere amino acid sequence.

7. The isolated protein of claim 1, further comprising a heterologous immunogenic amino acid sequence that is not a purification tag amino acid sequence and/or expression-enhancing tag amino acid sequence in one or more exposed loops of said viral capsomere-forming amino acid sequence, wherein said immunogenic amino acid sequence is the same as or different to the heterologous immunogenic amino acid sequence at the amino-terminus of the viral capsomere amino acid sequence.

8. The isolated protein of claim 1, wherein the immunogenic amino acid sequence is of an immunogen from a pathogenic organism selected from the group consisting of a virus, a bacteria, a fungi, a parasite, a cancer immunogen, an allergic reaction immunogen a transplantation immunogen and an autoantigen.

9. The isolated protein of claim 8, wherein the immunogenic amino acid is of a virus.

10. The isolated protein of claim 9, wherein the virus is selected from the group consisting of influenza, Hendra and papillomavirus.

11. The isolated protein of claim 10, wherein the immunogenic amino acid sequence is as set forth in any one of SEQ ID NOs: 23, 24, 25, 26, 27, 28, 32, 33, 34, 35, 36, 37, 38, 39, 40 and 41.

12. The isolated protein of claim 8, wherein the immunogenic amino acid is of a bacterium.

13. An isolated nucleic acid encoding an isolated protein or amino acid sequence of claim 1.

14. A genetic construct comprising the isolated nucleic acid of claim 13.

15. An isolated host cell comprising the genetic construct of claim 14.

16. A capsomere comprising one or more isolated proteins of claim 1.

17. A method of producing a capsomere, comprising the steps of (a) introducing into a host cell:

an isolated nucleic acid encoding the isolated protein of claim 1;

a genetic construct comprising an isolated nucleic acid encoding the isolated protein of claim 1;

(b) culturing said host cell under conditions which facilitate production of the isolated protein encoded by the isolated nucleic acid;

(c) optionally purifying the isolated protein; and (d) assembling the isolated protein to thereby produce the capsomere.

18. A pharmaceutical composition comprising one or more agents selected from the group consisting of:

an isolated protein comprising a viral capsomere-forming amino acid sequence wherein said viral capsomere-forming amino acid sequence comprises an amino acid sequence of a polyomavirus capsomere lacking at least part of the amino-terminus and/or the carboxy-terminus that is normally present in the amino acid sequence of the polyomavirus capsomere; and a heterologous immunogenic amino acid sequence at the amino-terminus of the polyomavirus capsomere amino acid sequence that is not a purification tag amino acid sequence and/or expression-enhancing tag amino acid sequence, wherein said isolated protein is essentially incapable of assembly into VLPs as a result of lacking VLP assembly-related parts of the viral capsomere-forming amino acid sequence and/or the addition of said immunogenic amino acid sequence at the amino-terminus of said viral capsomere-forming amino acid sequence, and thereby retains a capsomere morphology; and an isolated nucleic acid encoding an isolated protein comprising a viral capsomere-forming amino acid sequence wherein said viral capsomere-forming amino acid sequence comprises an amino acid sequence of a polyomavirus capsomere lacking at least part of the amino-terminus and/or the carboxy-terminus that is normally present in the amino acid sequence of the polyomavirus capsomere; and a heterologous immunogenic amino acid sequence at the amino-terminus of the polyomavirus capsomere amino acid that is not a purification tag amino acid sequence and/or expression-enhancing tag amino acid sequence, wherein said isolated protein encoded by said isolated nucleic acid is essentially incapable of assembly into VLPs as a result of lacking VLP assembly-related parts of the viral capsomere-forming amino acid sequence and/or the addition of said immunogenic amino acid sequence at the amino-terminus of said viral capsomere-forming amino acid sequence, and thereby retains a capsomere morphology; and a capsomere comprising one or more isolated proteins comprising a viral capsomere-forming amino acid sequence wherein said viral capsomere-forming amino acid sequence comprises an amino acid sequence of a polyomavirus capsomere lacking at least part of the amino-terminus and/or the carboxy-terminus that is normally present in the amino acid sequence of the polyomavirus capsomere; and a heterologous immunogenic amino acid sequence at the amino-terminus of the viral capsomere amino acid that is not a purification tag amino acid sequence and/or expression-enhancing tag amino acid sequence, wherein said one or more isolated proteins of said capsomere are essentially incapable of assembly into VLPs as a result of lacking VLP assembly-related parts of the viral capsomere-forming amino acid sequence and/or the addition of said immunogenic amino acid sequence at the amino-terminus of said viral capsomere-forming amino acid sequence, and thereby retain a capsomere morphology; and, a pharmaceutically-acceptable carrier, diluent or excipient.

19. The pharmaceutical composition of claim 18, wherein the pharmaceutical composition is an immunotherapeutic composition.

20. The pharmaceutical composition of claim 18, wherein the pharmaceutical composition is a vaccine.

21. A method of eliciting or augmenting an immune response in an animal, said method comprising the step of administering a pharmaceutical composition comprising one or more agents selected from the group consisting of the isolated protein of claim 1, an isolated nucleic acid encoding the isolated protein of claim 1, and a capsomere comprising the isolated protein of claim 1; and, a pharmaceutically-acceptable carrier, diluent or excipient; to thereby elicit or augment an immune response in said animal.

22. The method of claim 21, wherein the animal is thereby immunised.

23. The method of claim 21, wherein a disease, disorder or condition of the animal is thereby prophylactically or therapeutically treated.

24. The isolated protein of claim 12, wherein the immunogenic amino acid sequence is as set forth in any one of SEQ ID NOs: 29, 30, 31, 42 and 43.

25. The isolated protein of claim 1, wherein the viral capsomere-forming amino acid sequence comprises an amino acid sequence of a polyomavirus capsomere lacking at least part of the amino-terminus and the carboxy-terminus that is normally present in the amino acid sequence of the polyomavirus capsomere.

26. The isolated protein of claim 6, wherein the viral capsomere-forming amino acid sequence comprises an amino acid sequence of a polyomavirus capsomere lacking at least part of the amino-terminus and the carboxy-terminus that is normally present in the amino acid sequence of the polyomavirus capsomere.

27. The isolated protein of claim 26 further comprising a heterologous immunogenic amino acid sequence that is not a purification tag amino acid sequence and/or expression-enhancing tag amino acid sequence in one or more exposed loops of the viral capsomere-forming amino acid sequence, wherein said immunogenic amino acid sequence is the same as or different to the heterologous immunogenic amino acid sequence at the amino-terminus of the viral capsomere amino acid sequence.

28. The isolated protein of claim 1, consisting essentially of non-aggregated protein with capsomere morphology.

* * * * *